US009266925B2

(12) United States Patent
Zecri et al.

(10) Patent No.: US 9,266,925 B2
(45) Date of Patent: Feb. 23, 2016

(54) CYCLIC POLYPEPTIDES FOR THE TREATMENT OF HEART FAILURE

(71) Applicants: Frederic Zecri, Brookline, MA (US); Philipp Grosche, Inzlingen (DE); Kayo Yasoshima, Cambridge, MA (US); Hongjuan Zhao, Lexington, MA (US); Jun Yuan, Boston, MA (US); Aimee Richardson Usera, Winchester, MA (US); Changgang Lou, Portage, MI (US); Aaron Kanter, Somerville, MA (US); Alexandra Marshall Bruce, Cambridge, MA (US); Carla Giumaraes, Boston, MA (US)

(72) Inventors: Frederic Zecri, Brookline, MA (US); Philipp Grosche, Inzlingen (DE); Kayo Yasoshima, Cambridge, MA (US); Hongjuan Zhao, Lexington, MA (US); Jun Yuan, Boston, MA (US); Aimee Richardson Usera, Winchester, MA (US); Changgang Lou, Portage, MI (US); Aaron Kanter, Somerville, MA (US); Alexandra Marshall Bruce, Cambridge, MA (US); Carla Giumaraes, Boston, MA (US)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 14/336,262

(22) Filed: Jul. 21, 2014

(65) Prior Publication Data
US 2015/0031604 A1 Jan. 29, 2015

Related U.S. Application Data

(60) Provisional application No. 62/015,854, filed on Jun. 23, 2014, provisional application No. 61/858,263, filed on Jul. 25, 2013.

(51) Int. Cl.
C07K 7/64 (2006.01)
C07K 16/46 (2006.01)
A61K 38/12 (2006.01)
A61K 45/06 (2006.01)
C07K 14/47 (2006.01)

(52) U.S. Cl.
CPC . C07K 7/64 (2013.01); A61K 38/12 (2013.01); A61K 45/06 (2013.01); C07K 14/47 (2013.01); C07K 16/461 (2013.01)

(58) Field of Classification Search
None
See application file for complete search history.

(56) References Cited

U.S. PATENT DOCUMENTS

| 5,759,804 | A  | 6/1998  | Godiska et al.  |
|-----------|----|---------|-----------------|
| 6,492,324 | B1 | 12/2002 | Hinuma et al.   |
| 6,555,339 | B1 | 4/2003  | Liaw et al.     |
| 6,774,221 | B1 | 8/2004  | Nishimura et al.|
| 7,635,751 | B2 | 12/2009 | Kitada et al.   |
| 7,736,646 | B2 | 6/2010  | Krieg           |
| 7,947,280 | B2 | 5/2011  | Ashley et al.   |
| 8,673,848 | B2 | 3/2014  | Zecri et al.    |
| 2003/0092618 | A1 | 5/2003 | Hinuma et al.  |
| 2003/0119021 | A1 | 6/2003 | Koster et al.  |
| 2004/0082496 | A1 | 4/2004 | Acton et al.   |
| 2004/0116336 | A1 | 6/2004 | Kitada et al.  |
| 2005/0152836 | A1 | 7/2005 | Ashley et al.  |
| 2006/0045880 | A1 | 3/2006 | Krieg          |
| 2006/0159676 | A1 | 7/2006 | Krieg          |
| 2007/0088244 | A1 | 4/2007 | Miller et al.  |
| 2008/0031871 | A1 | 2/2008 | Allen et al.   |
| 2008/0182779 | A1 | 7/2008 | Ashley et al.  |
| 2011/0008346 | A1 | 1/2011 | Duckers        |
| 2011/0097710 | A1 | 4/2011 | Macrae et al.  |
| 2011/0123534 | A1 | 5/2011 | Duckers        |
| 2011/0305663 | A1 | 12/2011 | Gosselin et al. |
| 2014/0142022 | A1 | 5/2014 | Zecri et al.   |
| 2014/0155315 | A1 | 6/2014 | Zecri et al.   |
| 2014/0275489 | A1 | 9/2014 | Stevis et al.  |
| 2015/0030594 | A1 | 1/2015 | Yuan et al.    |

FOREIGN PATENT DOCUMENTS

EP 1116727 A1 7/2001
EP 2017355 A1 1/2009
(Continued)

OTHER PUBLICATIONS

Pitkin et al (International Union of Basic and Clinical Pharmacology LXXIV Apelin Receptor Nomenclature, Distribution, Pharmacology, and Function Pharmacological Reviews v62 2010 pp. 331-342).*

(Continued)

Primary Examiner — Karlheinz R Skowronek
Assistant Examiner — Ronald Niebauer
(74) Attorney, Agent, or Firm — Sophie Binet Cross

(57) ABSTRACT

The invention provides a cyclic polypeptide of Formula I (SEQ ID NO: 1):

X1-R-X3-X4-L-S-X7-X8-X9-X10-X11-X12-X13    I or an amide, an ester or a salt thereof, or a bioconjugate thereof, wherein X1, X3, X4, X7, X8, X9, X10, X11, X12 and X13 are defined herein. The polypeptides are agonist of the APJ receptor. The invention also relates to a method for manufacturing the polypeptides of the invention or bioconjugates thereof, and their therapeutic uses such as treatment or prevention of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia. The present invention further provides a combination of pharmacologically active agents and a pharmaceutical composition.

23 Claims, No Drawings

(56) References Cited

FOREIGN PATENT DOCUMENTS

| EP | 2330125 A2 | 6/2011 |
|---|---|---|
| RU | 2457216 A | 7/2012 |
| WO | 0190123 A2 | 11/2001 |
| WO | 03063892 A1 | 8/2003 |
| WO | 2005023863 A1 | 3/2005 |
| WO | 2005106493 A1 | 11/2005 |
| WO | 2006009902 A2 | 1/2006 |
| WO | 2006041205 A1 | 4/2006 |
| WO | 2007039184 A2 | 4/2007 |
| WO | 2009033669 A2 | 3/2009 |
| WO | 2009033784 A2 | 3/2009 |
| WO | 2009033819 A2 | 3/2009 |
| WO | 2009075566 A1 | 6/2009 |
| WO | 2010053545 A2 | 5/2010 |
| WO | 2010115874 A1 | 10/2010 |
| WO | 2011056073 A2 | 5/2011 |
| WO | 2011133948 A2 | 10/2011 |
| WO | 2012/125408 A1 | 9/2012 |
| WO | 2013/106437 A1 | 7/2013 |
| WO | 2014/099984 A1 | 6/2014 |
| WO | 2015/013165 A2 | 1/2015 |
| WO | 2015/013167 A2 | 1/2015 |

OTHER PUBLICATIONS

Murza et al., "Elucidation of the Structure-Activity Relationships of Apelin: Influence of Unnatural Amino Acids on Binding, Signaling, and Plasma Stability," Chem Med Chem 7:318-325 (Feb. 2012).

Sidorova et al., "Synthesis and Cardioprotective properties of Apelin-12 and its Structural Analogs," Russian Journal of Bioorganic Chemistry 38(1):40-51 (Jan. 1, 2012).

Murza et al., "Elucidation of the Structure-Activity Relationships of Apelin: Influence of Unnatural Amino Acids on Binding, Signaling and Plasma Stability," Journal of Peptide Science 18(1):S104 (Sep. 2012).

Lee et al., "Modification of the Terminal Residue of Apelin-13 Antagonizes Its Hypotensive Action," Endocrinology 146 (1):231-236 (Oct. 14, 2004).

Francia et al., "The Apelin/APJ System From Vascular Biology to Heart Failure," High Blood Press Cardiovasc Prev 13 (4):159-162 (Oct. 22, 2006).

Zeng et al., "Effects and mechanisms of apelin-13 on ischemia/reperfusion injury in rat heart," Chinese Pharmacological Bulletin 23(1):82-85 (Jan. 2007).

Simpkin et al., "Apelin-13 and apelin-36 exhibit direct cardio protective activity against ischemia reperfusion injury," Basic Research in Cardiology 102(6):518-528 (Nov. 2007).

Zhang et al., "The Effect of Apelin-13 on Ischemia-Induced Cardiomyocyte Apoptosis in Acute Myocardial Ischemia Rats," Chinese Journal of Arteriosclerosis 2008-2009.

Fukase et al., "Synthetic Study on Peptide Antiobiotic Nisin. V. Total Synthesis of Nisin," Bull. Chem. Soc. Jpn. 65:2227-2240 (1992).

Rastaldo et al., "Apelin-13 limits infarct size and improves cardiac postischemic mechanical recovery only if given after ischemia" American Journal of Physiology—Heart and Circulatory Physiology 300(6):H2308-H2315 (Jun. 2011).

Charles, Christopher, "Update on apelin peptides as putative targets for cardiovascular drug discovery" Expert Opinion on Drug Discovery 6(6):633-644 , (Jun. 2011).

Tycinska et al., "Apelin in acute myocardial infarction and heart failure induced by ischemia," Clinica Chimica Acta 413: 406-410 (Nov. 25, 2011).

Dowd et al., "A human gene that shows identity with the gene encoding the angiotensin receptor is located on chromosome 11," Gene 136:355-360 (1993).

Habata et al. "Apelin, the natural ligand of the orphan receptor APJ, is abundantly secreted in the colostrum," Biochimica et Biophysica Acta 1452:25-35 (1999).

Hamada et al., "Evaluation of novel cyclic analogues of apelin," International Journal of molecular medicine 22:547-552 (2008).

Bernardes et al., "From Disulfide- to Thioether-Linked Glycoproteins," Angew, Chem. Int. Ed 47:2244-2247 (2008).

Ranganathan et al., "Triply bridged (1,3,5) cyclophanes from cystine and lanthionine linkers—a comparison," Tetrahedron 66:3923-3929 (2010).

Japp et al., "Vascular effects of apelin in vivo in man," Journal of the american college of cardiology 52:908-13 (2008).

Medhurst et al., "Pharmacological and immunohistochemical characterization of the APJ receptor and its endogenous ligand apelin," Journal of neurochemistry 84:1162-1172 (2003).

Macaluso and Glen, "Exploring the 'RPRL' Motif of apelin-13 through molecular simulation and biological evaluation of cyclic peptide analogues," ChemMedChem 5:1247-1253 (2010).

Macaluso et al., "Discovery of competitive apelin receptor (APJ) antagonist," ChemMedChem 6:1017-1023 (2011).

Pisarenko et al., Effects of structural analogues of apelin-12 in acute myocardial infarction in rats, Journal of Pharmacology and Pharmcotherapeutics, Jul.-Sep. 2013, vol. 4, Issue 3, pp. 198-203.

Pisarenko. et. al, Apelin-12 and its structural analog enhance antioxidant defense in experimental myocardial ischemia and reperfusion, Mol. Cell Biochem (2014), 391:241-250.

Margathe et al., Structure-Activity Relationship Studies toward the Discovery of Selective Apelin Receptor Agonists, Journal of Medicinal Chemistry (2014), vol. 57, pp. 2908-2919.

Jia et al., Cardiovascular effects of a PEGylated apelin, Elsevier Inc., Peptides 38 (2012), pp. 181-188.

IUPAC Codes for Amino Acids, Amino Acid Codes, thinkpeptides, http://thinkpeptides.com/extras.html, (2015).

\* cited by examiner

SEQUENCE LISTING

```
<160> NUMBER OF SEQ ID NOS: 78

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ala, pyroGlu, Cys, D-Cys, homoCys,
      D-homoCys or absent
<220> FEATURE:
<221> NAME/KEY: MOD_RES
<222> LOCATION: (3)..(3)
<223> OTHER INFORMATION: Pro, Cys, D-Cys, homoCys or D-homoCys
<220> FEATURE:
<221> NAME/KEY: MOD_RES
<222> LOCATION: (4)..(4)
<223> OTHER INFORMATION: Arg, Cys, D-Cys, homoCys or D-homoCys
<220> FEATURE:
<221> NAME/KEY: MOD_RES
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: misc_feature
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Nle, Met or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: (N-Me)Phe, Phe, D-Phe, D-Ala, D-Tyr, Nal or
      absent
```

<400> SEQUENCE: 1

Xaa Arg Xaa Xaa Leu Ser Xaa Xaa Xaa Pro Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ala, pyroGlu or absent
<220> FEATURE:
<221> NAME/KEY: MOD_RES
<222> LOCATION: (4)..(4)
<223> OTHER INFORMATION: Cys, D-Cys, homoCys or D-homoCys
<220> FEATURE:
<221> NAME/KEY: MOD_RES
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: misc_feature
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Met, Nle or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: Phe, (N-Me)Phe, D-Phe, D-Ala, D-Tyr, Nal or
      absent

<400> SEQUENCE: 2

Xaa Arg Pro Xaa Leu Ser Xaa Xaa Xaa Pro Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: misc_feature
<222> LOCATION: (1)..(1)
<223> OTHER INFORMATION: May or may not be present
<220> FEATURE:
<221> NAME/KEY: MOD_RES
<222> LOCATION: (4)..(4)
<223> OTHER INFORMATION: Cys, D-Cys, homoCys or D-homoCys
<220> FEATURE:
<221> NAME/KEY: MOD_RES

```
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: misc_feature
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Nle or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: Phe, (N-Me)Phe, D-Phe, D-Ala, D-Tyr, Nal or
      absent

<400> SEQUENCE: 3

Glu Arg Pro Xaa Leu Ser Xaa Xaa Xaa Pro Xaa Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys, D-Cys, homoCys or D-homoCys
<220> FEATURE:
<221> NAME/KEY: MOD_RES
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: misc_feature
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Nle, Met or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: (N-Me)Phe, Phe, D-Phe, D-Ala, D-Tyr, Nal or
      absent

<400> SEQUENCE: 4

Xaa Arg Pro Arg Leu Ser Xaa Xaa Xaa Pro Xaa Xaa Xaa
1               5                   10
```

```
<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ala, pyroGlu or absent
<220> FEATURE:
<221> NAME/KEY: MOD_RES
<222> LOCATION: (3)..(3)
<223> OTHER INFORMATION: Cys, D-Cys, homoCys or D-homoCys
<220> FEATURE:
<221> NAME/KEY: MOD_RES
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: misc_feature
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Nle, Met or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: (N-Me)Phe, Phe, D-Phe, D-Ala, D-Tyr, Nal or
      absent

<400> SEQUENCE: 5

Xaa Arg Xaa Arg Leu Ser Xaa Xaa Xaa Pro Xaa Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: misc_feature
<222> LOCATION: (1)..(1)
<223> OTHER INFORMATION: May or may not be present
<220> FEATURE:
<221> NAME/KEY: MOD_RES
<222> LOCATION: (3)..(3)
<223> OTHER INFORMATION: Cys, D-Cys, homoCys or D-homoCys
<220> FEATURE:
<221> NAME/KEY: MOD_RES
<222> LOCATION: (7)..(7)
<223> OTHER INFORMATION: Cys, D-Cys, homoCys or D-homoCys
<220> FEATURE:
<221> NAME/KEY: MOD_RES
<222> LOCATION: (8)..(8)
```

```
<223> OTHER INFORMATION: Lys or Phe
<220> FEATURE:
<221> NAME/KEY: MOD_RES
<222> LOCATION: (9)..(9)
<223> OTHER INFORMATION: Gly, Ala, D-Ala or absent
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: D-Nle, Nle or D-Phe
<220> FEATURE:
<221> NAME/KEY: MOD_RES
<222> LOCATION: (12)..(12)
<223> OTHER INFORMATION: Pro, D-Phe, D-Ala, D-Nva, D-Abu or absent
<220> FEATURE:
<221> NAME/KEY: MOD_RES
<222> LOCATION: (13)..(13)
<223> OTHER INFORMATION: (N-Me)Phe, Phe, D-Phe, D-Ala, D-Tyr, Nal or
      absent

<400> SEQUENCE: 6

Glu Arg Xaa Arg Leu Ser Xaa Xaa Xaa Pro Xaa Xaa Xaa
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This sequence may encompass 1-3 "Gly Gly Gly
      Gly Ser" repeating units, wherein some positions may be absent

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Arg Pro Cys Leu Ser Cys Lys Gly Pro Met Pro Phe
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Arg Pro Arg Leu Ser Cys Lys Gly Pro Met Pro Phe
1               5                   10

<210> SEQ ID NO 10
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Gln Arg Cys Arg Leu Ser Cys Lys Gly Pro Met Pro Phe
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 1-3 "Gly Gly Gly Gly"
      repeating units, wherein some positions may be absent

<400> SEQUENCE: 11

Gly Gly Gly Gly Gly Gly Gly Gly Gly Gly Gly Gly Leu Pro Glu Thr
1               5                   10                  15

Leu

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser
1               5

<210> SEQ ID NO 15
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Gly Gly Gly Gly Leu Glu Thr Gly Gly Leu Glu Val Leu Phe Gln Gly
1               5                   10                  15

Pro

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Leu Glu Val Leu Phe Gln Gly Pro
1               5                   10

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 1-3 "Gly Gly Gly Gly"
      repeating units, wherein some positions may be absent

<400> SEQUENCE: 17

Gly Gly Gly Gly Gly Gly Gly Gly Gly Gly Gly Gly Leu Pro Glu Thr
1               5                   10                  15

Gly Gly Leu Glu Val Leu Phe Gln Gly Pro
            20                  25

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Trp Phe Lys Ala Phe Tyr Asp Lys Val Ala Glu Lys Phe Lys Glu
1               5                   10                  15

Ala Phe

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 19

Cys Arg Pro Arg Leu Ser Cys Lys Gly Pro Leu Pro Phe
1               5                   10
```

```
<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 20

Cys Arg Pro Arg Leu Ser Cys Lys Gly Pro Leu Pro
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: (N-Me)Phe

<400> SEQUENCE: 21

Cys Arg Pro Arg Leu Ser Cys Lys Gly Pro Leu Pro Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 22

Cys Arg Pro Arg Leu Ser Cys Lys Gly Pro Leu Pro
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: Nal

<400> SEQUENCE: 23

Cys Arg Pro Arg Leu Ser Cys Lys Gly Pro Leu Pro Ala
```

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: Nle

<400> SEQUENCE: 24

Cys Arg Pro Arg Leu Ser Cys Lys Gly Pro Leu Pro Phe
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: homoCys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: Nle

<400> SEQUENCE: 25

Cys Arg Pro Arg Leu Ser Cys Lys Gly Pro Leu Pro Phe
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Ala

<400> SEQUENCE: 26

Cys Arg Pro Arg Leu Ser Cys Lys Gly Pro Leu Pro Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (11)..(11)
<223> OTHER INFORMATION: Nle

<400> SEQUENCE: 27

Cys Arg Pro Arg Leu Ser Cys Lys Gly Pro Leu Pro
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: D-Phe

<400> SEQUENCE: 28

Cys Arg Pro Arg Leu Ser Cys Lys Gly Pro Leu Pro Phe
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Nle

<400> SEQUENCE: 29

Cys Arg Pro Arg Leu Ser Cys Lys Gly Pro Leu
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (11)..(11)
<223> OTHER INFORMATION: Nle

<400> SEQUENCE: 30

Cys Arg Pro Arg Leu Ser Cys Lys Gly Pro Leu Pro Phe
1               5                   10

<210> SEQ ID NO 31
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: Nle

<400> SEQUENCE: 31

Cys Arg Pro Arg Leu Ser Cys Lys Gly Pro Leu Pro Phe
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (7)..(7)
<223> OTHER INFORMATION: D-Cys
<220> FEATURE:
<221> NAME/KEY: MOD_RES
<222> LOCATION: (11)..(11)
<223> OTHER INFORMATION: Nle

<400> SEQUENCE: 32

Cys Arg Pro Arg Leu Ser Cys Lys Gly Pro Leu Pro Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Cys
<220> FEATURE:
<221> NAME/KEY: MOD_RES
<222> LOCATION: (11)..(11)
<223> OTHER INFORMATION: Nle

<400> SEQUENCE: 33

Cys Arg Pro Arg Leu Ser Cys Lys Gly Pro Leu Pro Phe
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: D-homoCys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: Nle

<400> SEQUENCE: 34

Cys Arg Pro Arg Leu Ser Cys Lys Gly Pro Leu Pro Phe
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-homoCys
<220> FEATURE:
<221> NAME/KEY: MOD_RES
<222> LOCATION: (7)..(7)
<223> OTHER INFORMATION: D-homoCys
<220> FEATURE:
<221> NAME/KEY: MOD_RES
<222> LOCATION: (11)..(11)
<223> OTHER INFORMATION: Nle

<400> SEQUENCE: 35

Cys Arg Pro Arg Leu Ser Cys Lys Gly Pro Leu Pro Phe
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-homoCys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: D-Phe
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 36

Cys Arg Pro Arg Leu Ser Cys Lys Gly Pro Phe Ala Phe
1               5                   10

<210> SEQ ID NO 37
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 37

Cys Arg Pro Arg Leu Ser Cys Lys Gly Pro Leu Ala Phe
1               5                  10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle

<400> SEQUENCE: 38

Glu Arg Cys Arg Leu Ser Cys Lys Gly Pro Leu Pro Phe
1               5                  10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 39
```

Glu Arg Cys Arg Leu Ser Cys Lys Gly Pro Leu Ala Phe
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 40

Glu Arg Cys Arg Leu Ser Cys Phe Gly Pro Leu Ala Phe
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 41

Glu Arg Cys Arg Leu Ser Cys Lys Ala Pro Leu Ala Phe
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu

```
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 42

Glu Arg Cys Arg Leu Ser Cys Lys Ala Pro Leu Ala Phe
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle

<400> SEQUENCE: 43

Glu Arg Cys Arg Leu Ser Cys Lys Gly Pro Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (7)..(7)
<223> OTHER INFORMATION: D-homoCys
<220> FEATURE:
<221> NAME/KEY: MOD_RES
<222> LOCATION: (11)..(11)
<223> OTHER INFORMATION: D-Phe
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 44

Glu Arg Cys Arg Leu Ser Cys Lys Gly Pro Phe Ala Phe
1               5                   10

<210> SEQ ID NO 45
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (3)..(3)
<223> OTHER INFORMATION: D-Cys
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Abu
<220> FEATURE:
<221> NAME/KEY: MOD_RES
<222> LOCATION: (13)..(13)
<223> OTHER INFORMATION: D-Phe

<400> SEQUENCE: 45

Glu Arg Cys Arg Leu Ser Cys Lys Gly Pro Leu Xaa Phe
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle

<400> SEQUENCE: 46

Glu Arg Pro Cys Leu Ser Cys Lys Gly Pro Leu Pro Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (13)..(13)
<223> OTHER INFORMATION: (N-Me)Phe

<400> SEQUENCE: 47

Glu Arg Pro Cys Leu Ser Cys Lys Gly Pro Leu Pro Phe
```

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle

<400> SEQUENCE: 48

Glu Arg Pro Cys Leu Ser Cys Lys Gly Pro Leu Pro
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: Nle

<400> SEQUENCE: 49

Glu Arg Pro Cys Leu Ser Cys Lys Gly Pro Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle

<400> SEQUENCE: 50

Glu Arg Pro Cys Leu Ser Cys Lys Gly Pro Leu
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: pyroGlu
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 51

Glu Arg Pro Cys Leu Ser Cys Lys Gly Pro Leu Ala Phe
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Phe

<400> SEQUENCE: 52

Glu Arg Pro Cys Leu Ser Cys Lys Gly Pro Leu Phe
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 53

Glu Arg Pro Cys Leu Ser Cys Phe Gly Pro Leu Ala Phe
1               5                   10

<210> SEQ ID NO 54
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-Nle
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: D-Phe

<400> SEQUENCE: 54

Arg Pro Cys Leu Ser Cys Lys Leu Ala Phe
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (4)..(4)
<223> OTHER INFORMATION: homoCys
<220> FEATURE:
<221> NAME/KEY: MOD_RES
<222> LOCATION: (11)..(11)
<223> OTHER INFORMATION: D-Phe
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 55

Glu Arg Pro Cys Leu Ser Cys Lys Gly Pro Phe Ala Phe
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (4)..(4)
<223> OTHER INFORMATION: D-Cys
<220> FEATURE:
<221> NAME/KEY: MOD_RES
<222> LOCATION: (7)..(7)
<223> OTHER INFORMATION: D-homoCys
<220> FEATURE:
<221> NAME/KEY: MOD_RES
<222> LOCATION: (11)..(11)
```

```
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Tyr

<400> SEQUENCE: 56

Glu Arg Pro Cys Leu Ser Cys Lys Gly Pro Leu Ala Tyr
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (4)..(4)
<223> OTHER INFORMATION: D-homoCys
<220> FEATURE:
<221> NAME/KEY: MOD_RES
<222> LOCATION: (7)..(7)
<223> OTHER INFORMATION: homoCys
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Nva
<220> FEATURE:
<221> NAME/KEY: MOD_RES
<222> LOCATION: (13)..(13)
<223> OTHER INFORMATION: D-Phe

<400> SEQUENCE: 57

Glu Arg Pro Cys Leu Ser Cys Lys Gly Pro Leu Val Phe
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(Trt)
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
```

-continued

```
<222> LOCATION: (7)..(7)
<223> OTHER INFORMATION: Cys(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle

<400> SEQUENCE: 58

Cys Arg Pro Arg Leu Ser Cys Lys Gly Pro Leu Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys(Trt)
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
<222> LOCATION: (7)..(7)
<223> OTHER INFORMATION: Cys(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: Nle

<400> SEQUENCE: 59

Cys Arg Pro Arg Leu Ser Cys Lys Gly Pro Leu Pro Phe
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (3)..(3)
<223> OTHER INFORMATION: Cys(Trt)
<220> FEATURE:
```

```
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
<222> LOCATION: (7)..(7)
<223> OTHER INFORMATION: Cys(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: D-Nle
<220> FEATURE:
<221> NAME/KEY: MOD_RES
<222> LOCATION: (12)..(12)
<223> OTHER INFORMATION: D-Ala
<220> FEATURE:
<221> NAME/KEY: MOD_RES
<222> LOCATION: (13)..(13)
<223> OTHER INFORMATION: D-Phe

<400> SEQUENCE: 60

Glu Arg Cys Arg Leu Ser Cys Lys Gly Pro Leu Ala Phe
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (4)..(4)
<223> OTHER INFORMATION: Cys(Trt)
<220> FEATURE:
<221> NAME/KEY: MOD_RES
<222> LOCATION: (6)..(6)
<223> OTHER INFORMATION: Ser(tBu)
<220> FEATURE:
<221> NAME/KEY: MOD_RES
<222> LOCATION: (7)..(7)
<223> OTHER INFORMATION: Cys(Trt)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (11)..(11)
<223> OTHER INFORMATION: D-Nle

<400> SEQUENCE: 61

Glu Arg Pro Cys Leu Ser Cys Lys Gly Pro Leu
1               5                   10

<210> SEQ ID NO 62
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (4)..(4)
<223> OTHER INFORMATION: O2Oc
<220> FEATURE:
<221> NAME/KEY: MOD_RES
<222> LOCATION: (15)..(15)
<223> OTHER INFORMATION: D-Nle

<400> SEQUENCE: 62

Xaa Xaa Xaa Xaa Gln Arg Pro Cys Leu Ser Cys Lys Gly Pro Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: O2Oc
<220> FEATURE:
<221> NAME/KEY: MOD_RES
<222> LOCATION: (2)..(2)
<223> OTHER INFORMATION: O2Oc
<220> FEATURE:
<221> NAME/KEY: MOD_RES
<222> LOCATION: (3)..(3)
<223> OTHER INFORMATION: O2Oc
<220> FEATURE:
<221> NAME/KEY: MOD_RES
<222> LOCATION: (4)..(4)
<223> OTHER INFORMATION: O2Oc
<220> FEATURE:
<221> NAME/KEY: MOD_RES
<222> LOCATION: (6)..(6)
<223> OTHER INFORMATION: Arg(Pbf)
<220> FEATURE:
<221> NAME/KEY: MOD_RES
<222> LOCATION: (8)..(8)
<223> OTHER INFORMATION: Cys(Trt)
<220> FEATURE:
<221> NAME/KEY: MOD_RES
<222> LOCATION: (10)..(10)
<223> OTHER INFORMATION: Ser(tBu)
<220> FEATURE:
<221> NAME/KEY: MOD_RES
<222> LOCATION: (11)..(11)
<223> OTHER INFORMATION: Cys(Trt)
<220> FEATURE:
<221> NAME/KEY: MOD_RES
<222> LOCATION: (12)..(12)
<223> OTHER INFORMATION: Lys(tBoc)
<220> FEATURE:
<221> NAME/KEY: MOD_RES
<222> LOCATION: (15)..(15)
<223> OTHER INFORMATION: D-Nle
```

<400> SEQUENCE: 63

Xaa Xaa Xaa Xaa Gln Arg Pro Cys Leu Ser Cys Lys Gly Pro Leu
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pyroGlu
<220> FEATURE:
<221> NAME/KEY: MOD_RES
<222> LOCATION: (8)..(8)
<223> OTHER INFORMATION: N6-[[(1-alpha,8-alpha,9-alpha)-bicyclo[6.1.0]
      non-4-yn-9-ylmethoxy]carbonyl-Lys
<220> FEATURE:
<221> NAME/KEY: MOD_RES
<222> LOCATION: (11)..(11)
<223> OTHER INFORMATION: D-Nle

<400> SEQUENCE: 64

Glu Arg Pro Cys Leu Ser Cys Lys Gly Pro Leu
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: D-Nle

<400> SEQUENCE: 65

Ala His Gln Arg Pro Cys Leu Ser Cys Lys Gly Pro Leu
1               5                   10

<210> SEQ ID NO 66
<211> LENGTH: 766
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gctagccacc atggaaactg acaccctgct gctgtgggtc ctgctgctgt gggtgcctgg      60
cagcactggc gctcatgata agacacacac atgcccccct tgtccagcac cagaggcagc     120
tggaggacca gcgtgttcc tgtttccacc caagcctaaa gacacactga tgatctcaag      180
gaccccagaa gtcacatgcg tggtcgtgga cgtgtctcac gaggacccg aagtcaagtt      240 caactggtac gtggatggcg tcgaggtgca taatgctaag accaaacccc gagaggaaca     300
gtacaacagc acctatcggg tcgtgtccgt cctgacagtg ctgcaccagg attggctgaa     360
cggcaaagag tataagtgca aagtgagtaa taaggctctg cctgcaccaa tcgagaaaac     420
aatttctaag gctaagggc agccaagaga accccaggtg tacactctgc ctccatctag     480
ggaggaaatg acaaagaacc aggtcagtct gacttgtctg gtgaaaggct tctacccctc     540

```
cgacatcgca gtggagtggg aatctaatgg ccagcctgaa acaattaca agaccacacc    600 ccctgtgctg gactccgatg ggtctttctt tctgtattct aagctgaccg tggataaaag   660
tcggtggcag cagggaaacg tcttctcatg cagcgtgatg cacgaggccc tgcacaatca   720
ttacacacag aagtccctgt ctctgagtcc aggcaaatga gaattc                 766
```

<210> SEQ ID NO 67
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Glu Thr Asp Thr Leu Leu Leu Trp Val Leu Leu Leu Trp Val Pro
1               5                   10                  15

Gly Ser Thr Gly Ala His Asp Lys Thr His Thr Cys Pro Pro Cys Pro
            20                  25                  30

Ala Glu Ala Ala Gly Gly Pro Ser Val Phe Leu Phe Pro Pro Lys Pro
        35                  40                  45

Lys Asp Thr Leu Met Ile Ser Arg Thr Glu Val Thr Cys Val Val Val
50                  55                  60

Asp Val Ser His Glu Asp Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Azido-Lys

```
<220> FEATURE:
<221> NAME/KEY: MOD_RES
<222> LOCATION: (17)..(17)
<223> OTHER INFORMATION: D-Nle

<400> SEQUENCE: 68

Lys Gly Gly Gly Gly Ser Gln Arg Pro Cys Leu Ser Cys Lys Gly Pro
1               5                   10                  15

Leu

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Leu Pro Glu Thr Gly Gly Leu Glu Val Leu Phe
1               5                   10                  15

Gln Gly Pro

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: D-Nle

<400> SEQUENCE: 70

Gly Gly Gly Gly Gly Gln Arg Pro Cys Leu Ser Cys Lys Gly Pro Leu
1               5                   10                  15

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: D-Nle

<400> SEQUENCE: 71

Gly Gly Gly Gly Ser Leu Pro Glu Thr Gly Gly Gly Gly Gln Arg
1               5                   10                  15

Pro Cys Leu Ser Cys Lys Gly Pro Leu
            20                  25

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
```

<400> SEQUENCE: 72

Leu Pro Xaa Thr Gly
1               5

<210> SEQ ID NO 73
<211> LENGTH: 817
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | | | | | | |
|---|---|---|---|---|---|---|
| gctagccacc | atggaaaccg | acaccctgct | gctgtgggtg | ctgctgctgt | gggtgccagg | 60 |
| cagcaccggc | gataagaccc | acacctgtcc | tccctgtcct | gccccctgaag | ctgctggcgg | 120 |
| ccctagcgtg | ttcctgttcc | ccccaaagcc | caaggacacc | ctgatgatca | gccggacccc | 180 |
| cgaagtgacc | tgcgtggtgg | tggatgtgtc | ccacgaggac | cctgaagtga | agttcaattg | 240 |
| gtacgtggac | ggcgtggaag | tgcacaacgc | caagaccaag | cccagagagg | aacagtacaa | 300 |
| cagcacctac | cgggtggtgt | ccgtgctgac | cgtgctgcac | caggactggc | tgaacggcaa | 360 |
| agagtacaag | tgcaaggtgt | ccaacaaggc | cctgccagcc | cccatcgaga | aaaccatcag | 420 |
| caaggccaag | ggccagcccc | gcgaaccccca | ggtgtacaca | ctgcccccta | gccgggaaga | 480 |
| gatgaccaag | aaccaggtgt | ccctgacctg | tctcgtgaag | ggcttctacc | cctccgatat | 540 |
| cgccgtggaa | tgggagagca | acggccagcc | cgagaacaac | tacaagacca | cccccccctgt | 600 |
| gctggacagc | gacggctcat | tcttcctgta | cagcaagctg | acagtggaca | agagccggtg | 660 |
| gcagcagggc | aacgtgttca | gctgcagcgt | gatgcacgag | gccctgcaca | accactacac | 720 |
| ccagaagtcc | ctgagcctga | gccctggaaa | aggcggcgga | ggctctctgc | tgaaacagg | 780 |
| cggactggaa | gtgctgttcc | agggccccta | agaattc | | | 817 |

<210> SEQ ID NO 74
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Glu Val Thr Cys Val Val Val Asp Val
    50                  55                  60

Ser His Glu Asp Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

```
Ile Glu Lys Thr Ile Ser Lys Ala Lys Gly Gln Pro Arg Glu Pro Gln
    130                 135                 140
Val Tyr Thr Leu Pro Pro Ser Arg Glu Glu Met Thr Lys Asn Gln Val
145                 150                 155                 160
Ser Leu Thr Cys Leu Val Lys Gly Phe Tyr Pro Ser Asp Ile Ala Val
                165                 170                 175
Glu Trp Glu Ser Asn Gly Gln Glu Asn Asn Tyr Lys Thr Thr Pro Pro
            180                 185                 190
Val Leu Asp Ser Asp Gly Ser Phe Phe Leu Tyr Ser Lys Leu Thr Val
        195                 200                 205
Asp Lys Ser Arg Trp Gln Gln Gly Asn Val Phe Ser Cys Ser Val Met
    210                 215                 220
His Glu Ala Leu His Asn His Tyr Thr Gln Lys Ser Leu Ser Leu Ser
225                 230                 235                 240
Pro Gly Lys Gly Gly Gly Gly Ser Leu Glu Thr Gly Gly Leu Glu Val
                245                 250                 255
Leu Phe Gln Gly Pro
            260

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (7)..(7)
<223> OTHER INFORMATION: Arg(Pbf)
<220> FEATURE:
<221> NAME/KEY: MOD_RES
<222> LOCATION: (9)..(9)
<223> OTHER INFORMATION: Cys(Trt)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Cys(Trt)
<220> FEATURE:
<221> NAME/KEY: MOD_RES
<222> LOCATION: (13)..(13)
<223> OTHER INFORMATION: Lys(Boc)
<220> FEATURE:
<221> NAME/KEY: MOD_RES
<222> LOCATION: (16)..(16)
<223> OTHER INFORMATION: D-Nle

<400> SEQUENCE: 75

Gly Gly Gly Gly Gly Gln Arg Pro Cys Leu Ser Cys Lys Gly Pro Leu
1               5                   10                  15

<210> SEQ ID NO 76
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (267)..(267)
<223> OTHER INFORMATION: D-Nle

<400> SEQUENCE: 76
```

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Glu Val Thr Cys Val Val Val Asp Val
    50                  55                  60

Ser His Glu Asp Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Gly Gly Gly Gly Ser Leu Glu Thr Gly Gly Gly Gly Gly
                245                 250                 255

Gln Arg Pro Cys Leu Ser Cys Lys Gly Pro Leu
            260                 265
```

```
<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

```
Leu Ser Leu Ser Pro Gly Lys Gly Gly Gly Gly Ser Leu Glu Thr Gly
1               5                   10                  15

Gly Gly Gly Gly
            20
```

```
<210> SEQ ID NO 78
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: D-Nle

<400> SEQUENCE: 78

Gln Arg Pro Cys Leu Ser Cys Lys Gly Pro Leu
1               5                   10
```

CYCLIC POLYPEPTIDES FOR THE TREATMENT OF HEART FAILURE

This application claims benefit under 35 U.S.C. §119(e) of U.S. Provisional Application No. 61/858,263, filed Jul. 25, 2013; and U.S. Provisional Application No. 62/015,854 filed Jun. 23, 2014; the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 29, 2014, is named PAT055418-US-NP_SL.txt and is 44,387 bytes in size.

FIELD OF THE INVENTION

The invention relates to novel compositions comprising modified peptide and polypeptide sequences designed to treat cardiovascular disease in subjects to whom they are administered, and which exhibit greater resistance to degradation, and equivalent or greater bioactivity than their wild type counterparts. The invention also relates to methods of making said compositions and using said compositions as pharmaceutically active agents to treat cardiovascular disease.

BACKGROUND OF THE INVENTION

The incidence of heart failure in the Western world is approximately 1/100 adults after 65 yrs of age. The most common pathology is a chronic deficit in cardiac contractility and, thereby, cardiac output, i.e., the effective volume of blood expelled by either ventricle of the heart over time. Patients with chronic heart failure can have acute episodes of decompensation, i.e., failure of the heart to maintain adequate blood circulation, where cardiac contractility declines further. There are ~500K hospitalizations per year for "acute decompensated heart failure" (ADHF) in the USA alone.

Current therapies for ADHF include diuretics, vasodilators, and inotropes, which directly increase cardiac contractility. Current intravenous inotropes (dobutamine, dopamine, milrinone, levosimendan) are used in the acute setting, despite their association with adverse events such as arrhythmia and increased long-term mortality. These liabilities have prevented their application in chronic heart failure. Digoxin is an oral inotrope, but is limited by a narrow therapeutic index, increased arrhythmogenic potential and contraindication in renal insufficiency.

A therapy for heart failure that increases cardiac contractility without arrhythmogenic or mortality liabilities is urgently needed for ADHF, but could also address the enormous unmet medical need in chronic heart failure.

Apelin is the endogenous ligand for the previously orphan G-protein-coupled receptor (GPCR), APJ, also referred to as apelin receptor, angiotension-like-1 receptor, angiotension II-like-1 receptor, and the like. The apelin/APJ pathway is widely expressed in the cardiovascular system and apelin has shown major beneficial cardiovascular effects in preclinical models. Acute apelin administration in humans causes peripheral and coronary vasodilatation and increases cardiac output (Circulation. 2010; 121:1818-1827). As a result, APJ agonism is emerging as an important therapeutic target for patients with heart failure. Activation of the apelin receptor APJ is thought to increase cardiac contractility and provide cardioprotection, without the liabilities of current therapies.

However, the native apelins exhibit a very short half life and duration of action in vivo. The very short half life is a recognized major difficulty with the delivery of such therapeutic endogenous peptides due to rapid serum clearance and proteolytic degradation via the action of peptidases.

One way which has been currently used to overcome this disadvantage is to administer large dosage of therapeutic peptide of interest to the patient so that even if some therapeutic peptide is degraded, enough remains to be therapeutically effective. However, this method is uncomfortable to patients. Since most therapeutic peptides cannot be administered orally, the therapeutic peptide would have to be either constantly infused, frequently infused by intravenous injection or administered frequently by the inconvenient route of subcutaneous injections. The need for frequent administration also results in many potential peptide therapeutics having an unacceptable high projected cost of treatment. The presence of large amounts of degraded peptide may also generate undesired side effects.

Discomfort in administration and high costs are two reasons why most therapeutic peptides with attractive bioactivity profiles may not be developed as drug candidates.

Therefore, one approach to prolong half-life of peptides is to modify the therapeutic peptides in such a way that their degradation is slowed down while still maintaining biological activity.

It is therefore desirable to identify peptides and polypeptides that mimic the function of apelin, but have increased half-life and demonstrate equivalent or greater bioactivity than the naturally occurring apelin. Furthermore, it is desirable to identify apelin analog peptides and polypeptides which exhibit increased conformational constraints, i.e., the ability to achieve and maintain an active conformational state such that the peptides and polypeptides can interact with their receptors and/or other pathway targets without the need for additional folded or repositioning. Additional approaches includes reducing the rate of clearance by conjugating the peptides to molecules that prevent their elimination through kidney.

There is thus a need for modified therapeutic peptides with increased half-life in order to provide longer duration of action in vivo, while maintaining low toxicity yet retaining the therapeutic advantages of the modified peptides.

SUMMARY OF THE INVENTION

This invention is directed to overcoming the problem of peptide degradation in the body by modifying the therapeutic peptide or polypeptide of interest, i.e. APJ agonists.

The aim of the present invention is to provide novel peptides and polypeptides or bioconjugate thereof, which are useful as APJ agonists, and which also possess at least one of the following improvements over wild type apelin and other known apelin analogs: increased half-life; greater immunity to degradation upon administration and/or upon solubilization; and increased conformational constraints, all while exhibiting the same or greater biological activity as wild type apelin. The peptides and polypeptides of this invention, or bioconjugates thereof, are thus particularly useful for the treatment or prevention of cardiovascular diseases such as heart failure, disorders and conditions associated with heart failure, and disorders and conditions responsive to the activation of APJ receptor activity.

In one embodiment, the peptides and polypeptides of the invention, or bioconjugates thereof, are particularly useful for the treatment or prevention of a disorder or condition associated with heart failure, or a disorder responsive to the activation (or agonism) of the APJ receptor activity. In another embodiment, the peptides and polypeptides of the invention, or bioconjugates thereof, are useful in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

The invention pertains to the peptides and polypeptides, or bioconjugates thereof, pharmaceutical compositions, and methods of manufacture and use thereof, as described herein. Examples of peptides and polypeptides of the invention include the peptides and polypeptides according to any one of Formulae I to IV, or an amide, an ester or a salt thereof, as well as any peptides or polypeptides specifically listed herein, and bioconjugates thereof, including but not limited to the experimental examples.

The invention therefore provides a peptide or a polypeptide formula (I) (SEQ ID NO: 1):

$$X1-R-X3-X4-L-S-X7-X8-X9-X10-X11-X12-X13 \qquad I$$

wherein:
X1 is the N-terminus of the polypeptide and is either absent or is Q, A or pE or X1 is selected from C, c, hC, D-hC; wherein the side chain of C, c, hC or D-hC form a disulfide bond with the side chain of X7;
X3 is P or X3 is selected from C, c, hC and D-hC; wherein the side chain of C, c, hC or D-hC forms a disulfide bond with the side chain of X7;
X4 is R or X4 is selected from C, c, hC and D-hC; wherein the side chain of C, c, hC or D-hC forms a disulfide bond with the side chain of X7;
wherein only one of X1, X3 and X4 is a sulfur contain aminoacid selected from C, c, hC and D-hC;
X7 is C, c, hC or D-hC; and the side chain of X7 forms a disulfide bond with the side chain of C, c, hC or D-hC of either X1, X3 or X4;
X8 is K or F;
X9 is G, A, a or absent;
X10 is P or absent;
X11 is D-Nle, Nle, M or f; and
X12 is absent or P, f, a, D-Nva or D-Abu;
X13 is the C-terminus and is absent or is selected from (N-Me)F, F, f, a, y and Nal; wherein:
Nle is L-norleucine;
D-Nle is D-norleucine;
D-hC is D-homocysteine
hC is L-homocysteine;
Nal is L-naphathaline;
D-Nva is D-norvaline;
D-Abu is D-2-aminobutyric acid;
pE is L-pyroglutamic acid;
or an amide, an ester or a salt of the polypeptide; or a polypeptide substantially equivalent thereof.

As further explained herein, the art-recognized three letter or one letter abbreviations are used to represent amino acid residues that constitute the peptides and polypeptides of the invention. When the one letter abbreviation is a capital letter, it refers to the L-amino acid. When the one letter abbreviation is a lower case letter, it refers to the D-amino acid. Alternatively, a D-amino acid can be represented with a D-letter in front of the abbreviation letter(s). i.e., when preceded with "D," the amino acid is a D-amino acid.

Any of the above-listed amino acid residues of Formula I, or its related formulae described herein, e.g., Formulae I to IV, may be substituted in a conservative fashion, provided the peptide or polypeptide of the invention still retains functional activity and structural properties (e.g., half-life extension, protection from degradation, conformational constraint). Principle and examples of permissible conservative amino acid substitutions are further explained herein.

The invention further provides a bioconjugate or a multimer thereof, comprising:
  a. a peptide or a polypeptide of anyone of Formulae I to IV,
  b. a half-life extending moiety;
  wherein said peptide or polypeptide and said half life are covalently linked or fused, optionally via a linker.
  "Optionally via a linker" means that the peptide of polypeptide according to Formulae I-IV is covalently linked or fused to the half-life extending moiety directly (i.e. with no linker) or is covalently linked or fused to the half-life extending moiety via a linker.

The half-life extending moiety of the invention can be covalently fused, attached, linked or conjugated to a peptide or polypeptide analog. A half-life extending moiety can be, for example, a polymer, such as polyethylene glycol (PEG), a cholesterol group, a carbohydrate or oligosaccharide; a fatty acid or any natural or synthetic protein, polypeptide or peptide that binds to a salvage receptor. Preferably, the half-life extending moiety is covalently linked, optionally via a linker, to plasma protein (albumin and immunoglobulin) with long serum half-lives. In other embodiment, the half-life extending moiety is an albumin binding residue. An "Albumin binding residue" as used herein means a residue which binds non-covalently to human serum albumin. In one embodiment the albumin binding residue is a lipophilic residue. In another embodiment, the albumin binding residue is negatively charged at physiological pH. An albumin binding residue typically comprises a carboxylic acid which can be negatively charged. Examples of albumin binding residue includes fatty acids. In other embodiment, the half-life extending moiety is an IgG constant domain or fragment thereof (e.g., the Fc region), Human Serum Albumin (HSA), or an albumin-binding polypeptides or residue such as for example a fatty acid. Preferably, the half-life extending moiety portion of the bioconjugate is a human serum albumin or an Fc region. Most preferably, the half-life extending moiety portion of the bioconjugate is an Fc region.

The half-life extending moiety is attached in such a way so as enhance, and/or not to interfere with, the biological function of the constituent portions of the bio-conjugates of the invention, e.g., the peptide or polypeptide of the invention (Formulae I-IV). In some embodiments, the polypeptide of the invention can be fused to a half-life extending moiety, optionally via a linker. The half-life extending moiety can be a protein such as an IgG constant domain or fragment thereof (e.g., the Fc region), Human Serum Albumin (HSA), or albumin-binding polypeptides or residue (e.g. a fatty acid). Such proteins disclosed herein can also form multimers.

In some embodiments, the half-life extending moiety (e.g., HSA, Fc, fatty acid etc.) is covalently linked or fused to the N-terminus of the peptide or polypeptide of any one of Formulae I-IV. In other embodiments, the half-life extending moiety (e.g., HSA, Fc, fatty acid etc.) is covalently linked or fused to C-terminus of the peptide or polypeptide of any one of Formulae I to IV of the invention.

The polypeptides of the invention, or bioconjugates thereof, via activation of the APJ receptor, have utility in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In a preferred embodiment the polypeptides of the invention, or bioconjugates thereof, are useful in the treatment of acute decompensated heart failure (ADHF).

In another embodiment, the invention pertains to a method for treating disorder or disease responsive to the activation of the APJ receptor, in a subject in need of such treatment, comprising: administering to the subject an effective amount of a polypeptide according to any one of Formulae I to IV, or an amide, an ester of a salt thereof, or a bioconjugate thereof, such that the disorder or disease responsive to the activation of the APJ receptor in the subject is treated.

In yet another embodiment, the invention pertains to pharmaceutical compositions, comprising a polypeptide according to any one of Formulae I to IV, or an amide, an ester or salt thereof, or a bioconjugate thereof, and one or more pharmaceutically acceptable carriers.

In still another embodiment, the invention pertains to combinations including, a polypeptide according to any one of Formulae I to IV, or an amide, an ester or a salt thereof, or a bioconjugate thereof, and pharmaceutical combinations of one or more therapeutically active agents.

In another embodiment, the invention pertains to a method for activation of the APJ receptor in a subject in need thereof, comprising: administering to the subject a therapeutically effective amount of a polypeptide according to any one of Formulae I to IV, or an amide, an ester or a salt thereof or a bioconjugate thereof.

DETAILED DESCRIPTION OF THE INVENTION

For purposes of interpreting this specification, the following definitions will apply unless specified otherwise and whenever appropriate, terms used in the singular will also include the plural and vice versa.

As used herein, "disorders or diseases responsive to the modulation of the APJ receptor," "disorders and conditions responsive to the modulation of the APJ," "disorders and conditions responsive to the modulation of APJ receptor activity," "disorders responsive to the activation (or agonism) of the APJ receptor activity," and like terms include acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

As used herein, "Activation of APJ receptor activity," or "Activation of the APJ receptor," refers to an increase in the APJ receptor activity. The activation of the APJ receptor activity is also referred to as "agonism" of the APJ receptor, e.g., by administration of the peptides and polypeptides of the invention.

As used herein, the terms "polypeptide" and "peptide" are used interchangeably to refer to two or more amino acids linked together. Except for the abbreviations for the uncommon or unnatural amino acids set forth in Table 1 below, the art-recognized three letter or one letter abbreviations are used to represent amino acid residues that constitute the peptides and polypeptides of the invention. Except when preceded with "D", the amino acid is an L-amino acid. When the one letter abbreviation is a capital letter, it refers to the L-amino acid. When the one letter abbreviation is a lower case letter, it refers to the D-amino acid. Groups or strings or amino acid abbreviations are used to represent peptides. Peptides are indicated with the N-terminus on the left and the sequence is written from the N-terminus to the C-terminus.

Peptides of the invention contain non-natural amino acids (i.e., compounds that do not occur in nature) and other amino acid analogs as are known in the art may alternatively be employed.

Certain non-natural amino acids can be introduced by the technology described in Deiters et al., J Am Chem Soc 125: 11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice. Particular non-natural amino acids that are beneficial for purpose of conjugating moieties to the polypeptides of the invention include those with acetylene and azido side chains.

One or more of the natural or un-natural amino acids in a peptide of the invention may be modified, for example, by the addition of a chemical entity such as a carbohydrate group, a phosphate group, a farnesyl group, an isofarnesyl group, a fatty acid group, a linker for conjugation, functionalization, or other modification, etc. Said modifications may be done in a site-specific or non-site-specific manner. In a preferred embodiment, the modifications of the peptide lead to a more stable peptide (e.g., one exhibiting greater half-life in vivo). These modifications may include the incorporation of additional D-amino acids, etc. None of the modifications should substantially interfere with the desired biological activity of the peptide, but such modifications may confer desirable properties, e.g., enhanced biological activity, on the peptide.

Said modifications enhance the biological properties of the proteins of the invention relative to the wild-type proteins, as well as, in some cases, serving as points of attachment for, e.g., labels and protein half-life extension agents, and for purposes of affixing said variants to the surface of a solid support.

In certain embodiments, such modifications, e.g., site-specific modifications, are used to attach conjugates, e.g., PEG groups to polypeptides, and/or peptides of the invention, for purposes of, e.g., extending half-life or otherwise improving the biological properties of said polypeptides, and/or peptides. Said techniques are described further herein.

In other embodiments, such modifications, e.g., site-specific modifications, are used to attach other polymers and small molecules and recombinant protein sequences that extend half-life of the polypeptide of the invention. One such embodiment includes the attachment of fatty acids or specific albumin binding compounds to polypeptides, and/or peptides. In other embodiments, the modifications are made at a particular amino acid type and may be attached at one or more sites on the polypeptides.

In other embodiments, such modifications, e.g., site-specific modifications, are used as means of attachment for the production of wild-type and/or variant multimers, e.g., dimers (homodimers or heterodimers) or trimers or tetramers. These multimeric protein molecules may additionally have groups such as PEG, sugars, and/or PEG-cholesterol conjugates attached or be fused either amino-terminally or carboxy-terminally to other proteins such as Fc, Human Serum Albumin (HSA), etc.

In other embodiments, such site-specific modifications are used to produce proteins, polypeptides and/or peptides wherein the position of the site-specifically incorporated pyrrolysine or pyrrolysine analogue or non-naturally occurring amino acids (para-acetyl-Phe, para-azido-Phe) allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates. In other embodiments, a site specific modification may include a branching point to allow more than one type of molecule to be attached at a single site of a protein, polypeptide or peptide.

In other embodiments, the modifications listed herein can be done in a non-site-specific manner and result in protein-protein conjugates, protein-polypeptide conjugates, protein-peptide conjugates, polypeptide-polypeptide conjugates, polypeptide-peptide conjugates or peptide-peptide conjugates of the invention.

In some embodiments, the present invention provides complexes which comprise at least one peptide or polypeptide of any one of Formulae I-IV bound to an antibody, such as an antibody which specifically binds a peptide or polypeptide as disclosed herein.

One of ordinary skill in the art will appreciate that various amino acid substitutions, e.g. conservative amino acid substitutions, may be made in the sequence of any of the polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non natural amino acids having a thiol-containing side chain, substituting a lysine for homolysine, diaminobutyric acid, diaminopropionic acid, ornithine or other non natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) apelin protein sequence or the sequences of the present invention. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) Apelin protein sequence or the sequences of the invention. The non-natural amino acid residue also can be incorporated such that a desired functionality is imparted to the apelin molecule, for example, the ability to link a functional moiety (e.g., PEG). When used in connection with amino acids, the symbol "U" shall mean "non-natural amino acid" and "unnatural amino acid," as used herein.

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3- diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthylalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

TABLE 1

Un-natural or non-natural amino acids as described in the invention:

| Symbol | Name | Structure |
|---|---|---|
| Nva or nva (D-Nva) | L-Norvaline or D-Norvaline | 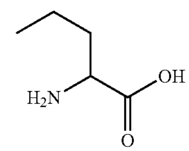 |
| 1-Nal | 1-Naphthylalanine | 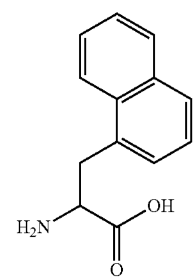 [SMILES: NC(Cc1cccc2ccccc12)C(=O)O] |
| 2-Nal | 2-Naphthylalanine | 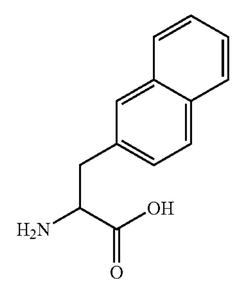 [SMILES: NC(Cc1ccc2ccccc2c1)C(=O)O] |
| Nle or nle (D-Nle) | L-Norleucine or D-Norleucine | 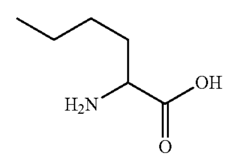 |
| pE | Pyroglutamic acid | 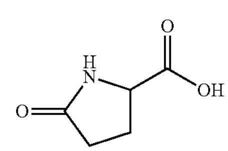 |
| Abu or abu (D-Abu) | 2-amino-butyric acid | 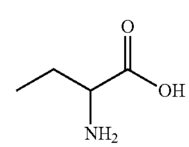 |

TABLE 1-continued

Un-natural or non-natural amino acids as described in the invention:

| Symbol | Name | Structure |
|---|---|---|
| O2Oc | 8-Amino-3,6-dioxaoctanoic acid | H₂N∼∼O∼∼O∼C(O)OH |

Nal refers to both 1-Naphthylalanine and 2-Naphthylalanine, preferably 2-naphthylalanine.

As used herein the term "amide" refers to an amide derivative of the carboxylic acid group at the C-terminus (e.g. —C(O)NH$_2$, —C(O)NH—C$_{1-6}$ alkyl, —C(O)NH—C$_{1-2}$alkylphenyl, —C(O)NH—NHBn, —C(O)-4 phenoxypiperidine or —C(O)N(C$_{1-6}$ alkyl)$_2$).

The term "amide" also refers to derivatives of the amino group at the N-terminus (e.g. —NHC(O)C$_{1-16}$alkyl, —NHC(O)(CH$_2$)$_n$Ph (n is an integer of 1 to 6), —NHC(O)(CH$_2$)$_2$CO$_2$H, 4-Cl-Ph-(CH$_2$)$_3$C(O)NH—, C$_{11}$H$_{23}$C(O)NH—(CH$_2$)$_2$—O—(CH$_2$)$_2$—O—CH$_2$—C(O)—NH—, C$_{13}$H$_{27}$C(O)NH—(CH$_2$)$_2$—O—(CH$_2$)$_2$—O—CH$_2$—C(O)—NH—; C$_{15}$H$_{27}$C(O)NH—(CH$_2$)$_2$—O—(CH$_2$)$_2$—O—CH$_2$—C(O)NH—, Ph-CH$_2$CH$_2$NHC(O)—NH— or CH$_3$(OCH$_2$CH$_2$)$_m$C(O)NH— (m is an integer of 1 to 12).

As used herein, the term "ester" refers to an ester derivative of the carboxylic acid group at the C-terminus (e.g —COOR) wherein R of the ester refers to C$_{1-6}$ alkyl groups such as methyl, ethyl, n-propyl, isopropyl, n-butyl, etc., C$_{3-8}$ cycloalkyl groups such as cyclopentyl, cyclohexyl, etc., C$_{6-10}$ aryl groups such as phenyl, α-naphthyl, etc., C$_{6-10}$ aryl-C$_{1-6}$ alkyl groups, for example phenyl-C$_{1-2}$ alkyl groups such as benzyl, phenethyl, benzhydryl, etc., and α-naphthyl-C$_{1-2}$ alkyl groups such as α-naphthylmethyl and the like. Mention may also be made of pivaloyloxymethyl ester and the like, which are commonly used as esters for oral administration. When the polypeptides of the invention possess additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

The term alkyl refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms.

The term aryl refers to monocyclic or bicyclic aromatic hydrocarbon groups having 6-10 carbon atoms in the ring portion. Representative examples of aryl are phenyl or naphthyl.

The term heteroaryl includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

The term cycloalkyl refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic.

The term heterocyclyl refers to a saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. In one embodiment, heterocyclyl moiety represents a saturated monocyclic ring containing from 5-7 ring atoms and optionally containing a further heteroatom, selected from O, S or N.

The term "APJ" (also referred to as "apelin receptor," "angiotension-like-1 receptor," "angiotension II-like-1 receptor," and the like) indicates a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136:355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

The term "apelin," indicates a 77 residue preprotein (NCBI Reference Sequence: NP_0059109.3, and encoded by NCBI Reference Sequence: NM_017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13mer of apelin (apelin-13), referred to as "Pyr-1-apelin-13 or Pyr'-apelin-13" Different apelin forms are described, for instance, in U.S. Pat. No. 6,492,324B1.

The term "conjugate" and "bioconjuagte" is used interchangeably and is intended to refer to the entity formed as a result of a covalent attachment between a polypeptide of anyone of Formulae I to IV, and a half-life extending moiety, optionally via linker. The term "Conjugate" or "bioconjugate" is also intended to include an entity formed as a result of a fusion between an APJ agonist polypeptide or a polypeptide of Formula I, II, III or IV, and a half life extending moiety.

The term half-life extending moiety can be covalently linked/attached or fused to a peptide or polypeptide analog. A half-life extending moiety can be, for example, a polymer, such as polyethylene glycol (PEG), fatty acid, a cholesterol group, a carbohydrate or olisaccharide; or any natural or synthetic protein, polypeptide or peptide that binds to a salvage receptor. In other embodiment, the half-life extending moiety is an albumin binding residue. An "Albumin binding residue" as used herein means a residue which binds non-covalently to human serum albumin. In one embodiment the albumin binding residue is a lipophilic residue. In another embodiment, the albumin binding residue is negatively charged at physiological pH. An albumin binding residue typically comprises a carboxylic acid which can be negatively charged. Examples of albumin binding residue includes fatty acids. In other embodiment, the half-life extending moiety is covalently linked, optionally via a linker, to plasma protein (albumin and immunoglobulin) with long serum half-lives. For example, the half-life extending moiety is an IgG constant domain or fragment thereof (e.g., the Fc region), Human Serum Albumin (HSA), or an albumin-binding polypeptides or residue (e.g a fatty acid). Most preferably, the half-life extending moiety portion of the bioconjugate is an Fc region.

The term "increased half-life" or "increase serum half-life" or "extending half-life" is meant the positive change in circulating half-life of a modified biologically active molecule (e.g. apelin 13) relative to its non-modified form (or naked form of the peptide). Serum half-life is measured by taking blood samples at various time points after administration of the biologically active molecule, and determining the concentration of that molecule in each sample. Measuring the change in serum concentration with time allows calculation of the serum half-life of a modified molecule (e.g. conjugated molecule). By comparing the serum half-life of a modified molecule (e.g. conjugated molecule), with an unmodified molecule (e.g. apelin 13), the relative increase in serum half-life or t½ may be determined. The increase is desirably at least about two-fold, but a smaller increase may be useful.

Polypeptides of the Invention:

Various embodiments of the invention are described herein. It will be recognized that features specified in each embodiment may be combined with other specified features to provide further embodiments.

In embodiment 1, the invention therefore provides a peptide or a polypeptide formula (I) (SEQ ID NO: 1):

$$X1\text{-}R\text{-}X3\text{-}X4\text{-}L\text{-}S\text{-}X7\text{-}X8\text{-}X9\text{-}X10\text{-}X11\text{-}X12\text{-}X13 \qquad I$$

wherein:
X1 is the N-terminus of the polypeptide and is either absent, Q, A or pE or X1 is selected from C, c, hC, D-hC; wherein the side chain of C, c, hC or D-hC form a disulfide bond with the side chain of X7;
X3 is P or X3 is selected from C, c, hC and D-hC; wherein the side chain of C, c, hC or D-hC forms a disulfide bond with the side chain of X7;
X4 is R or X4 is selected from C, c, hC and D-hC; wherein the side chain of C, c, hC or D-hC forms a disulfide bond with the side chain of X7;
wherein only one of X1, X3 and X4 is a sulfur contain aminoacid selected from C, c, hC and D-hC;
X7 is C, c, hC or D-hC; and the side chain of X7 forms a disulfide bond with the side chain of C, c, hC or D-hC of either X1, X3 or X4;
X8 is K or F;
X9 is G, A or a or absent;
X10 is P or absent;
X11 is D-Nle, Nle, M or f; and
X12 is absent or P, f, a, D-Nva or D-Abu;
X13 is the C-terminus and is absent or is selected from (N-Me)F, F, f, a, y and Nal; wherein:
Nle is L-norleucine;
D-Nle is D-norleucine;
D-hC is D-homocysteine
hC is L-homocysteine;
Nal is L-naphathaline;
D-Nva is D-norvaline;
D-Abu is D-2-aminobutyric acid;
pE is L-pyroglutamic acid;
or an amide, an ester or a salt of the polypeptide; or a polypeptide substantially equivalent thereto.

In embodiment 2, the invention therefore provides a peptide or a polypeptide of formula (II) (SEQ ID NO: 2):

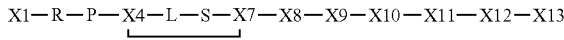

wherein:
X1 is the N-terminus of the polypeptide and is either absent, Q, A or pE;
X4 is C, c, hC or D-hC;
X7 is C, c, hC or D-hC; and the side chain of X7 forms a disulfide bond with the side chain of X4;
X8 is K or F;
X9 is G, A, a or absent;
X10 is P or absent;
X11 is D-Nle, M, Nle or f; and
X12 is absent or is selected from P, f, a, D-Nva and D-Abu;
X13 is the C-terminus and is absent or is selected from F, (N-Me)F, f, a, y and Nal; or an amide, an ester or a salt of the polypeptide, or a polypeptide substantially equivalent thereto.

In embodiment 2A, the invention therefore provides a peptide or a polypeptide of formula (II) (SEQ ID NO: 3):

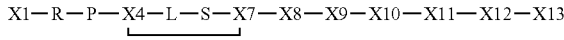

wherein:
X1 is the N-terminus of the polypeptide and is either absent or pE;
X4 is C, c, hC or D-hC;
X7 is C, c, hC or D-hC; and the side chain of X7 forms a disulfide bond with the side chain of X4;
X8 is K or F;
X9 is G, A, a or absent;
X10 is P or absent;
X11 is D-Nle Nle or f; and
X12 is absent or is selected from P, f, a, D-Nva and D-Abu;
X13 is the C-terminus and is absent or is selected from F, (N-Me)F, f, a, y and Nal; or an amide, an ester or a salt of the polypeptide, or a polypeptide substantially equivalent thereto.

In embodiment 3, the invention therefore provides a peptide or a polypeptide of formula III (SEQ ID NO: 4):

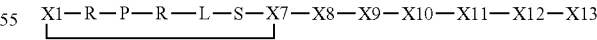

wherein
X1 is the N-terminus of the polypeptide and is selected from C, c, hC and D-hC;
X7 is C, c, hC or D-hC; wherein the side chain of X7 forms a disulfide bond with the side chain of X1;
X8 is K or F;
X9 is G, A, a or absent;
X10 is P or absent;
X11 is D-Nle, Nle, M or f; and
X12 is absent or is selected from P, f, a, D-Nva and D-Abu;

X13 is the C-terminus and is absent or is selected from (N-Me)F, F, f, a, y and Nal;
or an amide, an ester or a salt of the polypeptide.

In embodiment 3A, the invention pertains to polypeptides of Formula III wherein X11 is D-Nle, Nle or f, or an amide, an ester or a salt thereof.

In embodiment 4, the invention therefore provides a peptide or a polypeptide of Formula IV (SEQ ID NO: 5):

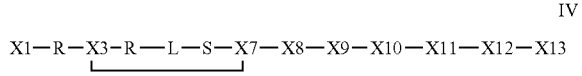

IV wherein:
X1 is the N-terminus of the polypeptide and is either absent, Q, A or pE;
X3 is C, c, hC or D-hC; wherein the side chain of C, c, hC or D-hC;
X7 is C, c, hC or D-hC; and the side chain of X7 form a disulfide bond with the side chain of C, c, hC or D-hC of X3;
X8 is K or F;
X9 is G, A, a or absent;
X10 is P or absent;
X11 is D-Nle, Nle, M or f; and
X12 is absent or is selected from P, f, a, D-Nva and D-Abu;
X13 is the C-terminus and is absent or is selected from (N-Me)F, F, f, a, y and Nal; or an amide, an ester or a salt of the polypeptide.

In embodiment 4A, the invention therefore provides a peptide or a polypeptide of Formula IV (SEQ ID NO: 6):

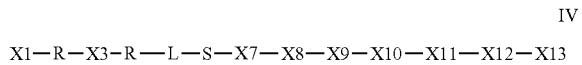

IV wherein:
X1 is the N-terminus of the polypeptide and is either absent or pE;
X3 is C, c, hC or D-hC; wherein the side chain of C, c, hC or D-hC;
X7 is C, c, hC or D-hC; and the side chain of X7 form a disulfide bond with the side chain of C, c, hC or D-hC of X3;
X8 is K or F;
X9 is G, A, a or absent;
X10 is P or absent;
X11 is D-Nle, Nle or f; and
X12 is absent or is selected from P, f, a, D-Nva and D-Abu;
X13 is the C-terminus and is absent or is selected from (N-Me)F, F, f, a, y and Nal; or an amide, an ester or a salt of the polypeptide.

In embodiment 5, the invention pertains to a polypeptide according to any one of embodiments 1, 2 and 4 wherein X1 is pE; or an amide, an ester or a salt of the polypeptide.

In embodiment 5A, the invention pertains to a polypeptide according to any one of embodiments 1, 2, and 4 wherein X1 is A or Q; or an amide, an ester or a salt of the polypeptide. In a particular aspect of this embodiment, the peptide is chemically linked or fused to a half-life extending moiety via it's A or Q N-terminus.

In embodiment 6, the invention pertains to a polypeptide according to any one of embodiments 1, 2, 4 and 4A wherein X1 is absent; or an amide, an ester or a salt of the polypeptide.

In embodiment 7, the invention pertains to a polypeptide according to any one embodiments 1 to 4 and 6 wherein the N-terminus is an amide; or a salt of the polypeptide.

In embodiment 8, the invention pertains to a polypeptide according to embodiment 7 wherein the N-terminus is an amide of Formula —NHR and R is Acetyl, benzoyl, phenacyl, succinyl, octanoyl, 4-phenylbutanoyl, 4-Cl-Ph-$(CH_2)_3$C(O)—, or Ph-$CH_2CH_2$NHC(O)—; or a salt of the polypeptide.

In embodiment 8A, the invention pertains to a polypeptide of any one of embodiments 1 to 4 and 7 wherein the N-terminus is an amide of Formula NHR1 wherein R1 is $CH_3$C(O)—, $CH_3$—(O—$CH_2CH_2$)$_m$—C(O)—, Palmitoyl(O2Oc)$_p$, Myristoyl(O2Oc)$_p$, Lauroyl(O2Oc)$_p$ or Ph-$CH_2CH_2$NHC(O)—; and wherein
p is an integer of 1 to 4;
m is an integer of 1 to 12;
Lauroyl(O2Oc) is $C_{11}H_{23}$C(O)NH—$(CH_2)_2$—O—$(CH_2)_2$—O—$CH_2$—C(O)—;
Myristoyl(O2Oc) is $C_{13}H_{27}$C(O)NH—$(CH_2)_2$—O—$(CH_2)_2$—O—$CH_2$—C(O)—;
Palmitoyl(O2Oc) is $C_{15}H_{31}$C(O)NH—$(CH_2)_2$—O—$(CH_2)_2$—O—$CH_2$—C(O)—; or a salt of the polypeptide.
Examples of N-terminus amides have been described in U.S. provisional application No. 61/591,557 filed on Jan. 27, 2012, which is hereby incorporated by reference.

In embodiment 9, the invention pertains to a polypeptide according to any one of embodiments 1 to 8A wherein X13 is F or f; or an amide, an ester or a salt of the polypeptide.

In embodiment 10, the invention pertains to a polypeptide according to any one of embodiments 1 to 8A wherein X13 is absent; or an amide, an ester or a salt of the polypeptide.

In embodiment 11, the invention pertains to a polypeptide according to any one of embodiments 1-10 wherein X12 is absent; or an amide, and ester or a salt of the polypeptide.

In embodiment 12, the invention pertains to a polypeptide according to any one of embodiments 1 to 11 wherein the C-terminus is an amide; or a salt of the polypeptide.

In embodiment 13, the invention pertains to a polypeptide according to embodiment 12 wherein the C-terminus is an amide of Formula —C(O)—R2 and R2 is —$NH_2$, —NH-Me, —NH—NHBn, —N($CH_3$)—$(CH_2)_2$-Ph or —NH—$(CH_2)_2$-Ph; or a salt of the polypeptide.

In embodiment 14, the invention pertains to a polypeptide according to any one of embodiments 1-13 wherein X8 is K; or an amide, an ester or a salt of the polypeptide.

In embodiment 15, the invention pertains to a polypeptide according to any one of embodiments 1 to 14 wherein X9 is G; or an amide, an ester or a salt of the polypeptide.

In embodiment 16, the invention pertains to a polypeptide according to any one of embodiments 1 to 15 wherein X10 is P; or an amide, an ester or a salt of the polypeptide. 19.

In embodiment 17, the invention pertains to a polypeptide according to any one of claims 1 to 16 wherein X11 is Nle or D-Nle; or an amide, an ester or a salt of the polypeptide.

In embodiment 17A, the invention pertains to a polypeptide according to anyone of embodiments 1 to 17, wherein the C-terminus consisting of the X11-X12-X13 moiety is selected from Nle-P-phenethylamine, Nle-P-(N-Me)F, Nle-P-NH2, Nle-Phenethylamine, (D-Nle)-phenethylamine, Nle-P-f, D-Nle-a-f, (D-Nle)-NH2, (D-Nle)-f, (D-Nle)-a-d, (D-Nle)-a-y, (D-Nle)-(D-Nva)-f, Nle-P-F, Nle-P-a, Nle-P-Nal and (D-Nle)-(D-Abu)-f, or a salt of the polypeptide. In one particular aspect of this embodiment, the invention relates to a polypeptide according to embodiment 17A wherein the C-terminus consisting of the X11-X12-X13 moiety is selected from (D-Nle)-phenethylamine, (D-Nle)-a-f and f-a-f, or a salt of the polypeptide.

In one embodiment 17B, the invention pertains to a peptide or polypeptide of anyone of embodiments 1 to 17, wherein at last two of the amino acids X1, X3, X4 and X7 to X13 are different from the corresponding amino acids present in Pyr-1-apelin-13. In another embodiment, the invention pertains to a peptide or polypeptide of anyone of embodiments 1 to 18 wherein at least three of the amino acids X1, X3, X4 and X7 to X13 are different from the corresponding amino acids present in Pyr-1-apelin-13. In yet another embodiment, the invention pertains to a peptide or polypeptide of anyone of embodiments 1 to 18 wherein at least four of the amino acids X1, X3, X4 and X7 to X13 are different from the corresponding amino acids present in Pyr-1-apelin-13.

In another embodiment, X1, X3, X4 and X7-X13 amino acids are those defined by X1, X3, X4, and X7-X13 amino acids in the Examples section below.

In another embodiment, individual polypeptides according to the invention are those listed in the Examples section below or a pharmaceutically acceptable salt thereof.

Unless specified otherwise, the term "polypeptide of the present invention" refers to a polypeptide of Formula (I) and subformulae thereof (Formulae II, III or IV); or an amide, an ester or a salt thereof.

Unless specified otherwise, the terms "polypeptides of the present invention," "peptides of the present invention," "apelin peptide agonists," and the like refer to peptides and polypeptides of Formula I and subformulae thereof (Formulae II, III or IV); or an amide, an ester or a salt thereof. The peptides and polypeptides of the invention demonstrate substantially equivalent or improved activity and/or plasma stability over known apelin peptides and polypeptides described herein, including but not limited to wild type apelin, apelin-13 and pyr-1-apelin-13.

The peptides and polypeptides of the invention also encompass peptides and polypeptides that are at least about 95% identical to the peptides and polypeptides according to any one of Formulae I, II, III or IV, or an amide, an ester or a salt thereof, as well as to any peptides or polypeptides specifically listed herein, including but not limited to the experimental examples.

As used herein, the phrase "homologous amino acid sequence," or variations thereof, refers to sequences characterized by a homology, at the amino acid level, of at least a specified percentage and is used interchangeably with "sequence identity." Homologous amino acid sequences include those amino acid sequences which contain conservative amino acid substitutions and which polypeptides have the same binding and/or activity. In some embodiments, an amino acid sequence is homologous if it has at least 60% or greater, up to 99%, identity with a comparator sequence. In some embodiments, an amino acid sequence is homologous if it shares one or more, up to 60, amino acid substitutions, additions, or deletions with a comparator sequence. In some embodiments, the homologous amino acid sequences have no more than 5 or no more than 3 conservative amino acid substitutions.

Homology may also be at the polypeptide level. The degree or percentage identity of peptides or polypeptides of the invention, or portions thereof, and different amino acid sequences is calculated as the number of exact matches in an alignment of the two sequences divided by the length of the "invention sequence" or the "foreign sequence", whichever is shortest. The result is expressed as percent identity.

A polypeptide comprising an amino acid sequence having a homology of about 80-99.9%, preferably 90-99.9% to the amino acid sequence described in the specific examples, and possessing a plasma stability superior to apelin-13 or pyr-1-apelin-13, fall under the category of the polypeptide of the invention. In one embodiment, the plasma stability improvement is at least 2 fold. In one embodiment, the polypeptide of the invention has a plasma stability of at least 30 minutes. In another embodiment, the polypeptide of the invention has a plasma stability of at least 60 minutes, or at least 80 minutes, preferably at least 100 min and more preferably at least 150 minutes.

The term "substantially equivalent" means the nature of the receptor-binding activity, signal transduction activity and the like is equivalent. Thus, it is allowable that even differences among grades such as the strength of receptor binding activity and the molecular weight of the polypeptide are present.

A polypeptide as described herein, or a substantial equivalent thereto, by substitution, deletion, addition or insertion of one or more of amino acids may be mentioned as polypeptides containing an amino acid sequence substantial equivalent(s) in the above sense. A polypeptide as described herein, or a substantial equivalent thereto, by substitution of 1 to 5, preferably 1 to 3 and more preferably 1 or 2 amino acids with natural or un-natural amino acids may be mentioned as polypeptides containing an amino acid sequence substantial equivalent(s) in the above sense. Further modifications and alterations may include the replacement of an L-amino-acid with a D-amino acid, or other variation including, but not limited to, phosphorylation, carboxylation, alkylation and the like as long as the apelin agonistic activity of the peptide or polypeptide of formulae I, II, III or IV is maintained and the plasma stability is improved over the pyroglutamated form of apelin-13.

In embodiment 19, the invention further pertains to a bioconjugate or a multimer thereof, comprising:
  a. a peptide or polypeptide of Formulae I, II, III or IV, an amide, salt or ester thereof, according to anyone of the preceding embodiments;
  b. a half-life extending moiety;
wherein said peptide or polypeptide and said half-life extending moiety are covalently linked or fused, optionally via a linker.

In embodiment 19A, the half-life extending moiety is attached to the N-terminus of the peptide of Formula I, II, III or IV, optionally via a linker moiety.

In embodiment 19B, the half-life extending moiety is covalently linked or fused to the C-terminus of the peptide of Formula I, II, III or IV, optionally via a linker moiety.

In embodiment 19C, the half-life extending moiety is covalently linked or fused to a side chain of the peptide of Formula I, II, III or IV, e.g. the half-life is covalently linked or fused to an amino group in the side chain of K, Orn, Dab, Dap, hK or 4-amino-Isn, optionally via a linker moiety. Preferably, the half-life extending moiety is attached to the N-terminus of the peptide of Formula I, II, III or IV, optionally via a linker moiety.

In embodiment 20, the invention pertains to the bioconjugate or a multimer thereof, according to embodiment 19, wherein the half-life extending moiety is an IgG constant domain or fragment thereof, a fatty acid or a human Serum Albumin.

In embodiment 21, the invention pertains to a bioconjugate according to embodiments 19 or 20 wherein the half-life extending moiety is a FcLALA modified Fc fragment with a LALA mutation (L234A, L235A).

In embodiment 22, the invention pertains to the bioconjugate according to embodiment 21 wherein the half-life extending moiety is a Fc domain which is fused or covalently linked to a polypeptide of Formula I, IL III or IV via a linker and wherein the linker has the following Formula: -[GGGGS]n-, n is 1, 2 or 3 (SEQ ID NO: 7) or the linker is GG or GS and the polypeptide of Formula I, II, III or IV contains naturally occurring amino acids.

In embodiment 23, the invention pertains to the bioconjugate according to embodiment 22 wherein the polypeptide is a polypeptide of Formula I is selected from QRPC*LSC*KGPMPF (SEQ ID NO: 8), C*RPRLSC*KGPMPF (SEQ ID NO: 9) and QRC*RLSC*KGPMPF (SEQ ID NO: 10), wherein the two amino acids labeled with "*" represent the amino acids forming a disulfide or amide bond via their side chain.

In embodiment 23A, the invention pertains to a bioconjugate according embodiment 22 or 23 wherein the half-life extending moiety is a modified Fc domain wherein the C-terminal Lysine has been deleted or replaced with Alanine. Such Fc-variants have been described in co-filed application (U.S. provisional application No. 62/015,848) and have generated more stable fusion proteins with Apelin peptide/polypeptides.

In embodiment 24, the invention pertains to the bioconjugate or multimer thereof according to embodiment 19 or 20 wherein the half-life extending moiety is Human Serum Albumin.

In embodiment 25, the invention pertains to the bioconjugate according to embodiment 24 wherein the Human Serum Albumin is chemically linked to the N-terminus of a polypeptide of any one of Formulae I to IV via a linker of the following Formulae:

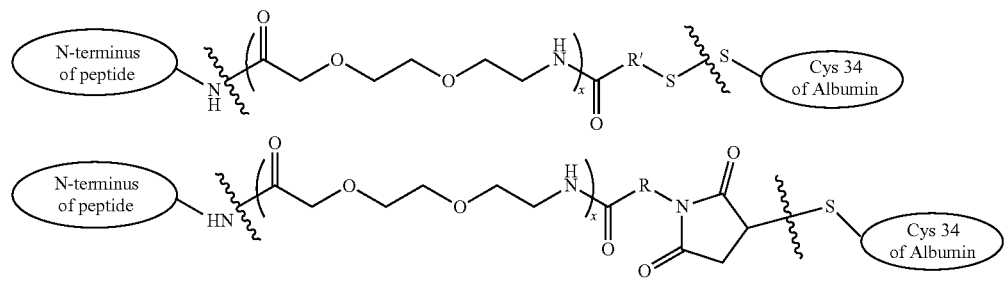

wherein x is 1-20, R is linear or branched alkylene, cycloalkyl, aryl of heteroaryl or combination thereof, R' is linear or branched alkylene, aryl or cycloalkyl or combination thereof.

In embodiment 26, the invention pertains to the bioconjugate according to embodiment 19 or 20 wherein the Human Serum Albumin is chemically linked to the C-terminus of a polypeptide of any one of Formulae I to IV via a linker of the following Formulae:

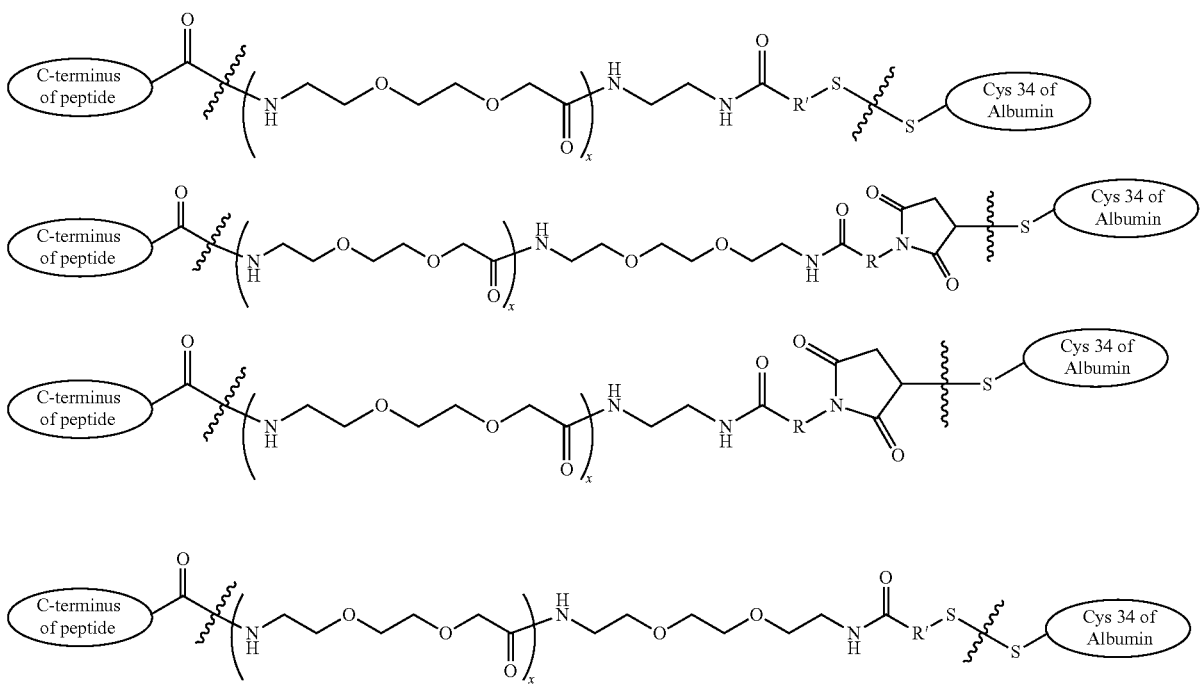

-continued

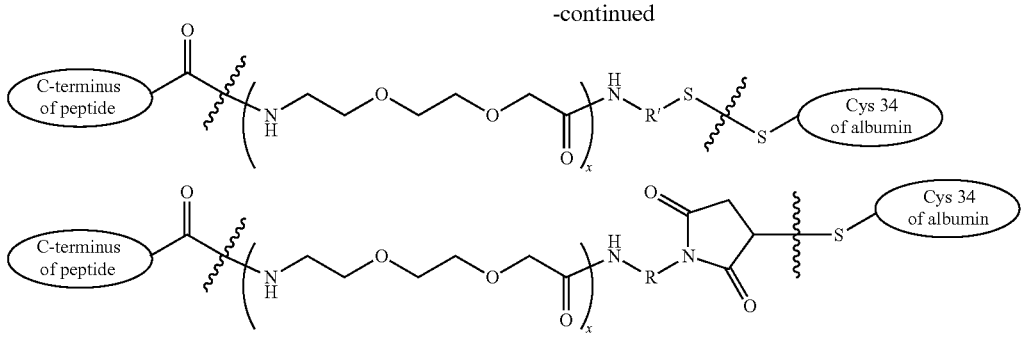

wherein x is 1-20, R is linear or branched alkylene, cycloalkyl, aryl of heteroaryl or combination thereof, R' is linear or branched alkylene, aryl or cycloalkyl or combination thereof.

In other embodiment, the bioconjugate of the invention has the following formulae:

(SEQ ID NO: 11)

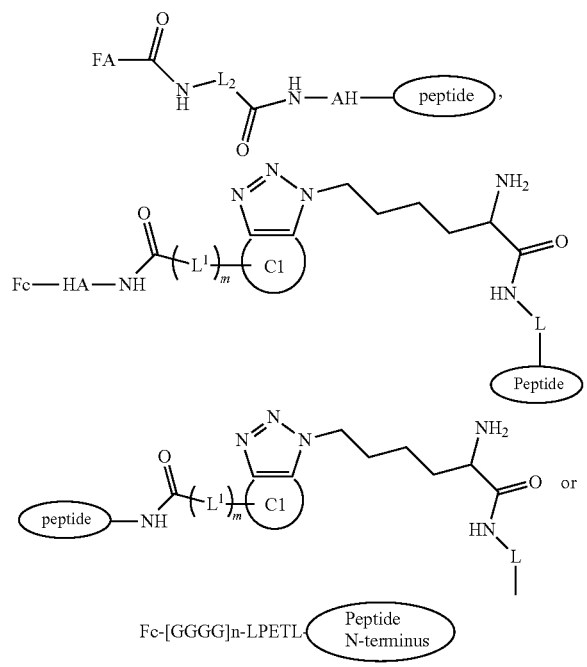

wherein peptide is the N-terminus of the peptide, A is alanine, H is histidine, n is 1, 2 or 3, m is 0 or 1, L and L2 are linkers, C1 is a mono, di or tricyclic carbocyclic or heterocyclic ring system optionally substituted with fluorine and $L^1$ is a C1-C20 alkylene linker wherein the alkylene chain is optionally substituted with oxo (=O), and wherein one or more carbon is replaced with O or NH. In a particular aspect of this embodiment, L and L2 are PEG linkers.

Half-Life Extending Moiety

The half-life extending moiety of the invention can be covalently attached, linked, conjugated or fused to a peptide or polypeptide analog. A half-life extending moiety can be, for example, a polymer, such as polyethylene glycol (PEG), a fatty acid, a cholesterol group, a carbohydrate or olisaccharide; or any natural or synthetic protein, polypeptide or peptide that binds to a salvage receptor. Preferably, the half-life extending moiety is covalently linked, optionally via a linker, to plasma protein (albumin and immunoglobulin) with long serum half-lives. For example, the half-life extending moiety is an IgG constant domain or fragment thereof (e.g., the Fc region), Human Serum Albumin (HSA), or albumin-binding polypeptides or residue (e.g a fatty acid). Preferably, the half-life extending moiety portion of the bioconjugate is human serum albumin, a fatty acid or an Fc region.

Half-life extending moieties include Albumin, which refers to the most abundant protein in the blood plasma having a molecular weight of approximately between 65 and 67 kilodaltons in its monomeric form, depending on species of origin. The term "albumin" is used interchangeably with "serum albumin" and is not meant to define the source of albumin which forms a conjugate with the modified peptides of the invention. Thus, the term "albumin" as used herein may refer either to albumin purified from a natural source such as blood or serous fluis, or it may refer to chemically synthesized or recombinantly produced albumin. Modified peptides or polypeptides of the invention are preferentially tethered to the free thiol group of the cysteine-34 on the surface of the albumin, optionally via a linker.

Half-life extending moieties include fatty acids, which can be defined as a C6-70alkyl, a C6-70alkenyl or a C6-70alkynyl chain, each of which is substituted with at least one carboxylic acid (for example 1, 2, 3 or 4 CO2H) and optionally further substituted with hydroxyl group. Examples of fatty acid are defined by Formulae A1, A2 and A3:

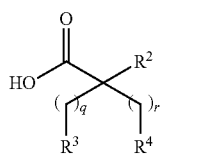

A1

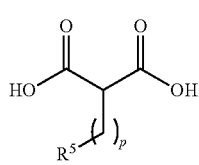

A2

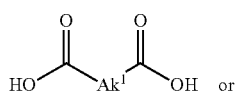

A3

$R^2$ is $CO_2H$, H;

$R^3$, $R^4$ and $R^5$ are independently of each other H, OH, $CO_2H$, —CH=$CH_2$ or —C≡CH;

$Ak^1$ is a branched $C_6$-$C_{30}$alkylene;

q, r and p are independently of each other an integer between 6 and 30; or an amide, an ester or a pharmaceutically acceptable salt thereof.

Examples of fatty acids are selected from:

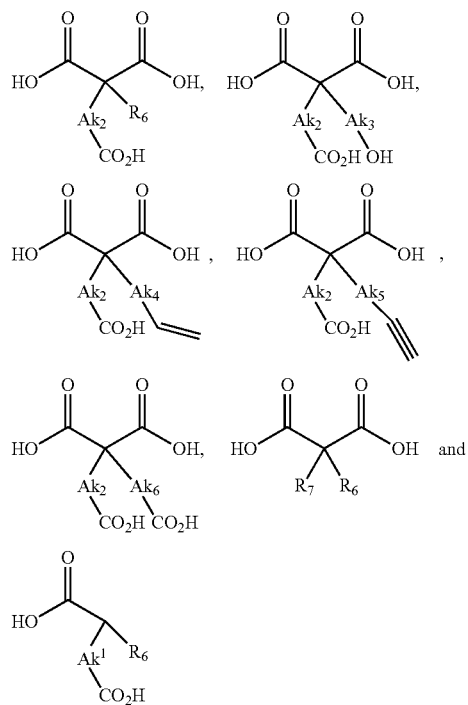

wherein $Ak^2$, $Ak^3$, $Ak^4$, $Ak^5$ and $Ak^6$ are independently a $(C_{8-20})$alkylene, $R^6$ and $R^7$ are independently $(C_{8-20})$alkyl.

More specifically, fatty acids are selected from:

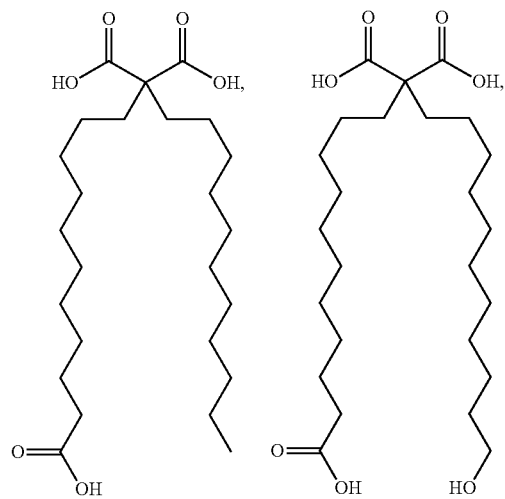

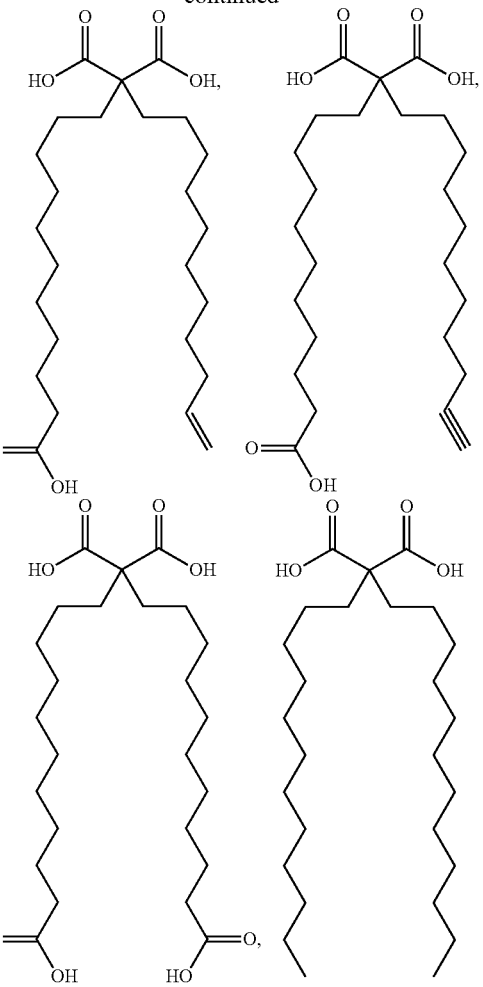

and

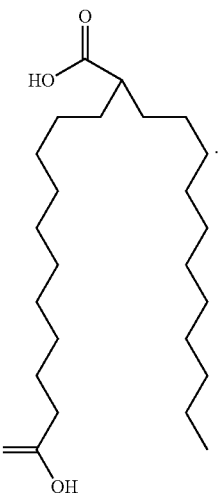

These fatty acid moieties have been described in co-filed application, U.S. provisional application No. 62/015,862.

Half-life extending moieties include "native Fc" which refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms.

Half-life extending moieties include "Fc variant" which refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the bioconjugate of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

Half-life extending moieties include Fc variant wherein the C-terminus lysine has been deleted or replaced with alanine.

Half-time extending moieties refer to "Fc domain" which encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be conjugated to a polypeptide of Formula I' or anyone of Formulae I-IV via, for example, a covalent bond between the Fc domain and the peptide sequence. Such Fc proteins can form multimers via the association of the Fc domains and both these Fc proteins and their multimers are an aspect of the present invention.

Half-life extending moieties include "modified Fc fragment", which shall mean an Fc fragment of an antibody comprising a modified sequence. The Fc fragment is a portion of an antibody comprising the CH2, CH3 and part of the hinge region. The modified Fc fragment can be derived from, for example, IgGI, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798.

The term "multimer" as applied to Fc domains or molecule comprising Fc domains refers to molecules having two or more polypeptide chains associated covalently. For example IgG molecules typically form dimers and therefore a bioconjugate comprising a dimeric IgG molecule would be fused to two polypeptide chains of Formula I, IA, II, III or IV.

Linker

Any linker group is optional. When present, its chemical structure is not critical, since it serves primarily as a spacer.

The linker is a chemical moiety that contains two reactive groups/functional groups, one of which can react with the polypeptide and the other with the half-life extending moiety. The two reactive groups of the linker are linked via a linking group, structure of which is not critical as long as it does not interfere with the coupling of the linker to the peptide and the half-extending moiety.

The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, cysteine and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). In some embodiments, a linker comprises a majority of amino acids selected from histidine, alanine, methionine, glutamine, asparagine and glycine. In some embodiments, linkers contain poly-histidine moiety. Examples of linkers are linkers which comprise the motif AH, MHA or AHA. Such motifs have been described in co-filed applications, U.S. provisional application No. 62/015,862 and U.S. provisional application No. 62/015,868, to be beneficial for selective conjugation at the N-terminus of a peptide or polypeptide.

Other examples of linkers comprises the motif GGGGSGGGGSGGGGS (SEQ ID NO: 12), GGGGSGGGGS (SEQ ID NO: 13), GGGGS (SEQ ID NO: 14), GS or GG.

In some other embodiment, the linker comprises recognition motifs for enzyme. An example is the LPXTG/A motif which can be included at the C-terminus wherein X is any amino acid, most commonly an E: Glutamic acid. (L: leucine, P: proline, T: threonine, G: Glycine, A; Alanine). (Carla P. Guimaraes et al.: "Site specific C-terminal and internal loop labeling of proteins using sortase-mediated reactions", Nature protocols, vol 8, No 9, 2013, 1787-1799)

In other embodiments, the linker comprises 1 to 20 amino acids which are selected from unnatural amino acids. While a linker of 3-15 amino acid residues is preferred for conjugation with the half-life extending moiety, the present invention contemplates linkers of any length or composition. A preferred amino acid linker is O2Oc of the following formula:

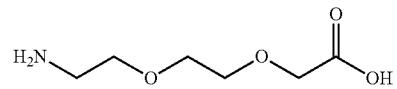 [SMILES: NCCOCCOCC(=O)O]

or its repeating units.

The linkers described herein are exemplary, and linkers that are much longer and which include other residues are contemplated by the present invention. Non-peptide linkers are also contemplated by the present invention.

The linking portion of the linker may comprise one or more alkyl groups, alkoxy groups, alkenyl groups, cycloalkyl groups, aryl groups, heteroaryl groups and heterocyclic groups or combination thereof. For example, alkyl linkers such as such as —NH—$(CH_2)_z$-C(O)— or —S—$(CH_2)_z$-C (O)— or —O—(CH$_2$)z-C(O)— wherein z is 2-20 can be used. These alkyl linkers can further be substituted by any non-sterically hindering group, including, but not limited to, a lower alkyl (e.g., C1-C6), lower acyl, halogen (e.g., Cl, Br), CN, NH2, or phenyl.

The linker can also be of polymeric nature. The linker may include polymer chains or units that are biostable or biodegradable. Polymers with repeat linkage may have varying degrees of stability under physiological conditions depending on bond lability. Polymers may contain bonds such as polycarbonates (—O—C(O)—O—), polyesters (—C(O)—O—), polyurethanes (—NH—C(O)—O—), polyamide (—C(O)—NH—). These bonds are provided by way of examples, and are not intended to limit the type of bonds employeable in the polymer chains or linkers of the invention. Suitable polymers include, for example, polyethylene glycol (PEG), polyvinyl pyrrolidone, polyvinyl alcohol, polyamino acids, divinylether maleic anhydride, N-(2-hydroxypropyl)-methacrylicamide, dextran, dextran derivatives, polypropylene glycol, polyoxyethylated polyol, heparin, heparin fragments, polysaccharides, cellulose and cellulose derivatives, starch and starch derivatives, polyalkylene glycol and derivatives thereof, copolymers of polyalkylene glycols and derivatives thereof, polyvinyl ethyl ether, and the like and mixtures thereof. A polymer linker is for example PEG. An exemplary non-peptide linker is a polyethylene glycol linker:

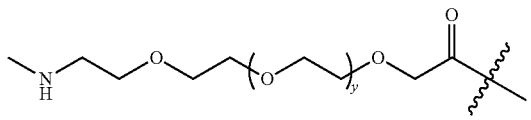

wherein y is so that the linker has a molecular weight of 100 to 5000 kD, for example, 100 to 500 kD.

Preferably, the linking moiety contains one or more amino acid moieties such as for example (O2Oc) unit or Glycine or serine, C$_{1-4}$alkylene-C(O)—, C$_{1-4}$alkylene, —NH—C$_{2-6}$alkylene-NH— or —NH—CH$_2$CH$_2$—O—CH$_2$CH$_2$—NH— diamino units or combination thereof and the linking moiety linked 2 reactive groups or functional groups.

Preferably, the reactive groups or functional groups are maleimide, thiol or pyridine-2-yldisulfanyl.

Preparation of Peptide or Polypeptide and Peptide-Linker Construct for Attachment to a Half-Life Extending Moiety:

The apelin peptides and polypeptides and/or peptide-linker construct of the invention may be produced by either synthetic chemical processes or by recombinant methods or combination of both methods. The Apelin peptides and/or peptide-linker constructs may be prepared as full-length or may be synthesized as non-full length fragments and joined. The peptides and polypeptides of the present invention can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5).

(1) M. Bodanszky and M. A. Ondetti, Peptide Synthesis, Interscience Publishers, New York, 1966,
(2) Schroeder and Luebke, The Peptide, Academic Press, New York, 1965,
(3) Nobuo Izumiya et al. Fundamentals and Experiments in Peptide Synthesis, Maruzen, 1975,
(4) Haruaki Yajima and Shumpei Sakakibara, Biochemical Experiment Series 1, Protein Chemistry IV, 205, 1977, and
(5) Haruaki Yajima (ed.), Development of Drugs-Continued, 14, Peptide Synthesis, Hirokawa Shoten.

After the reaction, the peptide can be purified and isolated by a combination of conventional purification techniques such as solvent extraction, column chromatography, liquid chromatography, and recrystallization. Where the peptide isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl) phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g. a carbodiimide. The carbodiimide includes DCC, N,N'-diisopropylcarbodiimide, and N-ethyl-N'-(3-dimethylaminopropyl) carbodiimide. For activation with such a reagent, a racemization inhibitor additive, e.g. HOBt or Oxyma Pure can be used. The protected amino acid can be directly added to the resin along with the activation reagents and racemization inhibitor or be pre-activated as symmetric acid anhydride, HOBt ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned.

The reaction temperature can be selected from the range hitherto-known to be useful for peptide bond formation and is usually selected from the range of about −20° C.-50° C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{6-10}$aryl-$C_{1-2}$alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl, $Cl_2$-Bzl, 2-nitrobenzyl, Br—Z, and tertiary-butyl.

The protecting group of imidazole for histidine includes Tos, 4-methoxy-2,3,6-tri ethylbenzenesulfonyl, DNP, benzyloxymethyl, Bum, Boc, Trt, and Fmoc.

The activated carboxyl group of the starting amino acid includes the corresponding acid anhydride, azide and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the α-carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide. To obtain an ester of the polypeptide, the α-carboxyl group of the C-terminal amino acid is condensed with a desired alcohol to give an amino acid ester and then, the procedure described above for production of the amide is followed.

Alternatively, recombinant expression methods are particularly useful. Recombinant protein expression using a host cell (a cell artificially engineered to comprise nucleic acids encoding the sequence of the peptide and which will transcribe and translate, and optionally, secrete the peptide into the cell growth medium) is used routinely in the art. For recombinant production process, a nucleic acid coding for amino acid sequence of the peptide would typically be synthesized by conventionaly methods and integrated into an expression vector. Such methods is particularly preferred for manufacture of the polypeptide compositions comprising the peptides fused to additional peptide sequences or other proteins or protein fragments or domains. The host cell can optionally be at least one selected from *E. Coli*, COS-1, COS-7, HEK293, BHT21, CHO, BSC-1, Hep G2, 653, SP2/0, 293, heLa, myeloma, lymphoma, yeast, insect or plant cells, or any derivative, immortalized or transformed cell thereof.

The modified therapeutic peptides or polypeptides and/or peptide-linker construct include reactive groups which can react with available reactive functionalities on the half-life extending moiety to form a covalent bond. Reactive groups are chemical groups capable of forming a covalent bond. Reactive groups can generally be carboxy, phosphoryl, acyl group, ester or mixed anhydride, maleimide, imidate, pyridine-2-yl-disulfanyl, thereby capable of forming a covalent bond with functionalities like amino group, hydroxyl group, carboxy group or a thiol group at the target site of the Albumin or Fc domain. Reactive groups of particular interest for linking to an Albumin include maleimido-containing groups and pyridine-2-yl-disulfanyl containing group.

Functionalities are groups on Albumin or Fc domain to which reactive groups on modified peptides or polypeptides are capable of reacting with to form covalent bonds. Functionalities include hydroxyl groups for bonding with ester reative entities, thiol groups for reacting with maleimides, maleimido-containing groups or pyridine-2-yldisulfanyl, imidates and thioester groups; amino groups for bonding to carboxylic acid, phosphoryl groups, acyl groups; and carboxy groups for reacting with hydrazine, hydrazide or hydroxylamine.

Schemes 1 to 3 describe the synthesis of peptide-Linker construct wherein the peptide is a peptide according to anyone of Formulae I to IV.

Scheme 1 describes the synthesis of a maleimide containing linker attached to the N-terminus of a polypeptide of Formula I to IV.

Scheme 1

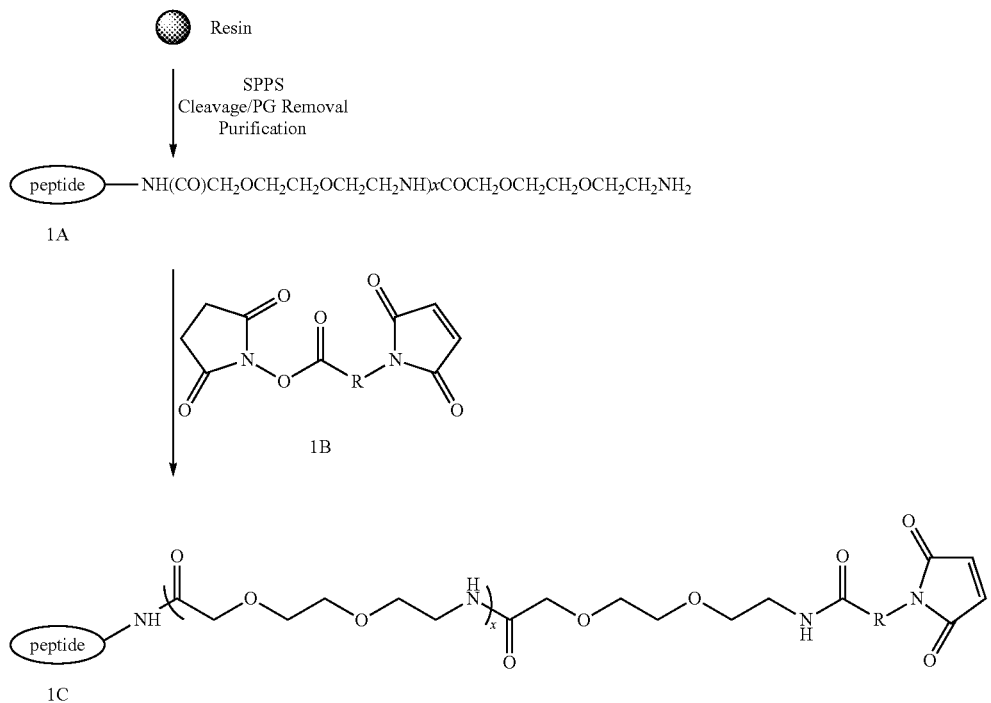

The N-terminus of the peptide is coupled with one or more O2Oc amino acid units (x is 1 to 20, preferably 1 to 10 and more preferably 3 to 6) according to well established amide coupling chemistry to generate (1A). The terminal amino functionality of (1A) is reacted with an activated acid (1B) wherein R is linear or branched alkylene, aryl, heteroaryl, cycloalkyl or combination thereof, in order to generate the peptide-maleimide containing linker construct (1C). The activated acid (1B) is commercially available or readily available from its corresponding carboxylic acid according to technique known to someone of ordinary skill in the art. Preferably, R is a linear alkylene, and more preferably R is —CH$_2$—CH$_2$—. Alternatively, for peptides containing an amino functionality in the side chain (for example peptide containing a lysine), orthogonal protecting group such as Alloc is required prior to the coupling reaction, followed by additional deprotection step in order to obtain (1C).

Scheme 2A and 2B describe the synthesis of pyridine-2-yl-disulfanyl containing linker attached to the N-terminus of a polypeptide according to any one of Formula I to IV.

Scheme 2A

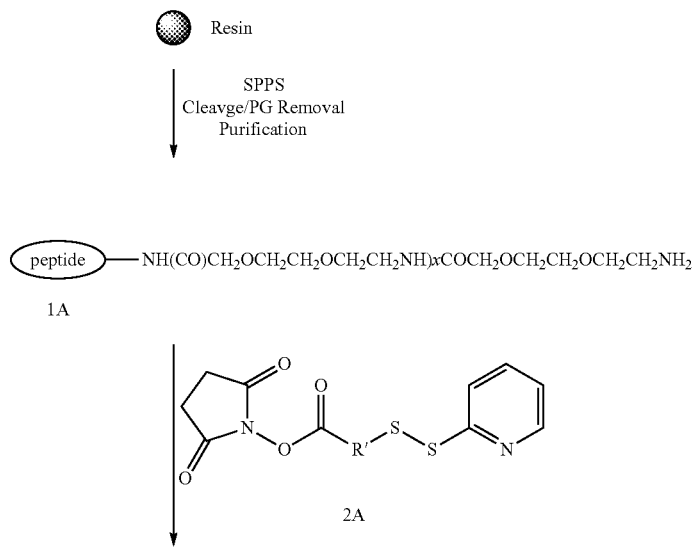

-continued

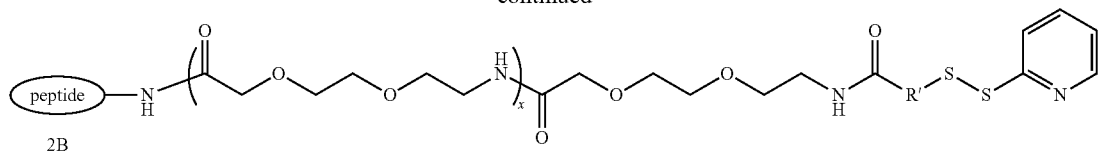

2B

Scheme 2B

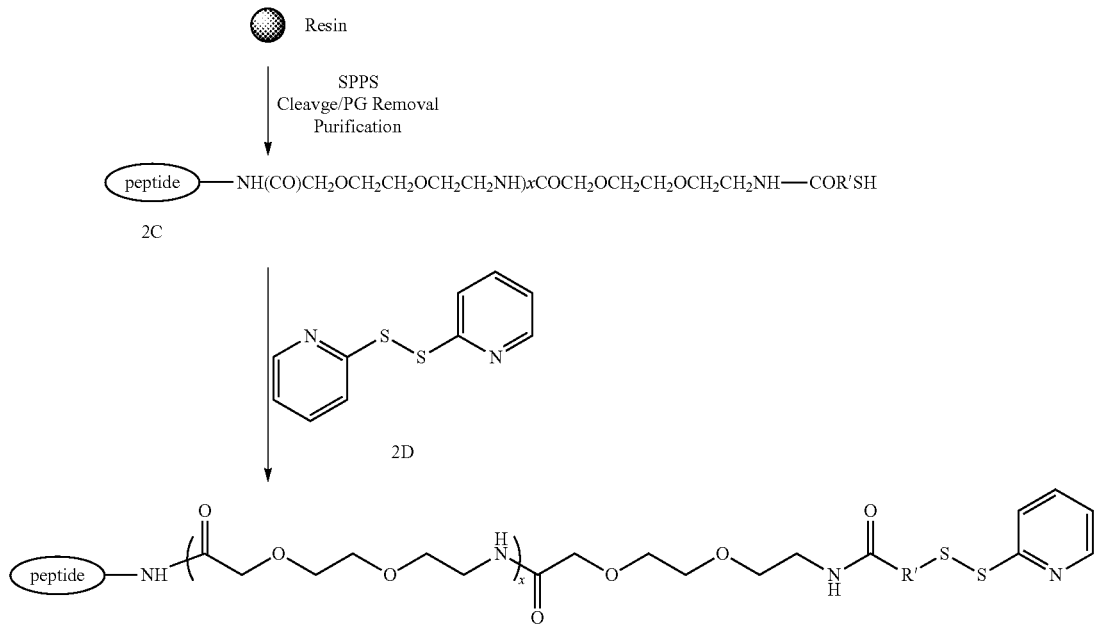

Peptide-Linker construct (1A) is prepared as described in Scheme 1 and is further reacted with an activated acid of Formula (2A) wherein R' is a linear or branched alkylene, to generate a peptide-pyridine-2-yl-disulfanyl containing linker construct (2B). Activated acid (2A) is commercially available or is readily available from its corresponding carboxylic acid according to techniques known to someone of ordinary skill in the art. Preferably R' is —CH$_2$—CH$_2$—. Alternatively, Peptide-linker construct (2C) can be prepared using HO$_2$C—R'—SH, or a protected form thereof (e.g. trityl or Acm groups, requiring additional deprotection steps), and further reacted with (2D) to generate peptide-pyridine-2-yl-disulfanyl containing linker construct (2B).

Similar reactive groups are attached to the C-terminus of the peptide in a similar way as described in Schemes 1, 2A and 2B using a diamino unit such as for example —NH—CH$_2$CH$_2$—NH— or —NH—CH$_2$CH$_2$—O—CH$_2$CH$_2$—NH—. Non limiting examples of such peptide-linker conducts are:

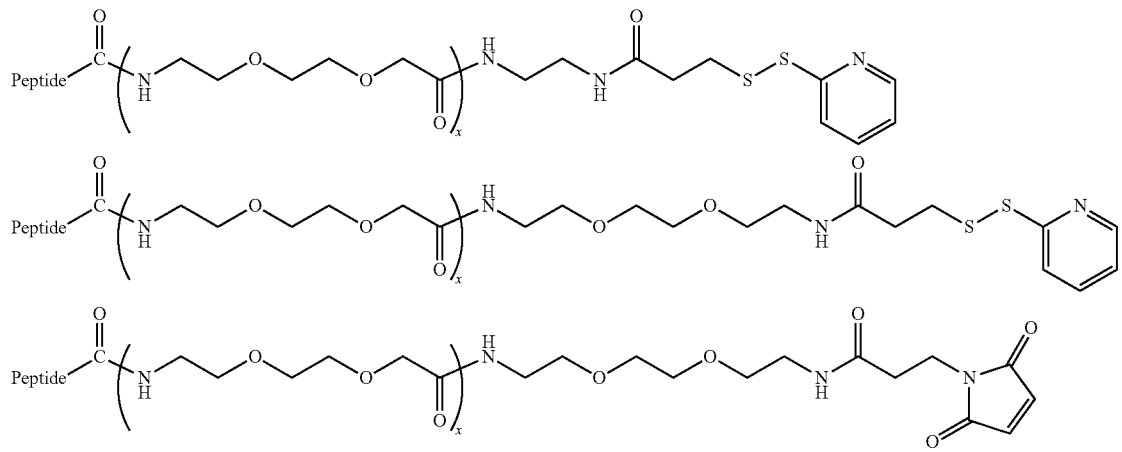

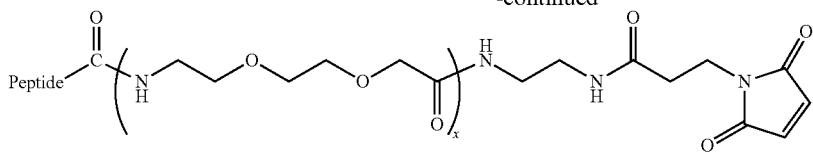

Alternatively maleimide or pyridine-2-yl-disulfanyl reactive group can be attached to a polypeptide according to any one of Formula I to IV according to scheme 3A, 3B and 3C:

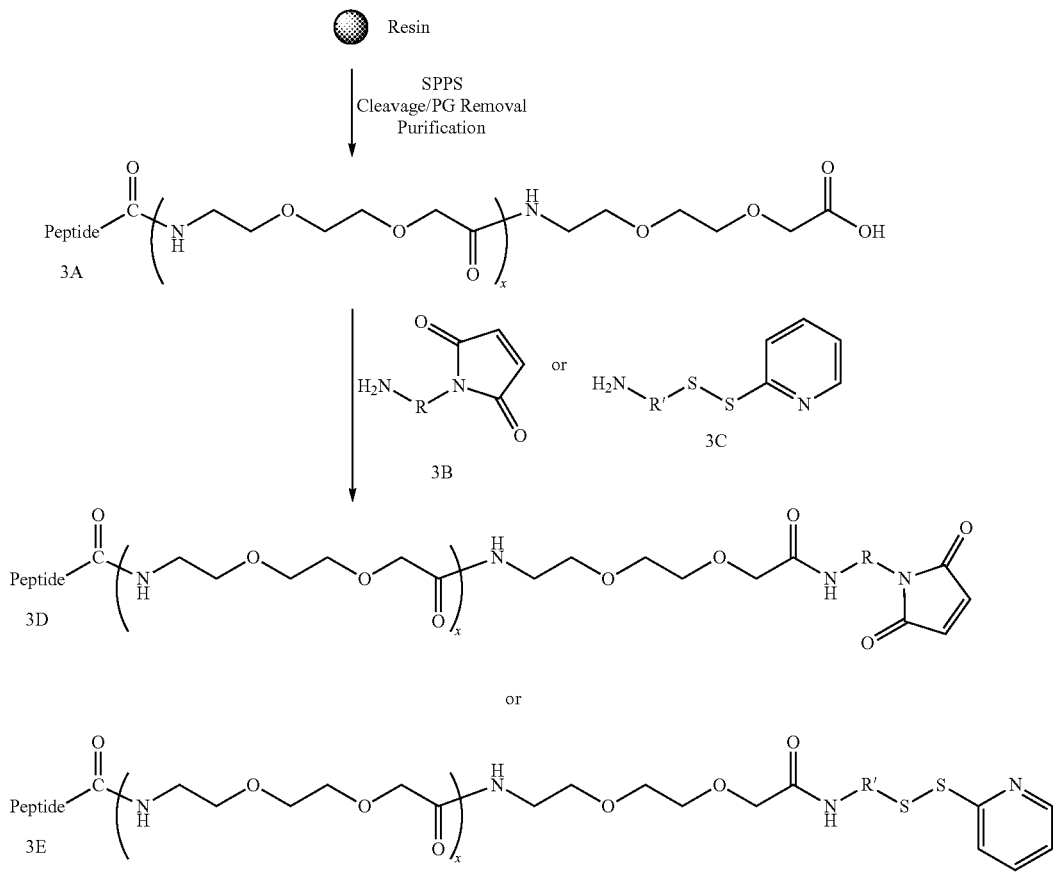

The carboxylic acid group at the C-terminus of the peptide is coupled with one or more O2Oc amino acid units using standard amide coupling conditions to generate (3A). The terminal carboxylic acid functionality reacts with the amino group of (3B) or (3C) wherein R and R' are as defined above, in order to generate the activated Peptide-Linker Constructs (3D) or (3E). Additionally, when a peptide contains a carboxy functionality side chain (e.g. Glu or Asp), orthogonal protecting group (e.g. O-Allyl) and additional deprotection steps are required.

Scheme 3B

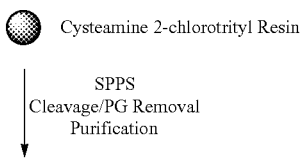

-continued
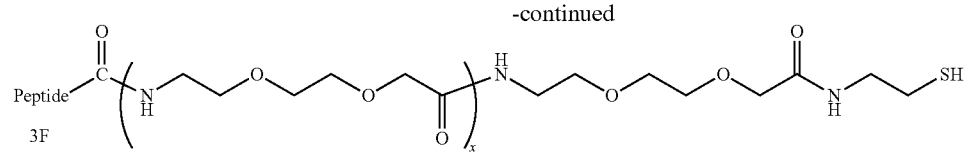
3F
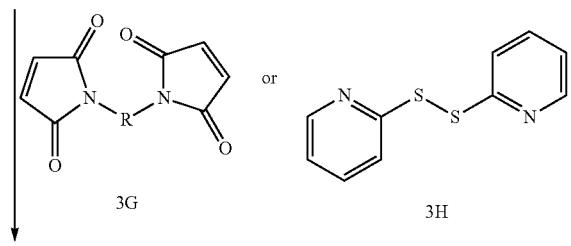
3G   3H
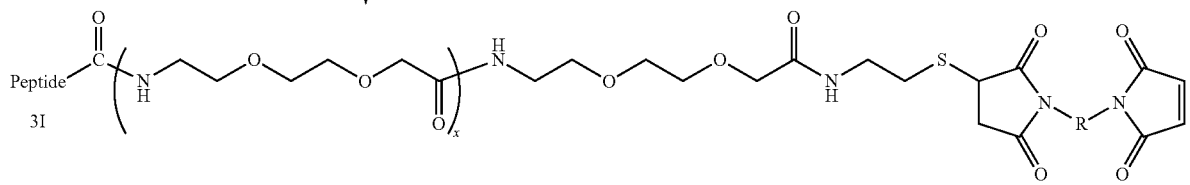
3I
or
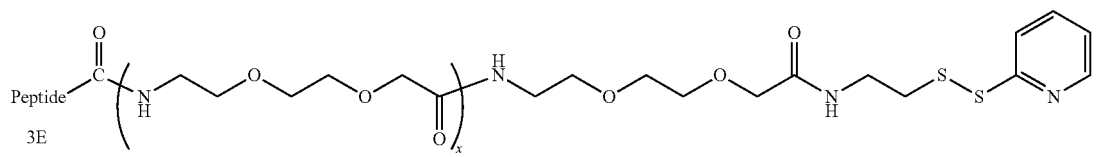
3E
Peptide-Linker Construct 3F can be obtained using a cysteamine 2-chlorotrityl Resin and then reacted with 3G or 3H to generate peptide-linker construct 3I or 3E respectively.
Scheme 3C
● diamine Resin
| SPPS
| Cleavage/PG Removal
| Purification
↓
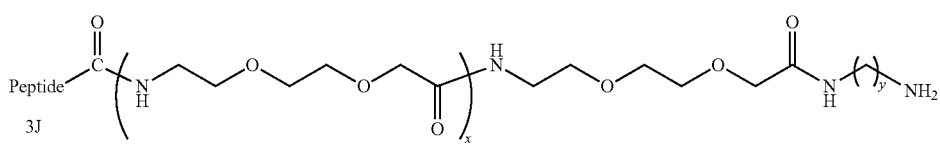
3J
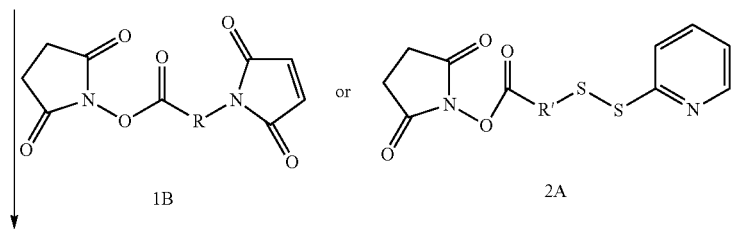
1B    2A

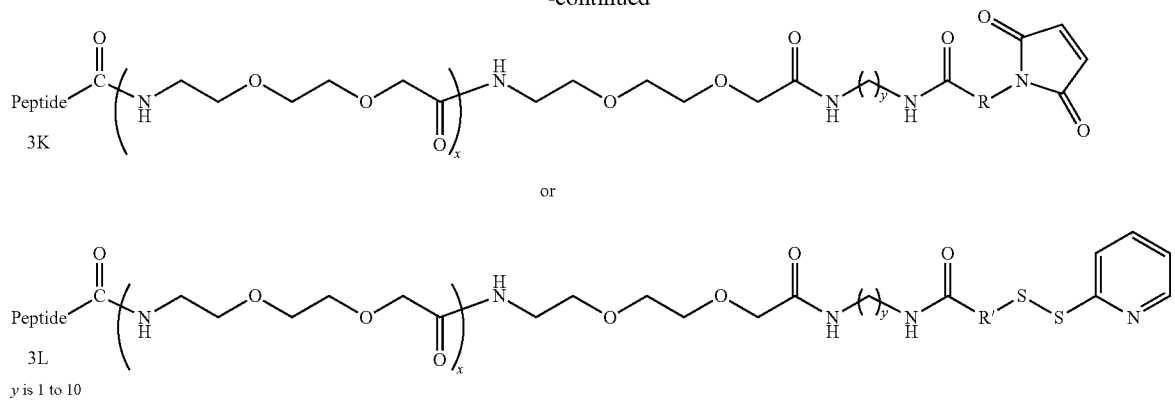

3K or

3L y is 1 to 10

Peptide-Linker Construct (3J) can be obtained from a diamine resin and be further reacted with (1B) or (2A) to generate a Peptide-Linker Construct of Formula (3K) or (3L) respectively.

Schemes 1 to 3C describe Peptide-Linker Constructs, more particularly for use in the preparation of a bioconjugate with Albumin. The maleimide reactive group and the pyridine-2-yl-disulfanyl reactive group reacts with the —SH functionality of Cysteine 34 of the albumin.

Schemes 3D and 3E describes preparation of peptide-linker constructs for use in an azide-alkyne Huisgen cycloaddition, more commonly known as click chemistry.

Scheme 3D

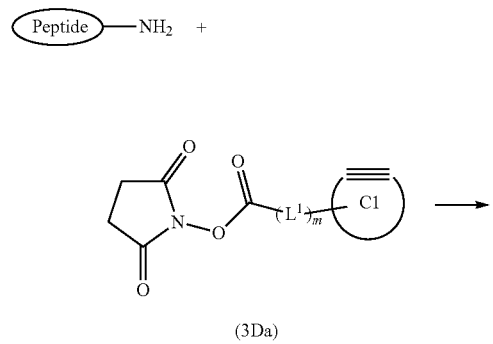

(3Da)

wherein m is 0 or 1, C1 is a mono, di or tricyclic carbocyclic or heterocyclic ring system optionally substituted with fluorine, $L^1$ is a C1-C20 alkylene linker wherein the alkylene chain is optionally substituted with oxo (=O), and wherein one or more carbon is replaced with O or NH. Cycloalkyne moieties (3 Da) are readily available from commercial sources. Additionally, cyclic alkyne in click chemistry for protein labeling has been described in US 2009/0068738 which is herein incorporated by reference. Specific examples have been described below (example 20). The click handle can be introduced at the N-terminus of the peptide or on a lysine residue side chain.

Scheme 3E

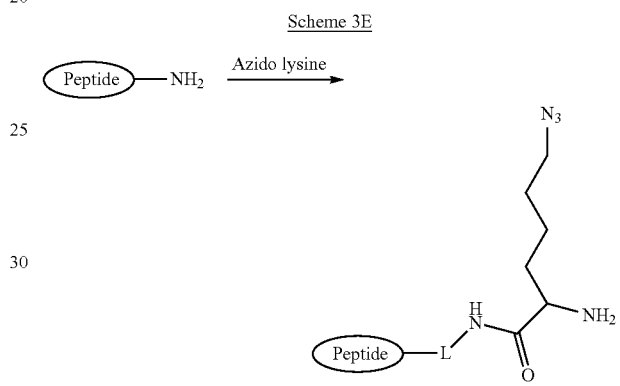

Scheme 3E describes the introduction of an Azido lysine residue at the N-terminus of an apelin peptide optionally via a linker L (such as for example one or more amino acids selected from Glycine and serine). The azide functionality acts as a handle for click chemistry.

Preparation of Half-Life Extending Moiety-Linker Construct:

Scheme 3F and 3G describes the preparation of a fatty acid-linker construct.

Scheme 3F

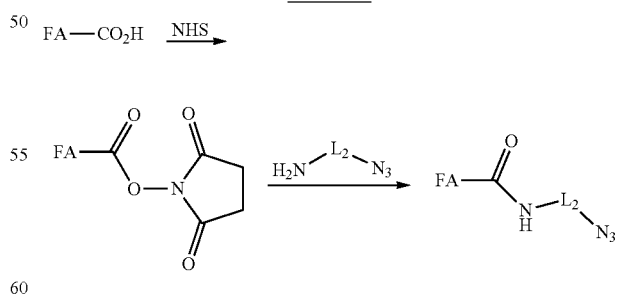

wherein FA is fatty acid, L2 is a linking moiety (for example PEG), NHS is N-hydroxysuccinimide. Such fatty acid-linker constructs are used for conjugation using click chemistry. In instances wherein the fatty acid contains functionalities such as hydroxyl or additional carboxylic acid, protection of such functionalities may be required.

Scheme 3G

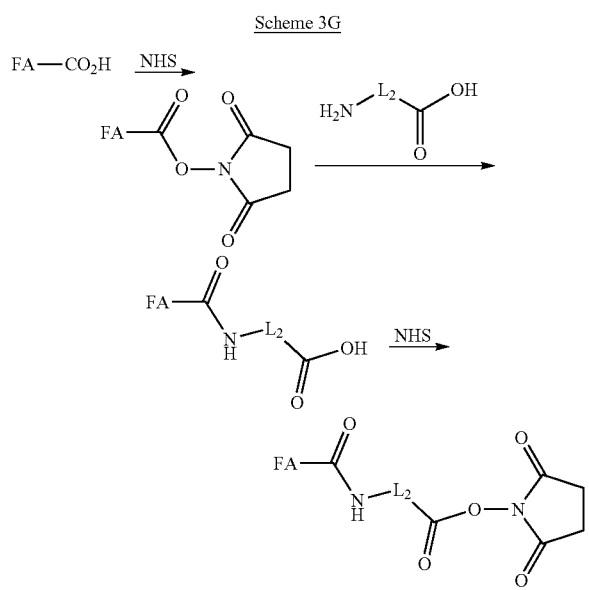

Wherein FA, NHS and L2 are defined above in Scheme 3F. Such fatty acid constructs are used for conjugation with an amino functionality on the peptide, preferably the N-terminus.

Scheme 3H describes the preparation of a Fc-linker construct

Scheme 3H

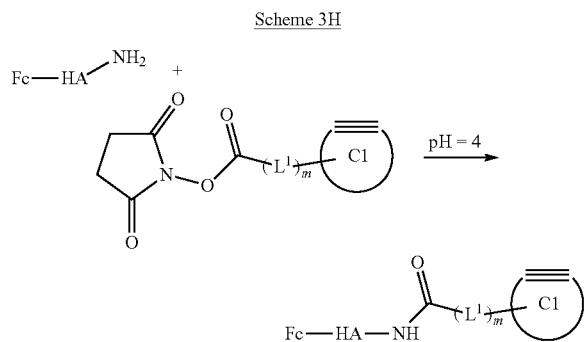

AH-Fc is a construct containing the sequence AH- at the N-terminus of the Fc. The construct is prepared using recombinant methods. The AH-sequence allows for selective modification of the N-terminus at a low pH. Such selective modification has been disclosed in cofiled applications (U.S. provisional application No. 62/015,868 and U.S. provisional application No. 62/015,862). Click handle is therefore introduced at the N-terminus of the Fc construct.

In yet another embodiment, the Fc construct is modified at the C-terminus to introduce a small Sortase recognition motif (LPXTG/A).

Such Fc-recognition motif is prepared using recombinant methods. Example of such construct is: Fc-[GGGG]n-LPETGGLEVLFQGP (SEQ ID NO: 15) wherein the GGLEVLFQGP (SEQ ID NO: 16) is clipped during sortase treatment.

Preparation of the Fc APJ Peptide Fusion Protein

The biologically generated multimerized molecule, such as an antibody Fc comprising at least a part of cysteine containing region known as the hinge can be prepared from recombinant expressed protein product which has been secreted in multimerized (e.g. dimeric) form. The present invention also include modified Fc fusion proteins wherein the amino acid sequence of the Fc region has been altered relative to the amino acid sequence of the Fc- or constant region found in a naturally occurring antibody. For example, Fc-fusion protein may be engineered (i.e. modified) with mutations in order to obtain desired characteristics of FcRn binding affinity/or serum half-life. Example of modified Fc-fusion proteins have been disclosed in U.S. Pat. No. 7,217,798, which is incorporated by reference.

Fc-fusion proteins of this invention may also be altered synthetically, e.g. by attachment of the linker moiety and the peptide or polypeptide moiety. In addition, "modified" Fc-fusion proteins with Fc domain derived from recombinant antibodies can be made in any expression systems including both prokaryotic and eukaryotic expression system or using phage display methods.

Fc-Linker Constructs such as Fc-[GGGGS] (SEQ ID NO: 14), Fc-[GGGGS]2 (SEQ ID NO: 13), Fc-[GGGGS]3 (SEQ ID NO: 12), Fc-GG and Fc-GS, are described below in the experimental part. The [GGGGS] (SEQ ID NO: 14), [GGGGS]2 (SEQ ID NO: 13), [GGGGS]3. (SEQ ID NO: 12), GS and GG linker are attached either to the C-terminus of the Fc domain or to the N-terminus of the Fc domain, wherein Fc is a native Fc or a variant thereof. Example of Fc variant includes a Fc wherein the C-terminal Lysine has been deleted or replaced with Alanine. Such Fc variant has been described in co-filed application (US provisional applications No. 62/015848)

Bioconjugates

In one embodiment of the present invention, a peptide or polypeptide according to anyone of Formula I to IV is conjugated (chemically/covalently attached) to the thiol functionality of cysteine 34 of the albumin. In one aspect of this embodiment, the Albumin-Peptide refers to a bioconjugate in which the Albumin is conjugated (chemically linked) to the N-terminus of the peptide. In yet another embodiment, the Albumin-Peptide refers to a bioconjugate in which the Albumin is conjugated (chemically linked) to the C-terminus of the peptide.

In another embodiment of the present invention, a peptide or polypeptide according to anyone of Formula I to IV is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337: 525-31). when joined together (with a therapeutic peptide or polypeptide, an Fc domain can provide longer half-life (C. Huang, Curr. Opin. Biotechnol., 2009, 20, 692-699).

In one embodiment, the Fc-Peptide refers to a bioconjugate in which the Fc sequence is fused to the N-terminus of the peptide according to anyone of Formulae I to IV. In another embodiment, Peptide-Fc refers to a bioconjugate in which the Fc sequence is fused to the C-terminus of the peptide.

The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in PCT Publication No. WO 00/024782. This document discusses linkage to a "vehicle" such as polyethylene glycol (PEG), dextran, or an Fc region.

Preferred embodiments of the invention are bioconjugate comprising a peptide or polypeptide according to anyone of preceding embodiments and a half life extending moiety, wherein the half-life extending moiety is a Fc domain fused to a polypeptide of Formula I, III, IV or V via a linker. In one aspect of this invention, the linker has the following Formula: -[GGGGS]n-, n is 1, 2 or 3 (SEQ ID NO: 7) or the linker is GG or GS, and the polypeptide of Formula I, II, III or IV contains naturally occurring amino acids. Examples of polypeptides of Formula I, II, III or IV suitable for fusion with the Fc domain are: QRPC*LSC*KGPMPF (SEQ ID NO: 8), C*RPRLSC*KGPMPF (SEQ ID NO: 9) and QRC*RLSC*KGPMPF (SEQ ID NO: 10). One preferred aspect of this embodiments are Fc-Peptide fused bioconjugate as defined above, comprising a modified Fc fragment (e.g., all FcLALA) and a peptide or polypeptide of anyone of Formulae I to IV, as defined herein.

In yet another embodiment, the invention pertains to a bioconjugate according to any one of the preceding embodiments wherein the half-life extending moiety is a modified Fc domain wherein the C-terminal Lysine has been deleted or replaced with Alanine.

Peptides fused to an Fc region have been found to exhibit a substantially greater half-life in vivo than the unfused counterpart. Also, a fusion to an Fc region allows for dimerization/multimerization of the polypeptide.

In another embodiments of the invention are bioconjugate comprising a peptide or polypeptide according to anyone of Formulae I-IV and a half life extending moiety, wherein the half-life extending moiety is a Fc domain which is chemically linked to a polypeptide.

Preparing Conjugates:

Schemes 4 and 5 illustrate chemical reactions for conjugation of an APJ agonist peptide or a peptide according to anyone of Formula I to IV and a half-life extending moiety such as an Fc domain or albumin.

Scheme 4 illustrates the conjugation of a peptide-linker of Formula 4A with Cysteine 34 of Albumin Scheme 4

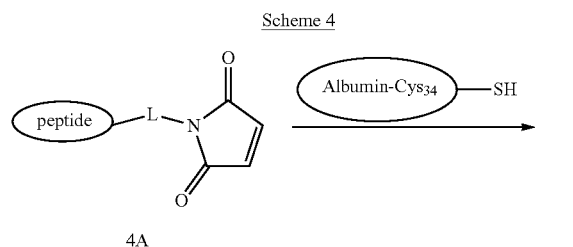

4A

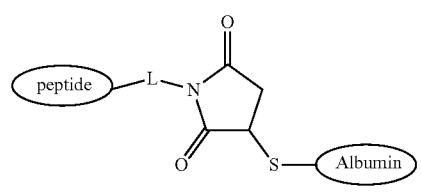

wherein L represent a linking moiety between the peptide and the maleimide functionality. In a particular embodiment, L is a linking moiety as disclosed in Scheme 1, 3A, 3B or 3C.

Scheme 5 illustrates the conjugation of a peptide-linker construct of Formula 8A with Cysteine 34 of Albumin.

Scheme 5

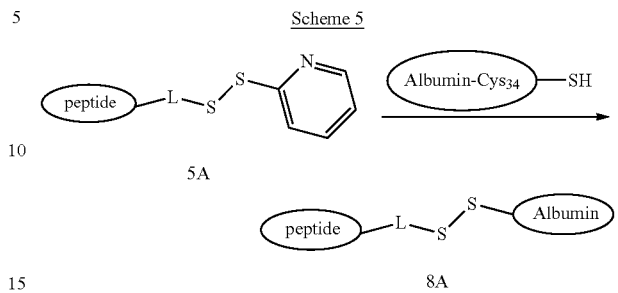

wherein L represents a linking moiety between the peptide and the —S—S-Pyridine functionality. In a particular embodiment, L is a linking moiety as disclosed in schemes 2, 3A, 3B or 3C.

Other method of conjugation have been described in co-filed application (U.S. provisional application No. 62/015,862, U.S. provisional application No. 62/015,868 and U.S. provisional application No. 62/015,848). Such method includes selective N-acylation of a peptide and is summarized in Scheme 6.

Scheme 6

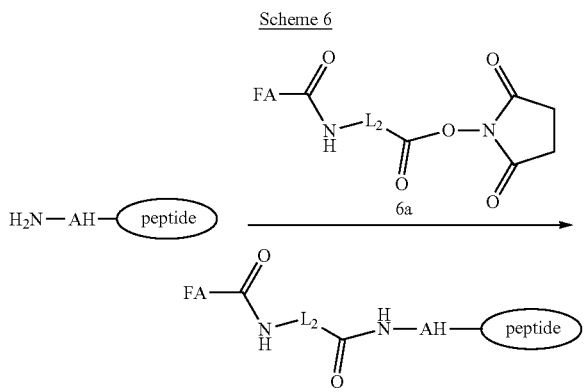

wherein AH- is a linker introduced on N-terminus of the peptide to facilitate reaction at the N-terminus, H is histidine, A is Alanine, FA is a fatty acid as described supra, for example a fatty acid of Formula A1 to A3, and L is a linking moieties (for example a PEG linking moiety). The Fatty acid Linker construct 6a (prepared as shown in Scheme 3G) is selectively introduced onto the peptide at the N-terminus when using low pH condition. Such method has been described in cofiled patent applications (U.S. provisional application No. 62/015,868 and U.S. provisional application No. 62/015,848).

Schemes 7 and 8 describes formation of conjugates according to the instant invention using click chemistry.

Scheme 7

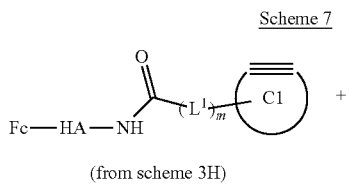

(from scheme 3H)

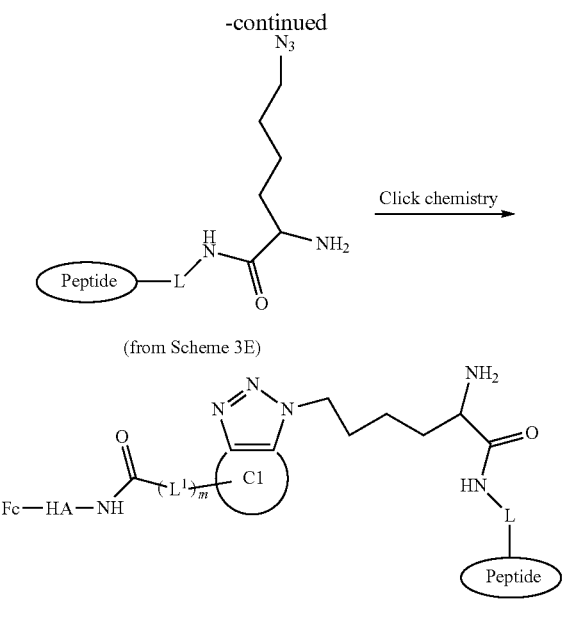

(from Scheme 3E)

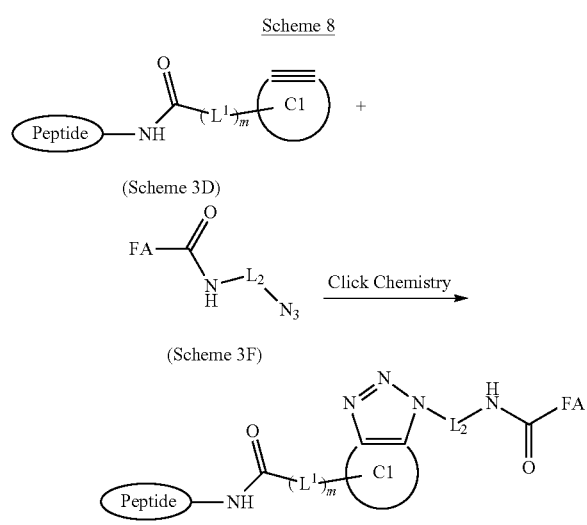

Methods for making conjugates and peptide-linker constructs as described in Schemes 1-5 have also been described and exemplified in co-filed US applications (U.S. provisional application No. 61/858,251 and U.S. provisional application No. 61/858,303) which are hereby incorporated by reference.

Scheme 9 describes the conjugation of an APJ peptide with a Fc construct using a sortase enzyme

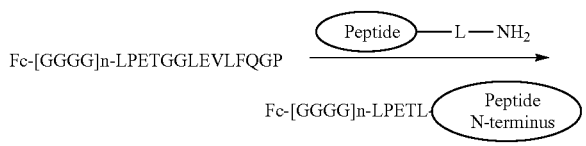

(SEQ ID NOS 17 and 11, respectively, in order of appearance) wherein n is 1, 2 or 3, L is an optional linker (for example a polyglycine linker)

Pharmaceutical Compositions

The polypeptides of the instant invention, or an amide, an ester of a salt thereof, or a bioconjugate thereof, may be administered in any of a variety of ways, including subcutaneously, intramuscularly, intravenously, intraperitoneally, intranasally, inhalationally, orally etc. Particularly preferred embodiments of the invention employ continuous intravenous administration of the polypeptides of the instant invention, or an amide, ester, or salt thereof or a bioconjugate thereof. The polypeptides or bioconjugates of the instant invention may be administered as a bolus or as a continuous infusion over a period of time. An implantable pump may be used. In certain embodiments of the invention, intermittent or continuous polypeptides or bioconjugates administration is continued for one to several days (e.g., 2-3 or more days), or for longer periods of time, e.g., weeks, months, or years. In some embodiments, intermittent or continuous polypeptide administration is provided for at least about 3 days. In other embodiments, intermittent or continuous polypeptide or bioconjugate administration is provided for at least about one week. In other embodiments, intermittent or continuous polypeptide or bioconjugate administration is provided for at least about two weeks. It may be desirable to maintain an average plasma polypeptide concentration above a particular threshold value either during administration or between administration of multiple doses. A desirable concentration may be determined, for example, based on the subject's physiological condition, disease severity, etc. Such desirable value(s) can be identified by performing standard clinical trials. Alternatively, the peptides and conjugates thereof could be delivered orally via FcRn mechanism. (Nat Rev Immunol. 7(9), 715-25, 2007; Nat Commun. 3; 3:610, 2012, Am J Physiol Gastrointest Liver Physiol 304: G262-G270, 2013).

In another aspect, the present invention provides a pharmaceutical composition comprising a polypeptide of the present invention or and amide, an ester or a salt thereof or a bioconjugate thereof, and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Pharmaceutical compositions suitable for injectable use typically include sterile aqueous solutions (where water soluble) or dispersions and sterile powders for the extemporaneous preparation of sterile injectable solutions or dispersion.

For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive therapeutic agents are preferably delivered in the form of an aerosol spray from pressured container or dispenser which contains a suitable propellant, e.g., a gas such as carbon dioxide, or a nebulizer. It is noted that the lungs provide a large surface area for systemic delivery of therapeutic agents.

The agents may be encapsulated, e.g., in polymeric microparticles such as those described in U.S. publication 20040096403, or in association with any of a wide variety of other drug delivery vehicles that are known in the art. In other embodiments of the invention the agents are delivered in association with a charged lipid as described, for example, in U.S. publication 20040062718. It is noted that the latter system has been used for administration of a therapeutic polypeptide, insulin, demonstrating the utility of this system for administration of peptide agents.

Systemic administration can also be by transmucosal or transdermal means.

Suitable compositions for transdermal application include an effective amount of a polypeptide of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable salts" refers to salts that retain the biological effectiveness and properties of the polypeptides of this invention and, which typically are not biologically or otherwise undesirable. In many cases, the polypeptides of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Method of the Invention:

Apelin family of peptides is the only known natural family of ligands for the G protein coupled APJ receptor. Apelin gene encodes a 77 aminoacid polypeptide, which gets processed into biologically active forms of apelin peptides, such as apelin-36, apelin-17, apelin-16, apelin-13, apelin-12 and pyroglutamate modified form of apelin-13 (Pyr$^1$-apelin-13). Any one of these apelin peptides, upon binding to APJ receptor, transduces the signal via Gi and Gq proteins. In cardiomyocytes, Gi or Gq coupling leads to changes in intracellular pH, PLC activation, and IP3 production that enhance myofilament calcium sensitivity and ultimately result in increased cardiac contractility. Gi coupling inhibits activated Gs, adenylyl cyclase and cAMP production and increases pAkt levels leading to cardioprotection. In vascular endothelial cells, APJ activation via Gi, pAKT leads to increased nitric oxide (NO) production, which increases smooth muscle relaxation resulting in overall vasodilation.

Patients with chronic stable heart failure have occasional acute episodes of decompensation, where cardiac contractility declines further and symptoms worsen. These exacerbations are referred to as acute decompensated heart failure (ADHF). Current therapies for ADHF include diuretics, vasodilators, and inotropes, which directly increase cardiac contractility. Current intravenous inotropes (dobutamine, dopamine, milrinone, levosimendan) are well known for their adverse events such as arrhythmia and increased long-term mortality. The synthetic apelin polypeptide analogs of the instant invention, or bioconjugate thereof, provide a therapy for ADHF that increases cardiac contractility without arrhythmogenic or mortality liabilities and address the enormous unmet medical need in chronic heart failure.

Indeed, acute apelin treatment (5 min) in humans results in coronary vasodilatation and improved cardiac output. However, native apelins exhibit a very short $t_{1/2}$ (seconds) and duration of action (few minutes) in vivo. The potent synthetic apelin peptide agonists of the instant invention, or bioconjugate thereof, have longer half lives compared to the native apelin.

Activation of APJ receptor in cardiomyocytes a) improve cardiac contractility via Gi/Gq, PLC and Ca2+, and b) provide cardioprotection via Gi, pAkt activation, but without increasing cAMP (as seen with other inotropes). In addition, APJ agonism in endothelial cells leads to arterial vasodilation, which further benefits heart failure by unloading the work of left ventricle. Taken together the synthetic apelin polypeptide analogs can improve overall cardiac function, reduce arrhythmogenesis and provide survival benefit.

More recently, there have been a number of preclinical research publications focusing on the potential involvement of Apelin in diabetes and insulin resistance. Apelin has been shown to 1) lower blood glucose levels by improving glucose uptake in muscle, adipose and heart, 2) protect pancreatic beta cells from ER stress and subsequent apoptosis, 3) lower the insulin secretion in beta cells, and 4) regulate catecholamine induced lypolysis in adipose tissue. Activation of pAKT pathway has been implicated in these processes.

The polypeptides according to anyone of formulae I to IV, or a pharmaceutically acceptable salt thereof, in free form or in pharmaceutically acceptable salt form, or a bioconjugate thereof, exhibit valuable pharmacological properties, e.g. APJ receptor agonsim properties, e.g. as indicated in in vitro and in vivo tests as provided in the next sections and are therefore indicated for therapy.

Polypeptides of the invention or a pharmaceutically acceptable salt thereof, or bioconjugates thereof, may be useful in the treatment of an indication selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Thus, as a further embodiment, the present invention provides the use of a polypeptide of anyone of formulae I to IV, or an amide, an ester or a salt thereof, or a bioconjugate thereof, for the treatment of a disease which is associated with the APJ receptor activity. In a further embodiment, the therapy is selected from a disease which is responsive to the agonism of the APJ receptor. In another embodiment, the disease is selected from the afore-mentioned list, suitably acute decompensated heart failure. In yet another subset of this embodiment, the present invention provides the use of a polypeptide of anyone of formulae I to IV, or an amide, ester or a salt thereof, or a bioconjugate thereof, in the manufacture of a medicament, for the treatment of a disease which is associated with the APJ receptor activity.

Thus, as a further embodiment, the present invention provides the use of a polypeptide of anyone of formulae I to IV, or an amide, an ester or a salt thereof, or a bioconjugate thereof, in therapy. In a further embodiment, the therapy is selected from a disease which may be treated by activation (agonism) of the APJ receptor.

In another embodiment, the invention provides a method of treating a disease which is responsive to the agonism of the APJ receptor, comprising administration of a therapeutically acceptable amount of a polypeptide of anyone of formulae I to IV, or an amide, an ester of a salt thereof, or a bioconjugate thereof. In a further embodiment, the disease is selected from the afore-mentioned list, suitably acute decompensated heart failure.

In yet another subset of this embodiment, the invention provides a method of treating a disease which is associated with the activity of the APJ receptor comprising administration of a therapeutically acceptable amount of a polypeptide of anyone of formulae I to IV, or an amide, an ester or a salt thereof or a bioconjugate thereof.

The effective amount of a pharmaceutical composition or combination of the invention to be employed therapeutically will depend, for example, upon the therapeutic context and objectives. One skilled in the art will appreciate that the appropriate dosage levels for treatment will thus vary depending, in part, upon the molecule delivered, the indication for which the fusion protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The term "a therapeutically effective amount" of a polypeptide of the present invention or a bioconjugate thereof, refers to an amount of the polypeptide of the present invention (or bioconjugate) that will elicit the biological or medical response of a subject, for example, amelioration of a symptom, alleviation of a condition, slow or delay disease progression, or prevention of a disease, etc. In one non-limiting embodiment, the term "a therapeutically effective amount" refers to the amount of the polypeptide of the present invention that, when administered to a subject, is effective to (1) at least partially alleviate, inhibit, prevent and/or ameliorate a condition, a disorder or a disease or a symptom thereof (i) ameliorated by the activation of the APJ receptor or (ii) associated with the activity of the APJ receptor, or (iii) characterized by abnormal activity of the APJ receptor; or (2) activate the APJ receptor.

In another non-limiting embodiment, the term "a therapeutically effective amount" refers to the amount of the polypeptide of the present invention that, when administered to a cell, or a tissue, or a non-cellular biological material, or a medium, is effective to at least partially activate the APJ receptor. As will be appreciated by those of ordinary skill in the art, the absolute amount of a particular agent that is effective may vary depending on such factors as the desired biological endpoint, the agent to be delivered, the target tissue, etc. Those of ordinary skill in the art understand that "a therapeutically effective amount" may be administered in a single dose or may be achieved by administration of multiple doses. For example, in the case of an agent to treat heartfailure, an effective amount may be an amount sufficient to result in clinical improvement of the patient, e.g., increased exercise tolerance/capacity, increased blood pressure, decrease fluid retention, and/or improved results on a quantitative test of cardiac functioning, e.g., ejection fraction, exercise capacity (time to exhaustion), etc.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the terms "prevent", "preventing" and "prevention" refer to the prevention of the recurrence, onset, or development of one or more symptoms of a disorder in a subject resulting from the administration of a therapy (e.g., a therapeutic agent), or the administration of a combination of therapies (e.g., a combination of therapeutic agents).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The activity of a polypeptide according to the present invention can be assessed by the following in vitro methods described below.

hAPJ Calcium Flux Assay:

Chem-5 APJ stable cells (Millipore # HTS068C) were plated in 384-well format with 10,000 cells/well in 25 ul growth media, then grown 24 hours in a 37° C. tissue culture incubator. One hour before the assay, 25 ul/well FLIPR Calcium 4 dye (Molecular Devices R8142) with 2.5 mM probenecid was added, and cells were incubated one hour in a 37° C. tissue culture incubator. Peptides were solubilized in HBSS, HEPES & 0.1% BSA buffer, and serially-diluted 10-fold, from 50 uM to 5 pM, in triplicate. FLIPR Tetra was used to add peptide to the cells with dye (1:5, for final peptide concentrations ranging from 10 uM to 1 pM). FLIPR dye inside the cells emitted fluorescence after binding to calcium, while fluorescence from outside the cells was masked. Fluorescence was measured using 470-495 excitation and 515-575 emission wavelengths on the FLIPR Tetra. Readings were done for 3 minutes total, beginning 10 seconds before the peptide addition. Maximum-minimum values were calculated and plotted for each peptide concentration, and GraphPad prism software was used to calculate $EC_{50}$ values at the curve inflection points, for calcium flux stimulation by peptides.

Plasma Stability Assay:

Materials:

Working solution: 1 mg/mL test article is prepared in Milli-Q water

Extraction solution: Methanol:Acetonitrile:Water (1:1:1) with 0.1% Formic Acid and 400 ng/mL Glyburide.

Plasma: Male Sprague-Dawley rat plasma (with sodium heparin), purchased from Bioreclamation LLC (Liverpool, N.Y.). Whole blood: Male Sprague Dawley whole blood (with sodium heparin), purchased from Bioreclamation LLC (Liverpool, N.Y.)

Lung homogenate: Male rat Sprague Dawley lung was purchased from Bioreclamation LLC (Liverpool, N.Y.). The lung was homogenized using polytron homogenizer after addition of 5× volume of 1×PBS. The homogenate was centrifuged at 9000 rpm for 10 min at 4° C. The supernatant was centrifuged again at 3000 rpm for 30 min to make a clear supernatant. Protein concentration was determined using a commercial kit (Pierce, Thermo Scientific).

Sample Preparation Procedure: (Peptides)

Test article was prepared in one of the following biological matrices: heparinized rat plasma, heparinized rat whole blood or lung homogenate. The plasma and whole blood sample was prepared at 5000 ng/mL by adding 5 uL of 1 mg/mL Working solution to 995 uL of rat plasma or whole blood. Lung homogenate samples were prepared by diluting lung homogenate to 1 mg/ml protein concentration with phosphate buffered saline (PBS), followed by addition of 5 uL Working solution to 995 uL diluted lung homogenate. The samples were incubated at 37° C. with gentle shaking (65~75 rpm) in a water bath incubator. At times 0 min, 5 min, 15 min, 30 min, 60 min, 120 and 240 min, 25 uL aliquots of incubation samples were transferred to 96-well plate and immediately protein precipitated using 150 uL of Extraction solution. After completion of incubation experiment, the sample plate was centrifuged at 4000 rpm at 4° C. for 10 minutes. Afterwards, a pipetting device (Tecan Temo) was used to transfer the supernatants to another plate and add 50 uL of water to all samples. The plate was vortexed prior to LC-MS analysis.

Sample Preparation Procedure (Conjugates)

Test article is prepared at 50,000 ng/mL by adding 5 uL of 1 mg/mL Working solution to 495 uL of rat plasma. The samples are incubated at 37° C. with gentle shaking (65-75 rpm) in a water bath incubator. At times 0 hr, 0.5 hr, 1 hr, 2 hr, 4 hr, 6 and 24 hr, 50 uL aliquots of incubation samples are transferred to 96-well plate and 100 uL 40 mM TCEP (tris(2-carboxyethyl)phosphine) are added to each sample. The reaction mixture is incubated at 37° C. for 1 hour. After completion of reaction, protein precipitation is performed using 300 uL of acetonitrile. The sample plate is centrifuged at 4000 rpm at 4° C. for 10 minutes. Afterwards, a pipetting device (Tecan Temo) is used to transfer 125 uL supernatants to another plate and adds 50 uL of water to all samples. The plate is vortexed prior to LC-MS analysis.

LC-MS Analysis of Stability Samples

HPLC: Agilent 1290 HPLC with autosampler

Column: MAC-MOD ACE C18, 3 μm, 30 mm×2.1 mm i.d.

Mobile phase A: 0.1% Formic acid in acetonitrile

Mobile phase B: 0.1% Formic acid in water

Gradient Program:

| Time (min) | Flow (mL) | Mobile Phase A(%) | Mobile Phase B(%) |
|---|---|---|---|
| 0 | 0.4 | 95 | 5 |
| 0.5 | 0.4 | 95 | 5 |
| 1.5 | 0.4 | 5 | 95 |
| 4.1 | 0.4 | 5 | 95 |
| 4.2 | 0.4 | 95 | 5 |
| 5 | 0.4 | 95 | 5 |

Mass spectrometer: Agilent Q-TOF 6530

Data acquisition mode: Full scan with mass range of 100-1000 m/z

Data acquisition and analysis software: MassHunter

Data Analysis:

Stability assay: stability half-life, (t ½), values were determined by converting peak areas at each time point to percent remaining relative to initial (t=0) peak area.

Percent remaining=100×(sample peak area)÷(t=0 peak area)

The natural log of percent remaining values were calculated and plotted against sample time (Microsoft Excel). The slope of this line, k, was determined by linear regression (Microsoft Excel).

Stability half-life was then calculated by the formula, t ½=0.693÷k

Surrogate Activity-Based Plasma Stability Assay:

The calcium flux protocol described above was followed, with the following changes. The peptides were also incubated with 5% rat plasma (Bioreclamation # RATPLNAHP-M, Na Heparin-treated). Readings were taken at time points $t_0$ and $t_{24}$ hrs, after incubation in a 37° C. tissue culture incubator. Peptide plasma half-life in minutes was estimated by calculating the following:

1) $LN((EC_{50}$ at $t_0)/(EC_{50}$ at $t_{24\ hrs}))$,

2) Calculate slope of value above and

3) $t_{1/2}=0.693/(slope\hat{\ }2)$.

Using the test assay (as described above) polypeptides of the invention exhibited efficacy and stability in accordance to Tables 2 and 3, provided infra.

TABLE 2

Activity and stability of polypeptides

| Peptide | hAPJ Ca$^{2+}$ Flux EC$_{50}$ [nM] | Surrogate activity-based Plasma stability t½ [min] |
|---|---|---|
| Example 1 | 9.4 | 8 |
| Example 2 | 3.2 | 39 |
| Example 3 | 64.5 | n.d. |
| Example 4 | 74.6 | 506 |
| Example 5 | 1.6 | 5.0 |
| Example 6 | 21.4 | 5 |
| Example 7 | 11.8 | 9 |
| Example 8 | 13.1 | 662.5 |
| Example 9 | 23.4 | 109.2 |
| Example 10 | 46.9 | 57.4 |
| Example 11 | 32.2 | 32.8 |
| Example 12 | 21.4 | 10 |
| Example 13 | 12.2 | 10 |
| Example 14 | 48.7 | 7.5 |
| Example 15 | 193.5 | 17.7 |
| Example 16 | 14.1 | 7 |
| Example 17 | 410.3 | 11.4 |
| Example 18 | 174 | 50 |
| Example 19 | 79.3 | 50 |
| Example 20 | 1.0 | 11.9 |
| Example 21 | 2.9 | >1000 |
| Example 22 | 3.3 | >1000 |
| Example 23 | 72.2 | 3157 |
| Example 24 | 85.8 | 1699 |
| Example 25 | 227 | >1000 |
| Example 26 | 2292 | 52 |
| Example 27 | 86.5 | 82 |
| Example 28 | 3.1 | 13 |
| Example 29 | 4.2 | 705.0 |
| Example 30 | 0.4 | 660.7 |
| Example 31 | 0.5 | 43.1 |
| Example 32 | 3.0 | >1000 |
| Example 33 | 1.9 | >1000 |
| Example 34 | 0.6 | >1000 |
| Example 35 | 2.0 | 155.0 |
| Example 35 | 66.7 | 8 |
| Example 36 | 4.2 | 34 |
| Example 37 | 937 | 47 |
| Example 38 | 175 | 41 |
| Example 40 | 2479 | >1000 |
| Example 41 | 839 | >1000 |
| Example 42 | 16.3 | >1000 |
| Example 43 | 28.9 | >1000 |
| Comparative Example: Pyr1-apelin-13 | 1.8 | 5.0 |

TABLE 3

Correlation between plasma stability assay and surrogate activity based plasma stability assay:

| Peptide | Plasma stability t½ [min] | Surrogate Activity based Plasma stability t½ [min] |
|---|---|---|
| Pyr-1-Apelin 13 | 6.6 | 5.0 |
| Ex 32 | 377 | >1000 |

The polypeptide of the present invention or bioconjugates thereof may have an APJ receptor potency similar to apelin-13 or pyr-1-apelin-13. In one embodiment the polypeptide of the present invention or bioconjugate thereof has an EC$_{50}$ of less than 100 nM. In another embodiment the polypeptide of the invention, or bioconjugate thereof, has an EC$_{50}$ of less than 50 nM, preferably less than 25 nM and more preferably less than 15 nM. In yet another embodiment, the polypeptide of the present invention or a bioconjugate thereof has an EC$_{50}$ of less than 10 nM.

The polypeptide of the present invention, or bioconjugate thereof, may have plasma stability superior to apelin-13 or pyr-1-apelin-13. In one embodiment, the plasma stability improvement is at least 2 fold. In one embodiment, the polypeptide of the invention, or a bioconjugate thereof, has a plasma stability of at least 30 minutes. In another embodiment, the polypeptide of the invention, or a bioconjugate thereof, has a plasma stability of at least 60 minutes, or at least 80 min, preferably at least 100 minutes and more preferably at least 150 minutes.

The polypeptide of the present invention, or a bioconjugate thereof, may be administered either simultaneously with, or before or after, one or more other therapeutic agent. The polypeptide or bioconjugate of the present invention may be administered separately, by the same or different route of administration, or together in the same pharmaceutical composition as the other agents.

In one embodiment, the invention provides a product comprising a polypeptide of anyone of formulae I to IV, or an amide, an ester of a salt thereof, or a bioconjugate thereof, and at least one other therapeutic agent as a combined preparation for simultaneous, separate or sequential use in therapy. In one embodiment, the therapy is the treatment of a disease or condition responsive to the activation of the APJ receptor.

Products provided as a combined preparation include a composition comprising a polypeptide of anyone of formulae I to IV, or an amide, an ester of a salt thereof, or a bioconjugate thereof, and the other therapeutic agent(s) together in the same pharmaceutical composition, or a polypeptide of anyone of formulae I to IV, or an amide, an ester or a salt thereof, or a bioconjugate thereof, and the other therapeutic agent(s) in separate form, e.g. in the form of a kit.

In one embodiment, the invention provides a pharmaceutical composition comprising a polypeptide of anyone of formulae I to IV, or an amide, an ester or a salt thereof, or a bioconjugate thereof and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a polypeptide of anyone of formula I to IV, or an amide, an ester or a salt thereof or a bioconjugate thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the peptide or bioconjugate of the invention and the other therapeutic agent may be manufactured and/or formulated by the same or different manufacturers. Moreover, the peptide or bioconjugate of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of a polypeptide or bioconjugate of the invention and the other therapeutic agent.

Accordingly, the invention provides the use of a polypeptide of anyone of formulae I to IV, or an amide, an ester or a salt thereof, or a bioconjugate thereof, for treating a disease or condition responsive to the agonism of the APJ receptor, wherein the medicament is prepared for administration with another therapeutic agent. The invention also provides the use of another therapeutic agent for treating a disease or condition responsive to the agonism of the apelin receptor, wherein the medicament is administered with a polypeptide of anyone of formulae I to IV, or an amide, an ester or a salt thereof or a bioconjugate thereof.

The invention also provides a polypeptide of anyone of formulae I to IV, or a pharmaceutically acceptable salt thereof, or a bioconjugate thereof, for use in a method of treating a disease or condition responsive to the agonism of the APJ receptor, wherein the polypeptide of anyone of formulae I to IV, or an amide, an ester or a salt thereof, or bioconjugate thereof, is prepared for administration with another therapeutic agent. The invention also provides another therapeutic agent for use in a method of treating a disease or condition responsive to the agonism of the APJ receptor, wherein the other therapeutic agent is prepared for administration with a polypeptide of anyone of formulae I to IV, or an amide, an ester or a salt thereof, or a bioconjugate thereof. The invention also provides a polypeptide of anyone of formulae I to IV, or an amide, an ester or a salt thereof, or a bioconjugate thereof, for use in a method of treating a disease or condition responsive to the agonism of the APJ receptor, wherein the polypeptide of anyone of formulae I to IV, or an amide, an ester or a salt thereof, or a bioconjugate thereof, is administered with another therapeutic agent. The invention also provides another therapeutic agent for use in a method of treating a disease or condition responsive to the agonism of the APJ receptor, wherein the other therapeutic agent is administered with a polypeptide of anyone of formulae I to IV or an amide, an ester or a salt thereof or a bioconjugate thereof.

The invention also provides the use of a polypeptide of anyone of formulae I to IV, or an amide, an ester or a salt thereof, or a bioconjugate thereof, for treating a disease or condition responsive to the agonism of the APJ receptor, wherein the patient has previously (e.g. within 24 hours) been treated with another therapeutic agent. The invention also provides the use of another therapeutic agent for treating a disease or condition responsive to the agonism of the APJ receptor, wherein the patient has previously (e.g. within 24 hours) been treated with a polypeptide of anyone of formulae I to IV, or an amide, an ester or a salt thereof, or a bioconjugate thereof.

In one embodiment, the other therapeutic agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

The term "in combination with" a second agent or treatment includes co-administration of the polypeptide or bioconjugate of the invention (e.g., a polypeptide according to anyone of Formulae I-IV or a polypeptide otherwise described herein) with the second agent or treatment, administration of the compound of the invention first, followed by the second agent or treatment and administration of the second agent or treatment first, followed by the peptide to bioconjugate of the invention.

The term "second agent" includes any agent which is known in the art to treat, prevent, or reduce the symptoms of a disease or disorder described herein, e.g. a disorder or disease responsive to the activation of the APJ receptor, such as for example, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Examples of second agents include inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

Inotropes as used herein include for example dobutamine, isoproterenol, milrinone, amirinone, levosimendan, epinephrine, norepinephrine, isoproterenol and digoxin.

Beta adrenergic receptor blockers as used herein include for example acebutolol, atenolol, betaxolol, bisoprolol, carteolol, metoprolol, nadolol, propranolol, sotalol and timolol.

Anti-coagulants as used herein include Dalteparin, Danaparoid, Enoxaparin, Heparin, Tinzaparin, Warfarin.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or, pharmaceuticals salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-m ethylhexyl]-alfa-

[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

(A)
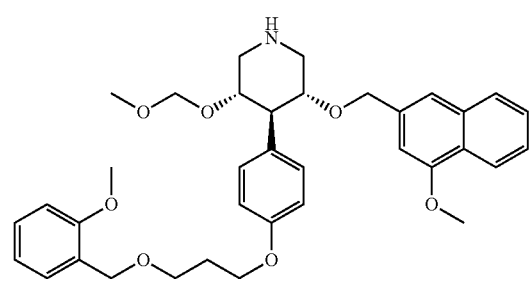

and (B)
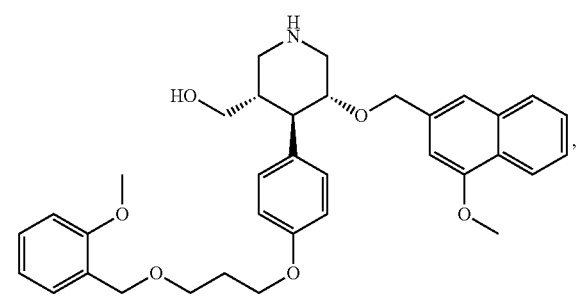

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "calcium channel blocker (CCB)" includes dihydropyridines (DHPs) and non-DHPs (e.g., diltiazem-type and verapamil-type CCBs). Examples include amlodipine, Bepridil, Diltiazem, felodipine, ryosidine, isradipine, lacidipine, nicardipine, nifedipine, niguldipine, niludipine, nimodipine, nisoldipine, nitrendipine, Verapamil and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F) (SEQ ID NO: 18)

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

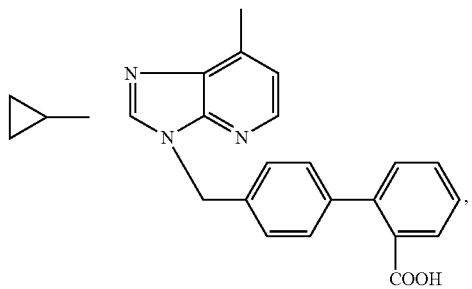

the compound with the designation SC-52458 of the following formula

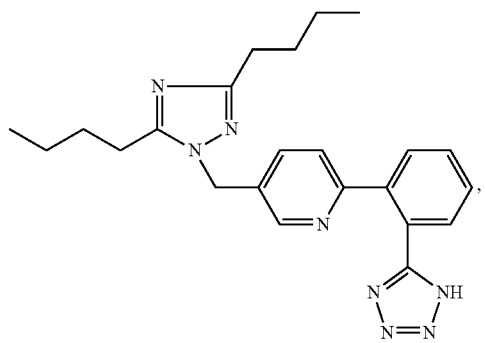 [SMILES: CCCCc1nc(CCCC)n(Cc2ccc(-c3ccccc3-c3nnn[nH]3)nc2)n1]

and the compound with the designation ZD-8731 of the following formula

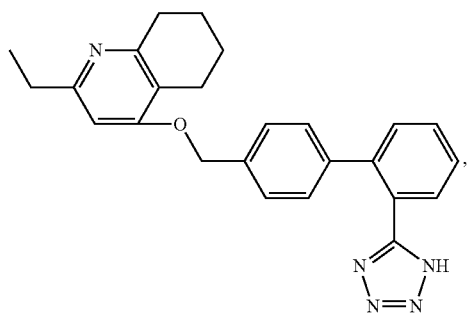 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are candesartan, eprosartan, irbesartan, losartan, telmisartan, valsartan. Also preferred are those agents which have been marketed, most preferred is valsartan or a pharmaceutically acceptable salt thereof.

The term "anti-diabetic agent" includes insulin secretion enhancers that promote the secretion of insulin from pancreatic-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

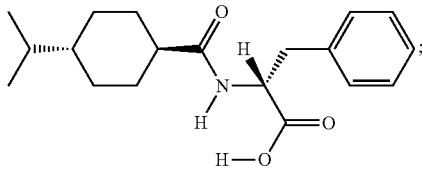

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058).

Further examples of second agents with which the peptide and polypeptide of the invention can be used in combination include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV (dipeptidyl peptidase IV) inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 (glucagon like peptide-1) is an insulinotropic protein which is described, e.g., by W. E. Schmidt et al. in Diabetologia, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

In one embodiment, the invention provides a combination, in particular a pharmaceutical combination, comprising a therapeutically effective amount of the polypeptide according to the definition of anyone of formulae I to IV, or an amide, an ester, a salt thereof, or a bioconjugate thereof, and one or more therapeutically active agents selected from β-adrenergic receptor blockers such as acebutolol, atenolol, betaxolol, bisoprolol, metoprolol, nadolol, propranolol, sotalol and timolol; angiotensin II receptor antagonists such as AT1 blockers; antidiabetic agents such as DPPIV inhibitors (e.g. vildagliptin) and GLP1 peptide agonist.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. An example of non-steroidal aldosterone synthase inhibitor is the (+)-enantiomer of the hydrochloride of fadrozole (U.S. Pat. Nos. 4,617,307 and 4,889,861) of formula

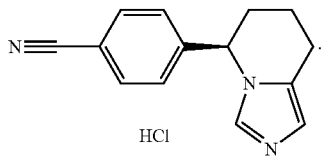 [SMILES: N#Cc1ccc([C@H]2CCCc3cncn32)cc1 ; Cl]

or, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-(7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl(5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan and ambrisentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in J. Antibiot., 49(8): 815-816 (1996), and Bioorg. Med. Chem. Lett.; 6:1951-1954 (1996), respectively. Furthermore, the CETP inhibitors also include those disclosed in WO2000/017165, WO2005/095409, WO2005/097806, WO 2007/128568, WO2008/009435, WO 2009/059943 and WO2009/071509.

The term "NEP inhibitor" refers to a compound that inhibits neutral endopeptidase (NEP) EC 3.4.24.11. Examples include Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester or a pharmaceutically acceptable salt thereof. NEP inhibitors also include Phosphono/biaryl substituted dipeptide derivatives, as disclosed in U.S. Pat. No. 5,155,100. NEP inhibitors also include N-mercaptoacyl phenylalanine derivative as disclosed in PCT application Number WO 2003/104200. NEP inhibitors also include dual-acting antihypertensive agents as disclosed in PCT application Numbers WO 2008/133896, WO 2009/035543 or WO 2009/134741. Other examples include compounds disclosed in U.S. application Ser. Nos. 12/788,794; 12/788,766 and 12/947,029. NEP inhibitors also include compounds disclosed in WO 2010/136474, WO 2010/136493, WO 2011/061271 and U.S. provisional applications No. 61/414,171 and 61/414,163.

In one embodiment, the invention provides a method of activating the APJ receptor in a subject, wherein the method comprises administering to the subject a therapeutically effective amount of the polypeptide according to the definition of anyone of formulae I to IV, or an amide, an ester or a salt thereof or a bioconjugate thereof.

In one embodiment, the invention provides a method of treating a disorder or a disease responsive to the activation of the APJ receptor, in a subject, wherein the method comprises administering to the subject a therapeutically effective amount of the polypeptide according to the definition of anyone of formulae I to IV, or an amide, an ester or a salt thereof or a bioconjugate thereof.

In one embodiment, the invention provides a method of treating a disorder or a disease responsive to the activation (agonism) of the APJ receptor, in a subject, wherein the disorder or the disease is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In one embodiment, the invention provides a polypeptide according to the definition of anyone of formulae I to IV, or a bioconjugate thereof, for use as a medicament.

In one embodiment, the invention provides the use of a polypeptide according to the definition of anyone of formulae I to IV, or an amide, an ester or a salt thereof, or a bioconjugate thereof, in the manufacture of a medicament, for the treatment of a disorder or disease responsive to the activation of the APJ receptor. In another embodiment, the invention provides the use of a polypeptide according to the definition of anyone of formulae I to IV, or an amide, an ester or a salt thereof, or a bioconjugate thereof, in the manufacture of a medicament, for the treatment of a disorder or disease responsive to the activation of the APJ receptor, wherein said disorder or disease is in particular selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Exemplification of the Invention: Peptide and Polypeptide Synthesis

| Abbreviation | Definition |
| --- | --- |
| AA | Amino acid |
| Ac | Acetyl |
| Acm | Acetamidomethyl |
| ACN | Acetonitrile |
| AcOH | Acetic acid |
| $Ac_2O$ | Acetic anhydride |
| ε-Ahx | ε-Amino hexanoic acid |
| AM | Aminomethyl |
| BAL | Backbone amide linker |
| BSA | Bovine Serum Albumin |
| Boc | tert-Butyloxycarbonyl |
| Bzl | Benzyl |
| DCM | Dichlormethane |
| DIC | N,N'-Diisopropylcarbodiimide |
| DIPEA | N,N'-Diisopropylethylamine |
| DMA | N,N'-Dimethylacetamide |
| DMF | N,N'-Dimethylformamide |
| DMSO | Dimethylsulfoxide |
| DTT | Dithiothreitol |
| DVB | Divinylbenzene |
| EDT | Ethanedithiol |
| FA | Formic acid |
| Fmoc | 9-Fluorenylmethyloxycarbonyl |
| HATU | 2-(1H-9-Azabenzotriazole-1-yl)-1,1,3,3-tetramethyluronium hexafluorophosphate |
| HBSS | Hank's buffered salt solution |
| HCTU | 2-(6-Chloro-1H-Benzotriazole-yl)-1,1,3,3-tetramethyluronium hexafluorophosphate |
| HEPES | 4-(2-hydroxyethyl)-1-piperazineethanesulfonic acid |
| HFIP | Hexafluoroisopropanol |
| HOAt | 1-Hydroxy-7-azabenzotriazole |
| HSA | Human serum albumin |
| HPLC | High performance liquid chromatography |
| HRMS | High resolution mass spectrometry |
| ivDde | (4,4-Dimethyl-2,6-dioxocyclohex-1-ylidene)-3-methylbutyl |
| LN | Logarithmus naturali (natural logarithm) |
| MeOH | Methanol |
| MS | Mass spectrometry |
| Nal | 2-Naphthylalanine |
| Nle | Norleucine |

| Abbreviation | Definition |
| --- | --- |
| NMP | N-Methylpyrrolidine |
| Oxyma Pure | Ethyl 2-cyano-2-(hydroxyimino)acetate |
| Pbf | 2,2,4,6,7-Pentamethyldihydrobenzofuran-5-sulfonyl |
| pE | Pyroglutamate |
| PG | Protecting group |
| PBS | Phosphate buffered saline |
| Ph | Phenyl |
| PhP | Phenylproline |
| Pip | Pipecolic acid |
| Pol | Polymeric support |
| PS | Polystyrene |
| rt | Room temperature |
| SEC | Size exclusion chromatography |
| SPPS | Solid phase peptide synthesis |
| TBME | tert-Butylmethylether |
| TCEP | Tris(2-carboxyethyl)phosphine |
| tBuOH | tert-Butanol |
| TFA | Trifluoroacetic acid |
| THF | Tetrahydrofuran |
| TIS, TIPS | Triisopropylsilane |
| $t_R$ | Retention time |
| Trt | Trityl |
| UPLC | Ultra performance liquid chromatography |
| UV | Ultraviolet |

The peptides were synthesized by standard solid phase Fmoc chemistry. The peptides were assembled on the Prelude™ peptide synthesizer (Protein Technologies, Inc., Tucson, USA) and Liberty microwave peptide synthesizer (CEM Corporation, North Carolina, USA). Peptides with a free carboxylic acid on the C-terminus or with an N,N-disubstituted carboxamide on the C-terminus were synthesized from 2-chlorotrityl chloride-PS-resin (ABCR, Karlsruhe, Germany or AnaSpec, Inc., California, USA). Peptides with an unsubstituted carboxamide on the C-terminus were synthesized from Fmoc protected Rink-Amide-AM-PS-resin (Merck, Darmstadt, Germany). Peptides with an N-monosubstituted carboxamide on the C-terminus were synthesized from BAL-AM-PS-resin loaded with amines (EMC Microcollections, Tübingen, Germany).

The peptides were purified by preparative reversed-phase HPLC. The following columns were used:

Waters SunFire Prep C18 OBD Column, 5 µm, 30×100 mm, Part No. 186002572 (one column or two columns in series)

Waters Atlantis Prep OBD T3 Column, 5 µm, 30×150 mm, Part No. 186003703

Waters SunFire Prep C18 OBD Column, 5 µm, 30×50 mm, Part No. 186002572

Mobile phases consisted of eluent A (0.1% TFA in $H_2O$) and eluent B (ACN). Gradients were designed based on the specific requirements of the separation problem. Pure products were lyophilized from ACN/$H_2O$.

The products were analyzed by analytical HPLC using UV detection at λ=214 nm and UPLC-MS using electrospray ionization.

The peptides that are exemplified in Table 4 were synthesized using the general procedures described below. Unsubstituted N- or C-termini are indicated by italic H— or —OH, respectively.

TABLE 4

| Example | Sequence | SEQ ID NO: |
| --- | --- | --- |
| Example 1 | Ac-C*-R-P-R-L-S-C*-K-G-P-Nle-P-F-OH | 19 |
| Example 2 | Ac-C*-R-P-R-L-S-C*-K-G-P-Nle-P-NH(Phenethyl) | 20 |
| Example 3 | Ac-C*-R-P-R-L-S-C*-K-G-P-Nle-P-(N-Me)F-OH | 21 |
| Example 4 | Ac-C*-R-P-R-L-S-C*-K-G-P-Nle-P-NH₂ | 22 |
| Example 5 | Ac-C*-R-P-R-L-S-C*-K-G-P-Nle-P-Nal-OH | 23 |
| Example 6 | Ac-C*-R-P-R-L-S-hC*-K-G-P-Nle-P-F-OH | 24 |
| Example 7 | Ac-hC*-R-P-R-L-S-hC*-K-G-P-Nle-P-F-OH | 25 |
| Example 8 | Ac-C*-R-P-R-L-S-C*-K-G-P-Nle-P-a-OH | 26 |
| Example 9 | Ac-C*-R-P-R-L-S-C*-K-G-P-Nle-P-NMe(Phenethyl) | 27 |
| Example 10 | Ac-C*-R-P-R-L-S-C*-K-G-P-Nle-P-f-OH | 28 |
| Example 11 | Ac-C*-R-P-R-L-S-C*-K-G-P-Nle-NH(Phenethyl) | 29 |
| Example 12 | Ac-c*-R-P-R-L-S-C*-K-G-P-Nle-P-F-OH | 30 |
| Example 13 | Ac-c*-R-P-R-L-S-hC*-K-G-P-Nle-P-F-OH | 31 |
| Example 14 | Ac-c*-R-P-R-L-S-c*-K-G-P-Nle-P-F-OH | 32 |
| Example 15 | Ac-C*-R-P-R-L-S-c*-K-G-P-Nle-P-F-OH | 33 |
| Example 16 | Ac-(D-hC)*-R-P-R-L-S-hC*-K-G-P-Nle-P-F-OH | 34 |
| Example 17 | Ac-(D-hC)*-R-P-R-L-S-(D-hC)*-K-G-P-Nle-P-F-OH | 35 |
| Example 18 | Ac-(D-hC)*-R-P-R-L-S-(hC)*-K-G-P-f-a-f-OH | 36 |
| Example 19 | Ac-c-R-P-R-L-S-(hC)-K-G-P-(D-Nle)-a-f-OH | 37 |
| Example 20 | pE-R-C*-R-L-S-C*-K-G-P-Nle-P-F-OH | 38 |
| Example 21 | pE-R-C*-R-L-S-C*-K-G-P-(D-Nle)-a-f-OH | 39 |
| Example 22 | pE-R-C*-R-L-S-C*-F-G-P-(D-Nle)-a-f-OH | 40 |
| Example 23 | pE-R-C*-R-L-S-C*-K-a-P-(D-Nle)-a-f-OH | 41 |
| Example 24 | pE-R-C*-R-L-S-C*-K-A-P-(D-Nle)-a-f-OH | 42 |
| Example 25 | pE-R-C*-R-L-S-C*-K-G-P-(D-Nle)-NH₂ | 43 |
| Example 26 | pE-R-C*-R-L-S-(D-hC)*-K-G-P-f-a-f-OH | 44 |
| Example 27 | pE-R-c*-R-L-S-C*-K-G-P-(D-Nle)-(D-abu)-f-OH | 45 |
| Example 28 | pE-R-P-C*-L-S-C*-K-G-P-Nle-P-F-OH | 46 |
| Example 29 | pE-R-P-C*-L-S-C*-K-G-P-Nle-P-(N-Me)F-OH | 47 |
| Example 30 | pE-R-P-C*-L-S-C*-K-G-P-Nle-P-NH(Phenethyl) | 48 |
| Example 31 | pE-R-P-C*-L-S-C*-K-G-P-Nle-NH(Phenethyl) | 49 |
| Example 32 | pE-R-P-C*-L-S-C*-K-G-P-(D-Nle)-NH(Phenethyl) | 50 |
| Example 33 | pE-R-P-C*-L-S-C*-K-G-P-(D-Nle)-a-f-OH | 51 |
| Example 34 | pE-R-P-C*-L-S-C*-K-G-P-(D-Nle)-f-OH | 52 |

TABLE 4-continued

| Example | Sequence | SEQ ID NO: |
|---|---|---|
| Example 35 | pE-R-P-C*-L-S-C*-F-G-P-(D-Nle)-a-f-OH | 53 |
| Example 35 | H-R-P-C*-L-S-C*-K-(D-Nle)-a-f-OH | 54 |
| Example 36 | pE-R-P-hC*-L-S-C*-K-G-P-f-a-f-OH | 55 |
| Example 37 | pE-R-P-c*-L-S-(D-hC)*-K-G-P-(D-Nle)-a-y-OH | 56 |
| Example 38 | pE-R-P-(D-hC)*-L-S-hC*-K-G-P-(D-Nle)-(D-Nva)-f-OH | 57 | wherein the two amino acids labeled with "*" represent the amino acids forming a disulfide or amide bond via their side chain.

Analytical Methods

1a) HPLC—Analytical Method A

Column: Waters Xbridge™ C18 (50×4.0 mm), 3.5 μm; Part no: 186003031

Eluent A: 0.07% TFA in water/Eluent B: 0.1% TFA in ACN

Flow: 1.5 ml/min

Temperature: 40° C.

Gradient:

| Time [min] | A [%] | B [%] |
|---|---|---|
| 0.0 | 95 | 5 |
| 10.0 | 0 | 100 |
| 12.0 | 0 | 100 |
| 12.2 | 95 | 5 |

1b) HPLC—Analytical Method B

Column: XBridge BEH300 C18 (100×4.6 mm), 3 μm; Part no: 186003612

Eluent A: 0.1% TFA in water/Eluent B: 0.1% TFA in ACN

Flow: 1.0 ml/min

Temperature: 40° C.

Gradient:

| Time [min] | A [%] | B [%] |
|---|---|---|
| 0.0 | 98 | 2 |
| 18 | 2 | 98 |
| 20 | 2 | 98 |
| 22 | 98 | 2 |

2a) UPLC-MS—Analytical Method C

Column: Acquity UPLC® BEH300 C18 (50×2.1 mm), 1.7 μm; Part no: 186003685

Eluent A: 0.05% TFA in water/Eluent B: 0.04% TFA in ACN

Flow: 1.0 ml/min

Temperature: 80° C.

Gradient:

| Time [min] | A [%] | B [%] |
|---|---|---|
| 0.0 | 100 | 0 |
| 0.2 | 100 | 0 |
| 4.4 | 2 | 98 |
| 4.8 | 2 | 98 |
| 4.9 | 100 | 0 |
| 5.0 | 100 | 0 |

2b) UPLC-HRMS—Analytic Method D

Waters Acquity UPLC® BEH C18, 1.7 μm, 2.1×50 mm; Part no: 186002350

Eluent A: 0.05% FA+3.75 mM ammonium acetate in water; Eluent B: 0.04% FA in ACN

Flow: 1.0 ml/min

Temperature: 50° C.

Gradient: 2 to 98% in 4.4 min

3) Analytical Method E:

XBridge C18 Column, 3.5 μm, 3.0×30 mm

Eluent: A: Water (0.1% formic acid); B: CAN

Flow rate: 2 mL/min

Gradient: 0 min 40% B; 40% to 95% B in 1.70 min; 2.0 min 95% B; 2.1 min 40% B

Mass Spectrometer: Single Quadrupole ESI scan range 150-1600

HPLC: Agilent 1100 series

Temperature: 40 C

3) Analytical Method F:

Acquity BEH 1.7 μm 2.1×50 mm

Eluent: A: Water (0.1% formic acid); B: ACN (0.1% formic acid)

Flow rate: 1 mL/min

Gradient: 0 min 2% B; 2% to 98% B in 1.7 min; 2.06 min 98% B; 2.16 min 2% B

Mass Spectrometer: Single Quadrupole ESI scan range 120-1600

HPLC: waters Acquity

Temperature: 50 C

3) Analytical Method G:

Acquity BEH 1.7 μm 2.1×50 mm

Eluent: A: Water (0.1% formic acid); B: ACN (0.1% formic acid)

Flow rate: 1 mL/min

Gradient: 0 min 40% B; 40% to 98% B in 1.40 min; 2.05 min 98% B; 2.1 min 40% B

Mass Spectrometer: Single Quadrupole ESI scan range 120-1600

HPLC: waters Acquity

Temperature: 50 C

The analytical data for peptides of Examples 1 to 38 are summarized in Table 5 and was generated using the analytical methods described supra.

TABLE 5

| Peptide | HPLC $t_R$ [min] | Meth. | Mass spectrometry $[M+2H]^{2+}$ (measured) | $[M+3H]^{3+}$ (measured) | Meth. | $[M+2H]^{2+}$ (calc.) | $[M+3H]^{3+}$ (calc.) |
|---|---|---|---|---|---|---|---|
| Example 1 | 3.48 | A | 757.4 | 505.3 | C | 757.4 | 505.3 |
| Example 2 | 3.66 | A | 735.4 | 490.6 | C | 735.4 | 490.6 |
| Example 3 | 3.60 | A | 764.4 | 509.9 | C | 764.4 | 509.9 |
| Example 4 | 2.65 | A | 683.4 | 455.9 | C | 683.4 | 455.9 |
| Example 5 | 3.95 | A | 782.4 | 521.9 | C | 782.4 | 521.9 |
| Example 6 | 3.49 | A | 764.4 | 509.9 | C | 764.4 | 509.9 |
| Example 7 | 3.55 | A | 771.4 | 514.6 | C | 771.4 | 514.6 |
| Example 8 | 2.85 | A | 719.3 | 479.9 | C | 719.4 | 479.9 |
| Example 9 | 3.75 | A | 742.4 | 495.3 | C | 742.4 | 495.3 |
| Example 10 | 3.55 | A | 757.4 | 505.3 | C | 757.4 | 505.3 |
| Example 11 | 3.57 | A | 686.9 | 458.3 | C | 686.9 | 458.2 |
| Example 12 | 3.51 | A | 757.4 | 505.3 | C | 757.4 | 505.3 |
| Example 13 | 3.54 | A | 764.4 | 509.9 | C | 764.4 | 509.9 |
| Example 14 | 3.46 | A | 757.4 | 505.3 | C | 757.4 | 505.3 |
| Example 15 | 3.44 | A | 757.4 | 505.3 | C | 757.4 | 505.3 |
| Example 16 | 3.59 | A | 771.4 | 514.6 | C | 771.4 | 514.6 |
| Example 17 | 3.61 | A | 771.4 | 514.6 | C | 771.4 | 514.6 |
| Example 18 | 7.60 | B | 775.391 | 517.263 | D | 775.385 | 517.256 |
| Example 19 | 7.40 | B | 751.392 | 501.263 | D | 751.385 | 501.256 |
| Example 20 | 3.41 | A | 743.4 | 495.9 | C | 743.4 | 495.9 |
| Example 21 | 7.35 | B | 730.355 | 487.239 | D | 730.361 | 487.241 |
| Example 22 | 8.62 | B | 739.877 | 493.587 | D | 739.856 | 493.573 |
| Example 23 | 7.32 | B | 737.374 | 491.918 | D | 737.377 | 491.921 |
| Example 24 | 7.35 | B | 737.375 | 491.919 | D | 737.377 | 491.921 |
| Example 25 | 5.63 | B | 620.822 | 414.217 | D | 620.825 | 414.219 |
| Example 26 | 7.58 | B | 754.368 | 503.247 | D | 754.361 | 503.241 |
| Example 27 | 7.36 | B | 737.374 | 491.918 | D | 737.369 | 491.913 |
| Example 28 | 3.63 | A | 713.9 | 476.2 | C | 713.8 | 476.2 |
| Example 29 | 3.78 | A | 720.9 | 480.9 | C | 720.9 | 480.9 |
| Example 30 | 3.82 | A | 691.9 | 461.6 | C | 691.8 | 461.6 |
| Example 31 | 3.74 | A | 643.3 | 429.2 | C | 643.3 | 429.2 |
| Example 32 | 8.01 | B | 643.328 | 429.222 | D | 643.324 | 429.252 |
| Example 33 | 7.73 | B | 700.832 | 467.557 | D | 700.845 | 467.566 |
| Example 34 | 7.17 | B | 609.809 | 406.875 | D | 609.810 | 406.876 |
| Example 35 | 8.99 | B | 710.351 |  | D | 710.332 | 473.890 |
| Example 35 | 6.89 | B | 568.289 | 379.196 | D | 568.292 | 379.197 |
| Example 36 | 7.69 | B | 724.843 | 483.564 | D | 724.837 | 483.558 |

TABLE 5-continued

| | HPLC | | | | Mass spectrometry | | |
| --- | --- | --- | --- | --- | --- | --- | --- |
| Peptide | $t_R$ [min] | Meth. | $[M + 2H]^{2+}$ (measured) | $[M + 3H]^{3+}$ (measured) | Meth. | $[M + 2H]^{2+}$ (calc.) | $[M + 3H]^{3+}$ (calc.) |
| Example 37 | 6.62 | B | 715.848 | 477.568 | D | 715.843 | 477.562 |
| Example 38 | 8.28 | B | 728.873 | | D | 728.869 | |

General Synthesis Procedures

1) Loading of First Amino Acid onto 2-Chlorotrityl Chloride Resin and Fmoc-Removal 2-Chlorotrityl chloride resin (1 eq., 1.0-1.6 mmol/g) was washed thoroughly with DCM. The desired amino acid (typically 0.5-2 eq. relative to the resin, considering 1.6 mmol/g loading) was dissolved in DCM (approx. 10 mL per gram of resin) and DIPEA (4 eq. relative to the resin, considering 1.6 mmol/g loading). The solution was added to the resin and the suspension was shaken at rt for 3-16 h. The resin was drained and then thoroughly washed sequentially with DCM/MeOH/DIPEA (17:2:1), DCM, DMA, DCM.

For Fmoc removal and determination of the loading the resin was shaken repeatedly with piperidine/DMA (1:4) or 4-methylpiperidine/DMA (1:4) (12×10 mL per gram of initial resin) and washed with DMA (2×10 mL per gram of initial resin). The combined solutions were diluted with MeOH to a volume V of 250 mL per gram of initial resin. A 2 mL aliquot ($V_a$) of this solution was diluted further to 250 mL ($V_t$) with MeOH. The UV absorption was measured at 299.8 nm against a reference of MeOH, giving absorption A. The resin was thoroughly washed sequentially with DMA, DCM, DMA, DCM and dried in high vacuum at 40° C., affording m g of resin.

The loading of the resin is calculated according to the formula:

Loading $[mol/g] = (A \times V_t \times V)/(d \times \epsilon \times V_a \times m)$ (with d: width of cuvette; $\epsilon = 7800$ L mol$^{-1}$ cm$^{-1}$)

2) Solid Phase Peptide Synthesis

2a) Synthesis Cycle A on Prelude™ Synthesizer

The resin was washed with DMA. Fmoc was removed by repetitive treatment with piperidine/DMA (1:4) or 4-methylpiperidine/DMA (1:4). The resin was washed with DMA. Coupling was done by addition of the Fmoc-amino acid (3 eq.; 0.3 M solution in NMP), HCTU (3 eq.; 0.3 M solution in NMP), and DIPEA (4.5 eq.; 0.9 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2a) Synthesis Cycle B on Prelude™ Synthesizer

The resin was washed with DMA. Fmoc was removed by repetitive treatment with 4-methylpiperidine/DMA (1:4). The resin was washed with DMA. Coupling was done by addition of the Fmoc-amino acid (3 eq.; 0.2 M solution in NMP), HCTU (3 eq.; 0.3 M solution in NMP), and DIPEA (3.3 eq.; 0.66 M solution in NMP) followed by mixing of the suspension with nitrogen at rt for typically 15 min to 4 h depending on the specific requirements. After washing with DMA the coupling step was typically repeated 1 to 3 times depending on the specific requirements. After washing with DMA capping was performed by addition of a mixture of Ac$_2$O/pyridine/DMA (1:1:8) and subsequent mixing of the suspension at rt. The resin was washed with DMA.

2b) Synthesis Cycle C on Prelude™ Synthesizer

The resin was washed with DMA. Fmoc was removed by repetitive treatment with piperidine/DMA (1:4) or 4-methylpiperidine/DMA (1:4). The resin was washed with DMA. Capping was performed by addition of a mixture of Ac$_2$O/pyridine/DMA (1:1:8) and subsequent mixing of the suspension at rt. The resin was washed with DMA.

2c) Synthesis Cycle D on Liberty™ Synthesizer

The resin was washed with DMF and DCM. Fmoc was removed by treatment with 20% piperidine/DMF (typically 7 ml per 0.1 mmol twice). The resin was washed with DMF and DCM. Coupling was done by addition of the Fmoc-amino acid (5 eq.; 0.2 M solution in DMF), HCTU (5 eq.; 0.5 M solution in DMF), and DIPEA (10 eq.; 2 M solution in NMP) followed by mixing of the suspension with nitrogen at 75 or 50° C. for typically 5 to 50 min with microwave power 0 to 20 watts depending on the specific requirements. After washing with DMF the coupling step might be repeated once depending on the specific requirements. The resin was washed with DMF.

3) Cleavage from Resin with or without Concomitant Removal of Protecting Groups

3a) Cleavage Method a

The resin (0.1 mmol) was shaken at rt for 2 h with 95% aq. TFA/EDT/TIS (95:2.5:2.5) (3 mL). The cleavage solution was filtered off, and fresh solution was added (3 mL). The suspension was shaken at rt for 1 h then the cleavage solution was filtered off. Fresh solution was added (3 mL) and the suspension was shaken at rt for 1 h. The cleavage solution was filtered off. The combined cleavage solutions were poured slowly onto a mixture of cold heptane/diethyl ether (1:1) (35 mL), giving a precipitate. The suspension was centrifuged and the supernatant poured off. The residue was washed with cold heptane/diethyl ether (1:1) (10-20 mL), the suspension was centrifuged and the supernatant was poured off. This step was performed 1-2-times. The solid was dried in high vacuum.

3b) Cleavage Method B

The resin (0.1 mmol) was shaken at rt for 3 h with 95% aq. TFA//TIS/DTT (95:2.5:2.5) (3 mL). The cleavage solution was filtered off. The resin was rinsed once with 95% aq. TFA (1 mL). The combined cleavage and washing solutions were poured slowly onto a mixture of cold heptane/diethyl ether (1:1) (10-15 mL), giving a precipitate. The suspension was centrifuged and the supernatant poured off. Diethyl ether (10 mL) was added to the residue, the suspension was vortexed for 3 min and centrifuged, and the supernatant was poured off, The wash process was repeated twice. The solid was dried in high vacuum.

3c) Cleavage Method C

HFIP/DCM (1:3) (3 mL) was added to the resin (0.1 mmol) and the suspension was shaken at rt for 20 min. The cleavage solution was filtered off and collected. This procedure was repeated twice. Finally the resin was washed once with HFIP/DCM (1:3) (1 mL). The combined cleavage and washing solutions were concentrated to dryness in vacuo. The crude product was lyophilized from ACN/H$_2$O.

4) Disulfide Formation

4a) Cyclization Method A

The fully deprotected linear precursor peptide was dissolved in H$_2$O/DMSO (9:1) or (4:1) to give typically a concentration of 0.5-7 mM. The reaction mixture was then stirred at rt for typically 16-96 h depending on the requirements and then concentrated to dryness in high vacuum.

4b) Cyclization Method B

The fully deprotected linear precursor peptide (1 eq.) was dissolved in H$_2$O to give typically a concentration of about 1-25 mM. A solution of 50 mM I$_2$ in AcOH (1-2 eq.) was added and the mixture was stirred at rt until complete conversion is achieved. 0.5 M Ascorbic acid in H$_2$O was added to quench the excess of I$_2$.

In the following the syntheses of representative examples are described.

Example 9

Synthesis of Ac-C*-R-P-R-L-S-C*-K-G-P-Nle-P-NMe(Phenethyl) (Disulfide C$^1$-C$^7$) (SEQ ID NO: 27)

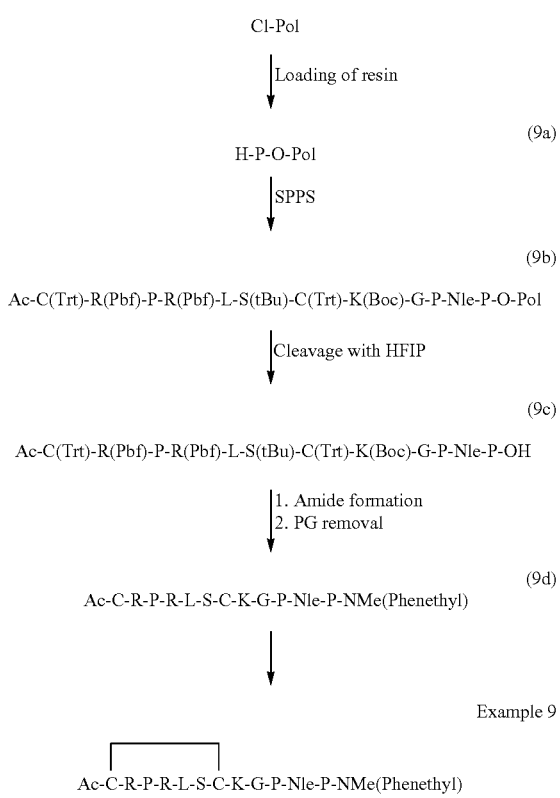

(SEQ ID NOS 58, 58, 27, and 27, respectively, in order of appearance)

Preparation of Intermediate 9a (Loading of 2-Chlorotrityl Chloride Resin with Fmoc-P—OH, Fmoc Removal and Determination of the Loading of the Resin)

2-Chlorotrityl chloride resin (2.00 g, 3.20 mmol) was washed with DCM (3×). A solution of Fmoc-P—OH (1.08 g, 3.20 mmol) in DCM (20 mL) and DIPEA (2.24 mL, 12.8 mmol) was added and the suspension was shaken for 3 h at rt. The resin was washed thoroughly with DCM/MeOH/DIPEA (17:2:1) (3×), DCM (3×), DMA (3×), DCM (3×).

The resin was then treated twelve times for 2 min with a mixture of piperidine/DMA (1:4) (12 mL each time). The piperidine/DMA solutions were collected for determination of the loading of the resin (see general procedure).

The resin was washed thoroughly with DCM (3×), DMA (3×), DCM (3×) and dried in vacuo to give Intermediate 9a (2.25 g; loading=1.12 mmol/g).

Preparation of Intermediate 9b (Assembly of Linear Peptide)

Intermediate 9a (89 mg, 0.10 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | Nle | 2 × 1 h | B |
| 2 | P | 2 × 30 min | B |
| 3 | G | 2 × 1 h | B |
| 4 | K(Boc) | 2 × 30 min | B |
| 5 | C(Trt) | 2 × 30 min | B |
| 6 | S(tBu) | 2 × 30 min | B |
| 7 | L | 2 × 30 min | B |
| 8 | R(Pbf) | 4 × 1 h | B |
| 9 | P | 2 × 1 h | B |
| 10 | R(Pbf) | 4 × 1 h | B |
| 11 | C(Trt) | 2 × 1 h | B |
| 12 | Ac | 1 × 10 min | C |

Preparation of Intermediate 9c (HFIP Cleavage from the Resin)

HFIP/DCM (1:3) (3 mL) was added to Intermediate 9b (0.100 mmol) and the suspension was shaken at rt for 20 min. The cleavage solution was filtered off and collected. This procedure was repeated twice. Finally the resin was washed once with HFIP/DCM (1:3) (1 mL). The combined cleavage and washing solutions were concentrated to dryness in vacuo. The crude product was lyophilized from ACN/H$_2$O to afford Intermediate 9c (37.2 mg, 14.8 μmol) as a white solid.

Preparation of Intermediate 9d (Amide Formation and Protecting Group Removal)

Intermediate 9c (37.0 mg, =14.7 μmol) and TBTU (7.1 mg, 22.1 μmol) were dissolved in DCM (5 mL). DIPEA (5.1 μl, 29.4 μmol) was added and the solution was stirred for 2 min at rt. N-Methyl-phenethylamine (3.2 μl, 22.1 μmol) was added, the reaction was stirred for 1 h 40 min at rt then partitioned between EtOAc/n-butanol (9:1) (50 mL) and 5% aq. NaHCO$_3$ (5 mL). The organic layer was washed with 5% aq. NaHCO$_3$ (5 mL), brine (5 mL), dried over Na$_2$SO$_4$, filtered and concentrated to dryness in vacuo.

The residue was dissolved in 95% aq. TFA/TIS/EDT (95:2.5:2.5) (5 mL). The reaction mixture was stirred for 3 h at rt then poured on cold heptane/ether (1:1) (35 mL). The suspension was centrifuged and the solvent was decanted. The residue was washed twice with cold diethylether/heptane (1:1) (10 mL) and then dried in vacuo to afford Intermediate 9d (27.0 mg, 14.7 µmol) as a beige solid. The product was subjected to the next step without purification.

Preparation of Example 9

Disulfide Formation and Purification

Intermediate 9d (26.9 mg, 14.7 µmol) was dissolved in $H_2O$ (3.7 mL) (solution was slightly cloudy). A solution of 50 mM $I_2$ in AcOH (0.353 mL, 17.6 µmol) was added and the mixture was stirred at rt for 30 min. 0.5 M Ascorbic acid in $H_2O$ (0.044 mL, 22.1 µmol) was added to quench the excess of iodine. The solution was concentrated to about 3.5 mL and then subjected to preparative reversed-phase HPLC. Fractions were lyophilized to afford Example 9 (6.8 mg, 3.7 µmol) as a white solid.

The pure product was analyzed by analytical HPLC (Analytical method A; $t_R$=3.75 min) and UPLC-MS (Analytical method C; measured: $[M+3]^{3+}$=495.3; calculated: $[M+3]^{3+}$=495.3).

Example 12

Synthesis of Ac-c*-R-P-R-L-S-C*-K-G-P-Nle-P-F-OH (Disulfide $C^1$-$C^7$) (SEQ ID NO: 30)

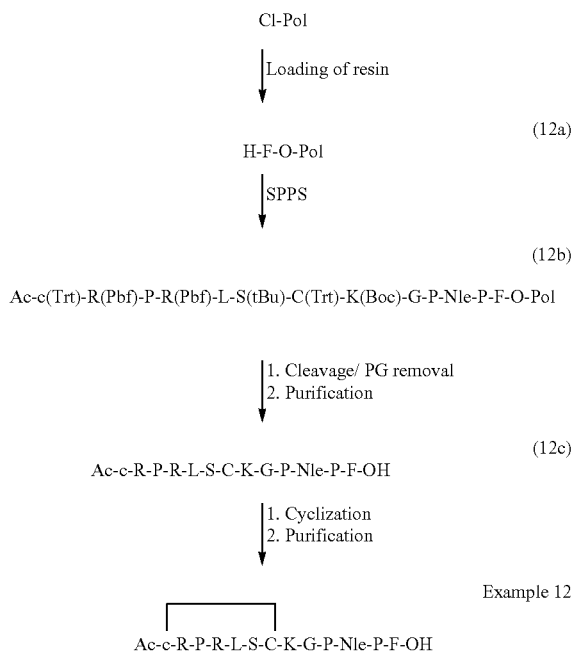

(SEQ ID NOS 59, 30, and 30, respectively, in order of appearance)

Preparation of Intermediate 12a (Loading of 2-Chlorotrityl Chloride Resin with Fmoc-F-OH, Fmoc Removal and Determination of the Loading of the Resin)

2-Chlorotrityl chloride resin (10.0 g, 16.0 mmol) was washed with DCM (3×). A solution of Fmoc-F-OH (12.4 g, 32.0 mmol) in DCM (100 mL) and DIPEA (11.2 mL, 64.0 mmol) was added and the suspension was shaken for 5 h at rt. The resin was washed thoroughly with DCM/MeOH/DIPEA (17:2:1) (3×), DCM (3×), DMA (3×), DCM (3×).

The resin was then treated twelve times for 2 min with a mixture of piperidine/DMA (1:4) (50 mL each time) followed by washing with DMA (2×). The piperidine/DMA solutions and DMA washing solutions were collected for determination of the loading of the resin (see general procedure).

The resin was washed thoroughly with DCM (3×), DMA (3×), DCM (3×) and dried in vacuo to give Intermediate 12a (12.8 g; loading=0.79 mmol/g).

Preparation of Intermediate 12b (Assembly of Linear Peptide)
Intermediate 12a (127 mg, 0.10 mmol) was subjected to solid phase peptide synthesis on the Prelude™ peptide synthesizer. Coupling was performed as follows:

| Coupling | AA | Number of couplings × Reaction time | Synthesis cycle |
|---|---|---|---|
| 1 | P | 2 × 1 h | A |
| 2 | Nle | 2 × 1 h | A |
| 3 | P | 2 × 1 h | A |
| 4 | G | 2 × 2 h | A |
| 5 | K(Boc) | 2 × 1 h | A |
| 6 | C(Trt) | 1 × 3 h | A |
| 7 | S(tBu) | 2 × 1 h | A |
| 8 | L | 2 × 1 h | A |
| 9 | R(Pbf) | 4 × 3 h | A |
| 10 | P | 2 × 2 h | A |
| 11 | R(Pbf) | 4 × 3 h | A |
| 12 | c(Trt) | 1 × 3 h | A |
| 13 | Ac | 1 × 20 min | C |

Preparation of Intermediate 12c (Cleavage from the Resin with Concomitant Protecting Group Removal and Purification)

Intermediate 12b (0.10 mmol) was carefully washed with DCM (4×). A mixture of 95% aq. TFA/EDT/TIS (95:2.5:2.5) (2 mL) was added and the suspension was shaken at rt for 2 h. The cleavage solution was filtered off, and fresh cleavage solution (2 mL) was added. The suspension was shaken at rt for 1 h then the cleavage solution was filtered off. Fresh solution (2 mL) was added and the suspension was shaken at rt for 1 h. The cleavage solution was filtered off. The combined cleavage solutions were poured onto a mixture of cold heptane/diethyl ether (1:1) (30 mL), giving a precipitate. The mixture was centrifuged and the supernatant poured off. The solid was washed again with cold heptane/diethyl ether (1:1) (10 mL), the mixture was centrifuged and the supernatant poured off. The solid was dried in vacuo. The crude product was purified by preparative HPLC and lyophilized to afford Intermediate 12c (53 mg, 0.029 mmol).

Preparation of Example 12

Cyclization and Purification

Intermediate 12c (53 mg, 0.029 mmol) was dissolved in $H_2O$/DMSO (9:1) (18 mL). The reaction mixture was stirred at rt for 40 h then concentrated to dryness in vacuo. The crude product was purified by preparative HPLC and lyophilized to afford Example 12 as a white solid (27.4 mg; 0.014 mmol).

The pure product was analyzed by analytical HPLC (Analytical method A; $t_R$=3.51 min) and UPLC-MS (Analytical method C; measured: $[M+3]^{3+}$=505.3; calculated: $[M+3]^{3+}$=505.3).

Example 18

Synthesis of Ac-(D-hC)*-R-P-R-L-S-(hC)*-K-G-P-f-a-f-OH (Disulfide $C^1$-$C^7$) (SEQ ID NO: 36)

Fmoc-D-Phe-Wang resin (substitution: 0.66 mmol/g) was subjected to manual solid phase peptide synthesis via standard Fmoc chemistry. 0.3 mmol resin was swelled in DMF for 30 minutes; DMF was drained and the resin was treated with 20% piperidine in DMF for 30 min to remove Fmoc group. The resin was washed by DMF 3 times and coupled with a pre-activated Fmoc amino acid solution (Fmoc amino acid/HBTU/HOBt/NMM=3:3:3:6 eq) for 2 hours. Ninhydrin test was performed after each coupling to check the coupling efficiency.

The peptide chain was assembled on resin by repetitive removal of the Fmoc protecting group and coupling of protected amino acid till N-term end.

After the coupling of the last amino acid, peptide resin was washed with DMF and ethyl ether, and dried under vacuum. The dried peptide resin was treated with TFA cleavage cocktail (TFA/thioanisole/phenol/EDT/$H_2O$=87.5:5:2.5:2.5:2.5, v/v) for cleavage and removal of the side chain protecting groups. Crude peptides were precipitated from cold ether, collected by filtration and dried under high vacuum. Crude peptides was purified on HPLC (Column: 2"-inch Delta Pak C18, Wavelength: 215 nm) to afford desired product.

Cyclisation:

Each of crude peptides was dissolved in water-Acetonitrile (A.C.S. reagent, Fisher) at a concentration of 1 mg/mL (around 80%:20%; Water: Acetonitrile, V:V), 0.1 M $I_2$ (A.C.S. reagent, Sigma Aldrich) in 50% AcOH (A.C.S. reagent, Fisher)/$H_2O$ was added drop-wise into the solution with vigorous stirring until $I_2$ color persist. Upon completion of oxidation (monitored by analytical HPLC and Mass spectroscopy), 1M L-ascorbic acid (A.C.S. reagent, Sigma Aldrich) aqueous solution was drop-wise added with continuous stirring to reduce excess $I_2$ until the solution becomes colorless. After filtration, the above solution was loaded onto 2-inch C18 column (detection at 215 nm), and purified by using TFA buffer (Buffer A, 0.1% TFA (A.C.S. grade, NuGeneration Technology, LLC) in water; Buffer B, 100% acetonitrile), collected fractions with purity of >95% were lyophilized to dry.

Example 21

Synthesis of pE-R-C*-R-L-S-C*-K-G-P-(D-Nle)-a-f-OH (Disulfide $C^3$-$C^7$) (SEQ ID NO: 39)

Cl-Pol

↓ Loading of resin

-continued

H-f-O-Pol (21a)

↓ SPPS pE-R(Pbf)-C(Trt)-R(Pbf)-L-S(tBu)-C(Trt)-K(Boc)-G-P-(D-Nle)-a-f-O-Pol (21b)

↓ 1. Cleavage/ PG removal
2. Purification pE-R-C-R-L-S-C-K-G-P-(D-Nle)-a-f-OH (21c)

↓ 1. Cyclization
2. Purification

Example 21 pE-R-C-R-L-S-C-K-G-P-(D-Nle)-a-f-OH (SEQ ID NOS 60, 39, and 39, respectively, in order of appearance)

Preparation of Intermediate 21a (Loading of 2-Chlorotrityl Chloride Resin with Fmoc-f-OH, Fmoc Removal and Determination of the Loading of the Resin)

2-Chlorotrityl chloride resin (5.0 g, 8.01 mmol) was reacted with a solution of Fmoc-f-OH (3.10 g, 8.01 mmol) in DCM (50 mL) and DIPEA (5.59 mL, 32.0 mmol) in analogy to the general procedure described above to give Intermediate 21a (5.87 g, loading=0.897 mmol/g).

Preparation of Intermediate 21b (Assembly of Linear Peptide)

Intermediate 21a (0.100 mmol) was subjected to solid phase peptide synthesis on the Liberty™ microwave peptide synthesizer. Coupling was performed as follows:

| Coupling | AA | Number of couplings × Reaction time | Temperature ° C. | Microwave power | Synthesis cycle |
|---|---|---|---|---|---|
| 1 | a | 1 × 7.5 min | 50 | 20 | D |
| 2 | D-Nle | 1 × 7.5 min | 50 | 20 | D |
| 3 | P | 1 × 7.5 min | 50 | 20 | D |
| 4 | G | 1 × 7.5 min | 50 | 20 | D |
| 5 | K(Boc) | 1 × 7.5 min | 50 | 20 | D |
| 6 | C(Trt) | 1 × 2 min | 50 | 0 | D |
|   |   | 1 × 4 min | 50 | 25 |   |
| 7 | S | 1 × 7.5 min | 50 | 25 | D |
| 8 | L | 1 × 7.5 min | 50 | 25 | D |
| 9 | R(Pbf) | 2 × 42 min | 50 | 0 | D |
|   |   | 2 × 7.5 min | 50 | 25 |   |
| 10 | C(Trt) | 1 × 2 min | 50 | 0 | D |
|   |   | 1 × 4 min | 50 | 25 |   |
| 11 | R(Pbf) | 2 × 42 min | 50 | 0 | D |
|   |   | 2 × 7.5 min | 50 | 25 |   |
| 12 | pE | 1 × 7.5 min | 50 | 25 | D |

Preparation of Intermediate 21c (Cleavage from the Resin with Concomitant Protecting Group Removal then Purification)

A mixture of 95% aq. TFA/EDT/DTT (95:2.5:2.5) (2 mL) was added to Intermediate 21b (0.1 mmol). The suspension was shaken at rt for 2 h, then the cleavage solution was filtered off. The resin was then again treated with 95% aq. TFA/EDT/TIS (95:2.5:2.5) (2 mL), shaken at rt for 1 h, and filtered. The combined cleavage and washing solutions were poured onto a mixture of cold heptane/diethyl ether (1:1) (11 mL), giving a precipitate. The suspension was centrifuged and the supernatant poured off. Diethyl ether (10 mL) was added to the residue, the suspension was vortexed for 3 min and centrifuged, and the supernatant was poured off. The washing process was repeated twice. The solid was dried in high vacuum The crude was purified by preparative HPLC and lyophilized from ACN/H$_2$O to afford Intermediate 21c (55 mg, 0.030 mmol).

Preparation of Example 21

Cyclization and Purification

Intermediate 21c (18 mg, 9.97 µmol) was dissolved in H$_2$O (1.0 mL). A solution of 50 mM I$_2$ in AcOH (0.24 mL, 12 µmol) was added in one portion to the stirred solution and the solution was stirred overnight at rt until LCMS showed completion of the reaction. 0.5 M Ascorbic acid in H$_2$O (24 µmol, 12 µmol) was added to quench the excess of I$_2$. The crude was purified by preparative HPLC and lyophilized from ACN/H$_2$O to afford Example 21 as a white solid (12 mg, 6.32 µmol).

The pure product was analyzed by analytical HPLC (Analytical method B; $t_R$=7.35 min) and UPLC-HRMS (Analytical method D; measured: [M+2H]$^{2+}$=730.355; calculated: [M+2H]$^{2+}$=730.361).

Example 32

Synthesis of pE-R-P-C*-L-S-C*-K-G-P-(D-Nle)-NH(Phenethyl) (Disulfide C$^4$-C$^7$) Acetate (SEQ ID NO: 50)

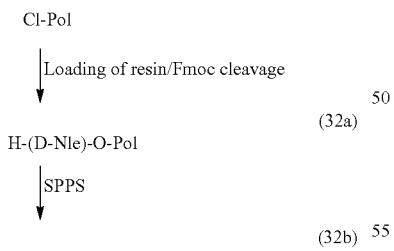

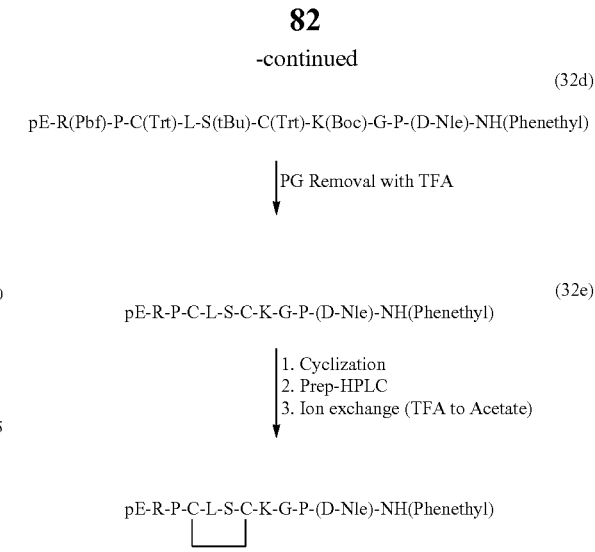

Example 32
(SEQ ID NOS 61, 61, 61, 50, and 50, respectively, in order of appearance)

Preparation of Intermediate 32a (Loading of 2-Chlorotrityl Chloride Resin with Fmoc-D-Nle-OH, Fmoc Removal and Determination of the Loading of the Resin)

2-Chlorotrityl chloride resin (50.0 g, 85.0 mmol) was suspended in of DCM (400 mL) the suspension was stirred for 10 min and then the solvent was drained, the resin was washed with DCM (3×200 mL). Then a solution of Fmoc-D-Nle-OH (24.0 g, 68.0 mmol) and DIPEA (96.5 ml, 552.5 mmol) in DCM (120.0 mL) was added to the resin, the suspension was flushed with nitrogen and stirred at rt for 5 min. Another portion of DIPEA (22.7 ml, 127.5 mmol) was added and the reaction mixture was stirred at rt overnight.

The reaction mixture was drained and the resin was washed with DCM (3×250 mL) for 2 min each time. The resin was quenched with of a mixture DCM/MeOH/DIPEA (70:15:15) (2×250 mL) for 10 min each time.

The Fmoc group was cleaved by treating the resin with piperidine/DMF (1:3) (1×300 mL) for 5 min. the resin was drained then (1×300 mL) for 15 min, followed by washing steps: DMF (6×250 mL, 2 min each time), isopropanol (2×250 mL, 2 min each time) and TBME (6×250 mL, 2 min each time). The resin was dried under vacuum at 35° C. for 24 hours to afford Intermediate 32a (57.8 g, loading=1.08 mmol/g).

Preparation of Intermediate 32b (Assembly of Linear Peptide)

Intermediate 32a (18.5 g, 20.0 mmol) was subjected to solid phase peptide synthesis on an automatic peptide synthesizer (CSBIO536™). A coupling cycle was defined as follows:

Amino acid coupling: AA (3.0 eq.), DIC (3.0 eq.), HOBt (3.0 eq.), DMF (see table below)

Washing: DMF (4×150 mL, 2 min each time).

Fmoc deprotection: Piperidine/DMF (1:3) (150 mL for 5 min then 150 mL for 15 min).

Washing: DMF (6×150 mL, 2 min each time).

| Coupling | AA | Number of couplings × Reaction time | Coupling Method |
|---|---|---|---|
| 1 | Fmoc-L-Pro-OH | 1 × 120 min | DIC/HOBt |
| 2 | Fmoc-Gly-OH | 1 × 120 min | DIC/HOBt |
| 3 | Fmoc-L-Lys(Boc)-OH | 1 × 120 min | DIC/HOBt |
| 4 | Fmoc-L-Cys(Trt)-OH | 1 × 120 min | DIC/HOBt |
| 5 | Fmoc-L-Ser(tBu)-OH | 1 × 120 min | DIC/HOBt |
| 6 | Fmoc-L-Leu-OH | 1 × 120 min | DIC/HOBt |
| 7 | Fmoc-L-Cys(Trt)-OH | 1 × 120 min | DIC/HOBt |
| 8 | Fmoc-L-Pro-OH | 1 × 120 min | DIC/HOBt |
| 9 | Fmoc-L-Arg(Pbf)-OH | 1 × 120 min | DIC/HOBt |
| 10 | Boc-L-Pyr—OH | 1 × 120 min | DIC/HOBt |

After the assembly of the peptide, the resin was washed with DMF (6×150 mL, 2 min each time), isopropanol (6×150 mL, 2 min each time) and TBME (6×150 mL, 2 min each time). The peptide resin was dried overnight under high vacuum at 35° C. to give Intermediate 32b (57.6 g, 20.0 mmol).

Preparation of Intermediate 32c (HFIP Cleavage from the Resin)

A portion of Intermediate 32b (27 g, 9.37 mmol) was suspended in DCM (300 mL) and stirred for 15 min. The resin was drained then treated with HFIP/DCM (3:7) (3×270 mL, 15 min each time). The cleavage solution was filtered off and collected. The resin was washed with DCM (3×300 mL). The combined cleavage and washing solutions were concentrated to dryness in vacuo. The white powder was dried overnight under vacuum at 35° C. yielding Intermediate 32c-Batch1 (23.5 g, 9.37 mmol).

The above mentioned procedure was repeated with another portion of Intermediate 32b (28.0 g, 9.72 mmol), affording Intermediate 32c-Batch2 (26.1 g, 9.72 mmol).

Preparation of Intermediate 32d (Solution Phase Coupling of Phenethylamine)

Intermediate 32c-Batch2 (20.0 g, 7.44 mmol, 1.0 eq) and HATU (5.23 g, 13.8 mmol, 1.85 eq) were dissolved in DMF (400 mL). A solution of phenethylamine (1.67 g, 13.8 mmol, 1.85 eq) and DIPEA (3.56 g, 27.6 mmol, 3.71 eq) in DMF (60 mL) was added.

The reaction mixture was stirred at rt for 30 min then cooled down to 0° C. then brine (460 mL) was added. The suspension was stirred for 10 min then the product was isolated by filtration. The filter cake was washed with $H_2O$ (300 mL), which was then carefully removed, then dissolved in DCM (300 mL). The solution was dried over MgSO4 then concentrated to dryness in vacuo. The crude product was subjected to flash chromatography over silica gel (eluents: DCM and DCM/iPrOH (8:2)) to afford Intermediate 32d-Batch1 (14.4 g, 6.6 mmol).

The same procedure was repeated with Intermediate 32c-Batch1 (23.4 g, 9.37 mmol), excluding the flash chromatography, affording Intermediate 32d-Batch2 (28.0 g, 9.37 mmol).

Preparation of Intermediate 32e (Protecting Group Removal)

Intermediate 32d-Batch2 (28.0 g, 9.37 mmol) was dissolved in TFA/DCM/EDT/TIS (90:5:2.5:2.5) (290 mL) and the reaction stirred at rt for 2 h.

The cleavage solution was filtered off and poured onto cold TBME (3 L) (0-4° C.). The turbid suspension was stirred in an ice-water bath for 30 min then filtered through a pore 4 glass filter. The white solid thus obtained was washed with TBME (2×100 mL) then dried in vacuum at 35° C. overnight to afford Intermediate 32e-Batch1 (8.9 g, 5.9 mmol).

The same procedure was repeated with Intermediate 32d-Batch1 (14.4 g, 6.6 mmol) yielding Intermediate 32e-Batch2 (9.6 g, 6.3 mmol).

Preparation of Example 32

1) Cyclization

Intermediate 32e (5.0 g, 3.3 mmol) was dissolved in water (500 mL). A solution of iodine (1.18 g, 4.66 mmol, 1.41 eq) in acetic acid (93 mL) was added in one portion. The reaction mixture was stirred at rt for 10 min. A solution of ascorbic acid (1.03 g, 5.83 mmol, 1.77 eq) in water (5.8 mL) was added and the reaction mixture stirred for 10 min, filtered and stored at 4° C. until purification.

The same cyclization procedure was repeated until 18.3 g (12.1 mmol) of Intermediate 32e had been processed.

2) Purification

The solutions of cyclic peptide were subjected to preparative HPLC in portions of 0.5-5.0 g peptide per injection. The fractions having purity higher than 95% were pooled and freeze dried to yield a total amount of 4.89 g (3.2 mmol) of purified peptide (TFA salt) was produced.

3) Acetate Formation by Ion Exchange 75 g (100 mL) of a strong anion exchanger resin (Ion exchanger III, Merck) in its $OH^-$ form was placed in sintered glass filter (porosity 3) and then a solution of acetic acid/water (1:3) (300 mL) was added, the suspension was manually stirred for 2 min then the resin was drained. The process was repeated with another portion of acetic acid/water (1:3) (300 mL). The resin was washed with deionized water until a neutral drain was observed. Then the resin was transferred to a 4×20 cm column equipped with a sintered glass filter (porosity 3).

4.8 g of purified peptide was dissolved in deionized water (50 mL) and added to the column. The product was eluted with deionized water (200 mL). Control of product elution was done by TLC spotting, the rich fractions were pooled and freeze dried to give Example 32 (4.1 g, 2.9 mmol).

The pure product was analyzed by analytical HPLC (Analytical method B; $t_R$=8.01 min) and UPLC-HRMS (Analytical method D; measured: $[M+2H]^{2+}$=643.328; calculated: $[M+2H]^{2+}$=643.324). The acetate content was 7.99-8.27% and the water content was 1.94-1.96%.

The other examples were synthesized in analogy:
Examples 1 to 8, 10, 11, 13 to 17, 20, 28 to 31 were synthesized in analogy to Example 12.
Examples 19, 26, 27, 36-38 were synthesized in analogy to Example 18.
Examples 22-25, 33-35 were synthesized in analogy to Example 21.

Bioconjugate Examples

Example 39

Albumin-PPA-O2Oc-O2Oc-O2Oc-O2Oc-Q-R-P-C*-L-S-C*-K-G-P-(D-Nle)Phenethylamine (SEQ ID NO: 62) Wherein PPA is 3-(pyridin-2-yldisulfanyl)propanoic acid Step 1: Albumin Decapping Decapping with TCEP To a solution of albumin (500 mg, Aldrich, lyophilized powder, from human serum) in 10 mL of PBS 1× buffer in a 15 mL tube was added a solution of TCEP hydrochloride (1.074 mg in bio-grade purified water) once. The resultant solution was shaken at rt for 1 hr, then desalted and washed with two Amicon Ultra-4 centrifugal filters (30K MWCO). The filters were spinned at 4K g for 40 mins and the filtrates were discarded. 3 mL of bio-grade purified water was added to each filter for each wash (spinned at 14K g for 10 mins) and the wash process was repeated 3 times. The decapped HSA was dissolved in water (~20 mL in total). The solution was transferred to a 50 mL Falcon tube, and lyophilized to give a crystalline powder (500 mg).

The pure product was analyzed by UPLC-MS (Analytical method F; measured: 66439.0; expected: 66437).

Determination of the Number of Free Thiol Group in Decapped HSA

To a solution of this decapped HSA (2 mg) in 400 μL of PBS pH 7.4 in a 2 mL tube was added a solution of 6-maleimidohexanoic acid (13 μg) in water. The resultant solution was shaken at rt for 2 hr. UPLC-MS (Analytical method G) showed mono-adduct formation only, measured: 66649.0; expected: 66648.

Decapping with DTT

To a solution of albumin (400 mg, Aldrich, lyophilized powder, from human serum) in 5 mL of PBS 1× buffer in a 15 mL tube was added a solution of DTT (0.232 μl, 2 mg/mL in bio-grade purified water) once. The resultant solution was shaken at rt for 2 hr, then desalted and washed with twenty Amicon Ultra-0.5 centrifugal filters (10K MWCO). The filters were spinned at 14K g for 10 mins and the filtrates were discarded. Bio-grade purified water was added to the top of each filter for each wash (spinned at 14K g for 10 mins) and the wash process was repeated 6 times. The decapped HSA was dissolved in water (~20 mL in total). The solution was transferred to a 50 mL Falcon tube, and lyophilized to give a crystalline powder (376 mg).

The pure product was analyzed by UPLC-MS (Analytical method G; measured: 66438.5; expected: 66437).

Determination of the Number of Free Thiol Group in Decapped HSA

To a solution of this decapped HSA (3 mg) in 400 μL of PBS pH 7.4 in a 2 mL tube was added a solution of 3-maleimidopropionic acid (25 μg) in water. The resultant solution was shaked at rt overnight. UPLC-MS (Analytical method G) showed mono-adduct formation only, measured: 66608.0; expected: 66606.

Decapping with Cysteine

To a solution of albumin (120 mg, Aldrich, lyophilized powder, from human serum) in 1 mL of 50 mM PBS buffer pH 8.0 in a 2 mL tube was added cysteine (10.94 mg) once. The resultant solution was shaked at rt for 1 hr, then desalted and washed with two Amicon Ultra-0.5 centrifugal filters (10K MWCO). The filters were spinned at 14K g for 10 mins and the filtrates were discarded. Bio-grade purified water was added to the top of each filter for each wash (spinned at 14K g for 10 min) and the wash process was repeated 5 times. The decapped HSA was dissolved in water (4 mL in total). The solution was transferred to a 15 mL Falcon tube, and lyophilized to give a crystalline powder (108 mg).

The pure product was analyzed by UPLC-MS (Analytical method G; measured: 66439; expected: 66437).

Determination of the Number of Free Thiol Group in Decapped HSA

To a solution of this decapped HSA (3 mg) in 500 μL of PBS pH 7.4 in a 2 mL tube was added a solution of 3-maleimidopropionic acid (15 μg) in water. The resultant solution was shaked at rt for 1 hr. UPLC-MS (Analytical method G) showed mono-adduct formation only, measured: 66608.0; expected: 66606.

Step 2

Synthesis of Peptide-Linker Construct 1

PPA-O2Oc-O2Oc-O2Oc-O2Oc-Q-R-P-C*-L-S-C*-K-G-P-(D-Nle)Phenethylamine (SEQ ID NO: 62) wherein PPA is 3-(pyridin-2-yldisulfanyl)propanoic acid Phenethylamine-Pol ↓ SPPS (TPA: 3-mercaptopropanoic acid)

(1a)

(Trt)TPA-O$_2$Oc-O$_2$Oc-O$_2$Oc-O$_2$Oc-Q-R(Pbf)-P-C(Trt)-L-S(tBu)-C(Trt)-K(tBoc)-G-P-(D-Nle)Phenethylamine-Pol ↓ 1. Cleavage/PG Removal
   2. Purification (1b)

TPA-O$_2$Oc-O$_2$Oc-O$_2$Oc-O$_2$Oc-Q-R-P-C-L-S-C-K-G-P-(D-Nle)Phenethylamine

↓ 1. Cyclization
   2. Purification

TPA-O₂Oc-O₂Oc-O₂Oc-O₂Oc-Q-R-P-C-L-S-C-K-G-P-(D-Nle)Phenethylamine (1c)

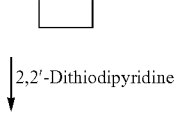
2,2'-Dithiodipyridine

PPA-O₂Oc-O₂Oc-O₂Oc-O₂Oc-Q-R-P-C-L-S-C-K-G-P-(D-Nle)Phenethylamine  Peptide-Linker Construct 1

(SEQ ID NOS 63, 62, 62, and 62, respectively, in order of appearance)

Preparation of Intermediate 1a (Assembly of Linear Peptide) O2Oc-O2Oc-O2Oc-O2Oc-Q-R-P-C*-L-S-C*-K-G-P-(D-Nle)Phenethylamine (SEQ ID NO: 62)

Phenethylamine-AMEBA resin (Aldrich, 0.25 mmol) is subjected to solid phase peptide synthesis on the Liberty™ microwave peptide synthesizer. Coupling is performed as follows:

| Coupling | AA | Number of couplings × Reaction time | Temperature °C. | Microwave power |
|---|---|---|---|---|
| 1 | D-Nle | 1 × 7.5 min | 50 | 20 |
| 2 | P | 1 × 7.5 min | 50 | 20 |
| 3 | G | 1 × 7.5 min | 50 | 20 |
| 4 | K(tBoc) | 1 × 7.5 min | 50 | 20 |
| 5 | C(Trt) | 1 × 2 min | 50 | 0 |
|   |   | 1 × 4 min | 50 | 25 |
| 6 | S(tBu) | 1 × 7.5 min | 50 | 20 |
| 7 | L | 1 × 7.5 min | 50 | 25 |
| 8 | C(Trt) | 1 × 2 min | 50 | 0 |
|   |   | 1 × 4 min | 50 | 25 |
| 9 | P | 1 × 7.5 min | 50 | 25 |
| 10 | R(Pbf) | 2 × 42 min | 50 | 0 |
|    |        | 2 × 7.5 min | 50 | 25 |
| 11 | Q(Trt) | 1 × 7.5 min | 50 | 25 |
| 12 | O2Oc | 1 × 7.5 min | 50 | 25 |
| 13 | O2Oc | 1 × 7.5 min | 50 | 25 |
| 14 | O2Oc | 1 × 7.5 min | 50 | 25 |
| 15 | O2Oc | 1 × 7.5 min | 50 | 25 |
| 16 | TPA(Trt) | 1 × 7.5 min | 50 | 25 |

Preparation of Intermediate 1b (Cleavage from the Resin with Concomitant Protecting Group Removal then Purification)

A solution made of 1.54 g of DTT and 0.75 mL of thioanisole in 6 mL of TFA/TIPS/Water (95:2.5:2.5) is added to Intermediate 1a (0.25 mmol) and the suspension is shaken at rt for 5 hr. The cleavage solution is filtered off and the resin is washed with 95% aq. TFA. The combined cleavage and washing solutions are poured onto cold diethyl ether, giving a precipitate. The suspension is centrifuged and the supernatant poured off. Diethyl ether is added to the residue, the suspension is vortexed for 3 min, centrifuged, and the supernatant is poured off. The washing process is repeated 3 times. The solid is dried in high vacuum. The crude is purified by preparative HPLC and lyophilized from ACN/H₂O to afford Intermediate 1b.

Preparation of Intermediate 1c (Cyclization and Purification

Intermediate 1b is dissolved in H₂O (2.0 mL). A solution of 50 mM I₂ in AcOH (1.3 eq) is added in one portion to the stirred solution and the solution is stirred overnight at rt and LC/MS shows completion of the reaction. 0.5 M Ascorbic acid in H₂O is added to quench the excess of I₂. The crude is purified by preparative HPLC and lyophilized from ACN/H₂O to afford Intermediate 1c.

Preparation of Peptide-Linker Construct Intermediate 1c

A mixture of Intermediate 1c, 2,2'-dithiodipyridine (3 eq) in ACN is shaked at 25° C. for 1 hr. The reaction mixture is diluted with MeOH and filtered. The solution is purified by preparative HPLC and lyophilized from ACN/H₂O to afford Peptide-Linker Construct 1.

Step 3: Peptide-Linker Construct/Albumin Conjugation

A solution of decapped HSA (100 mg) in PBS buffer (6 mL) is treated with a solution of PPA-O2Oc-O2Oc-O2Oc-O2Oc-Q-R-P-C*-L-S-C*-K-G-P-(D-Nle)Phenethylamine (SEQ ID NO: 62) (2 eq in water). The resultant solution is shaked at rt for 1 hr, then desalted and washed with 4 Amicon Ultra-0.5 centrifugal filters (10K MWCO). The filters are spinned at 13K g for 10 mins and the filtrates are discarded. Bio-grade purified water is added to the top of each filter for each wash (spinned at 13K g for 10 mins) and the wash process is repeated 6 times. The conjugate is dissolved in water (4 mL in total). The solution is transferred to a 15 mL Falcon tube, and lyophilized to give Example 39.

Example 40

Apelin Cyclic Peptide Conjugated to a Fatty Acid Via a BUN-PEG Linker

Step 1: Preparation of Apelin Cyclic Peptide-BCN Construct: Preparation of pE-R-P-C*-L-S-C*-N⁶-[[(1α,8α,9α)-Bicyclo[6.1.0]non-4-yn-9-ylmethoxy]carbonyl]-K-G-P-(D-Nle)-NH(Phenethyl) [Disulfide C4-C7] (SEQ ID NO: 64)

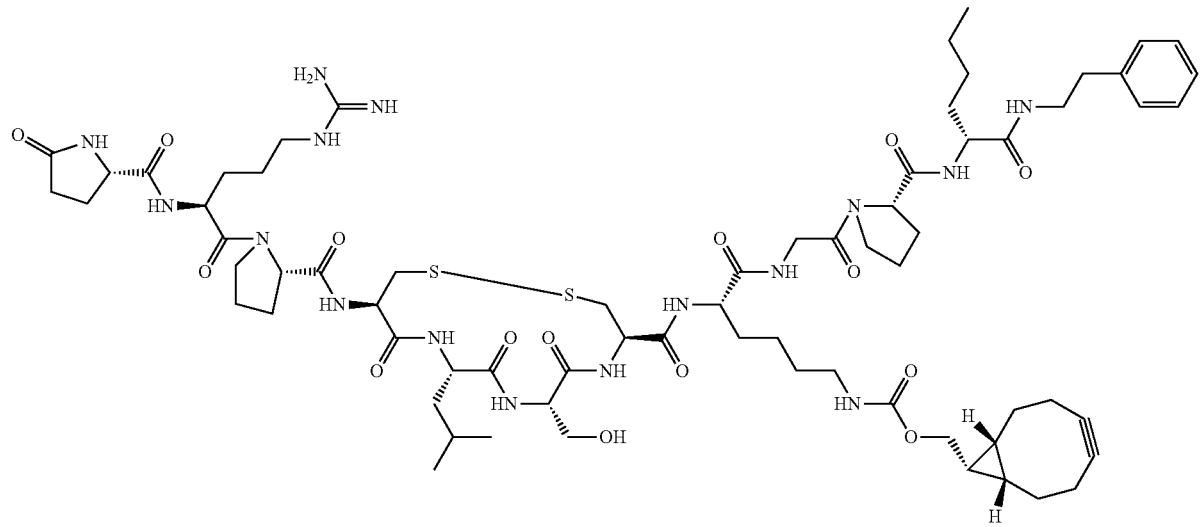 [SMILES: CCCC[C@@H](NC(=O)[C@@H]1CCCN1C(=O)CNC(=O)[C@H](CCCCNC(=O)OC[C@@H]1[C@@H]2CCC#CCC[C@@H]21)NC(=O)[C@@H]1CSSC[C@H](NC(=O)[C@@H]2CCCN2C(=O)[C@H](CCCNC(=N)N)NC(=O)[C@@H]2CCC(=O)N2)C(=O)N[C@@H](CC(C)C)C(=O)N[C@@H](CO)C(=O)N1)C(=O)NCCc1ccccc1]

A mixture of pE-R-P-C*-L-S-C*-K-G-P-(D-Nle)-NH(Phenethyl) triacetate [disulfide C4-C7] (SEQ ID NO: 50) (Example 32: 100 mg, 0.068 mmol), sodium bicarbonate (38 mg, 0.452 mmol) and water (83 uL) in DMF (1 mL) was stirred at RT for 10 mins, then (1R,8S)-bicyclo[6.1.0]non-4-yn-9-ylmethyl succinimidyl carbonate (Berry &associates, 20 mg, 0.068 mmol) was added. The reaction mixture was stirred at RT for 90 mins. 1 mL of water was added to the mixture, and the resultant solution was lyophilized to give a powder which was used for the next step without further purification.

Step 2: Di-tert-butyl 2-(undec-10-yn-1-yl)malonate

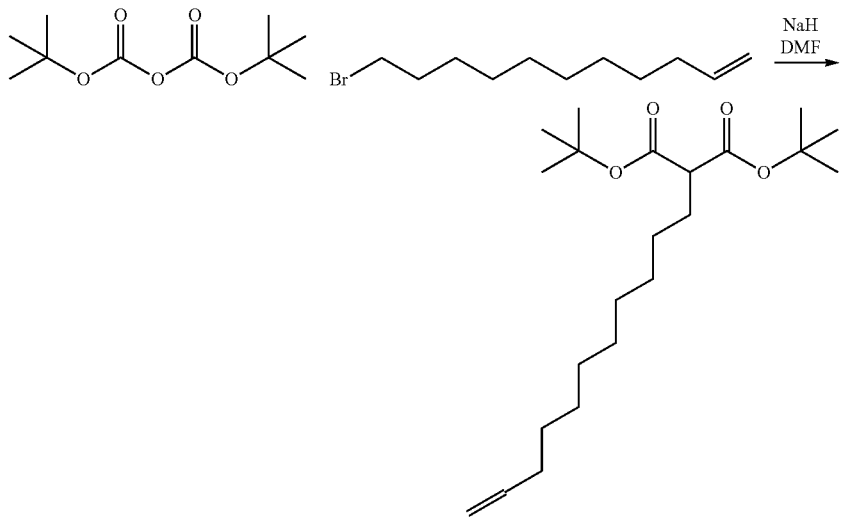

Di-tert-butyl malonate (800 mg, 3.70 mmol) is dissolved in DMF (9 mL) at 0° C. under N₂ and NaH (148 mg, 3.70 mmol) is added. The reaction is stirred 30 minutes at 0° C. and 11-bromo-dec-1-ene (3.33 mmol) is added slowly dropwise, resulting in a yellow solution. The reaction is stirred at 0° C. for 2 hours then warmed to r.t. and stirred for 16 hours. The mixture is taken up in EtOAc (75 mL) and washed with H₂O (25 mL). The aqueous layer is extracted with EtOAc (75 mL) and the combined organic layers are dried over Na₂SO₄, filtered and concentrated. The mixture is purified via flash column (12 g silica cartridge, 0-20% EtOAc/heptanes) and fractions are concentrated to yield the desired product.

Step 3: 11,11-di-tert-butyl 1-ethyl docos-21-ene-1,11,11-tricarboxylate

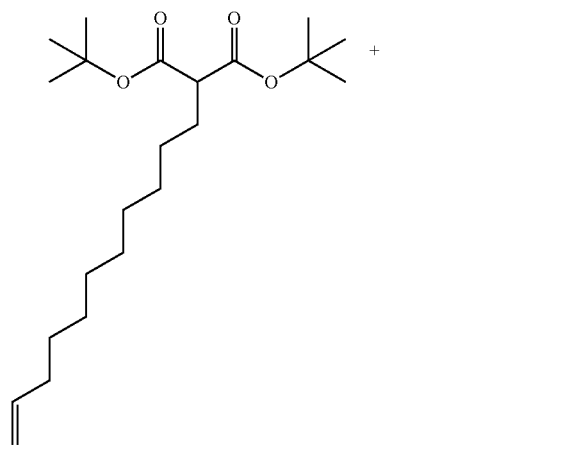

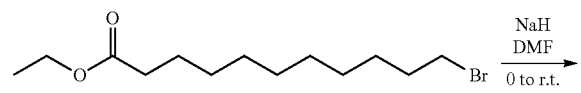

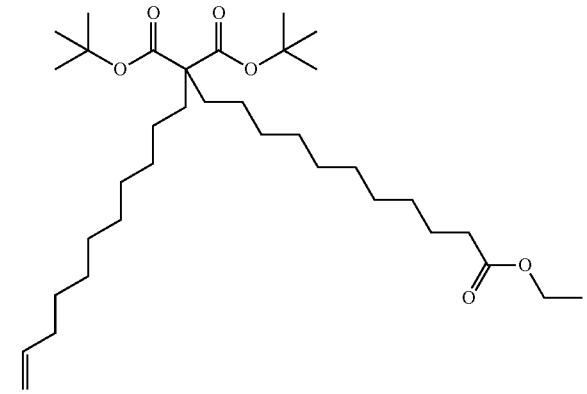

Compound from step 2 (0.442 mmol) is dissolved in DMF (2 mL) at 0° C. and NaH (21.23 mg, 0.531 mmol) is added. The reaction stirred at 0° C. for 15 minutes and ethyl 11-bromoundecanoate (143 mg, 0.486 mmol) is added slowly dropwise. The reaction is warmed to r.t. and stirred for 16 hours. The mixture is diluted with EtOAc (40 mL) and washed once with H₂O (20 mL). The aqueous layer is extracted once with EtOAc (40 mL) and the organic layers are combined, dried over Na₂SO₄, filtered and concentrated. The sample is dissolved in 1 mL DCM and purified via flash column (12 g silica column, 0-20% EtOAc/heptane, 15 min). The fractions are combined and concentrated to give the desired product.

Step 4: 12,12-bis(tert-butoxycarbonyl)tricos-22-enoic acid

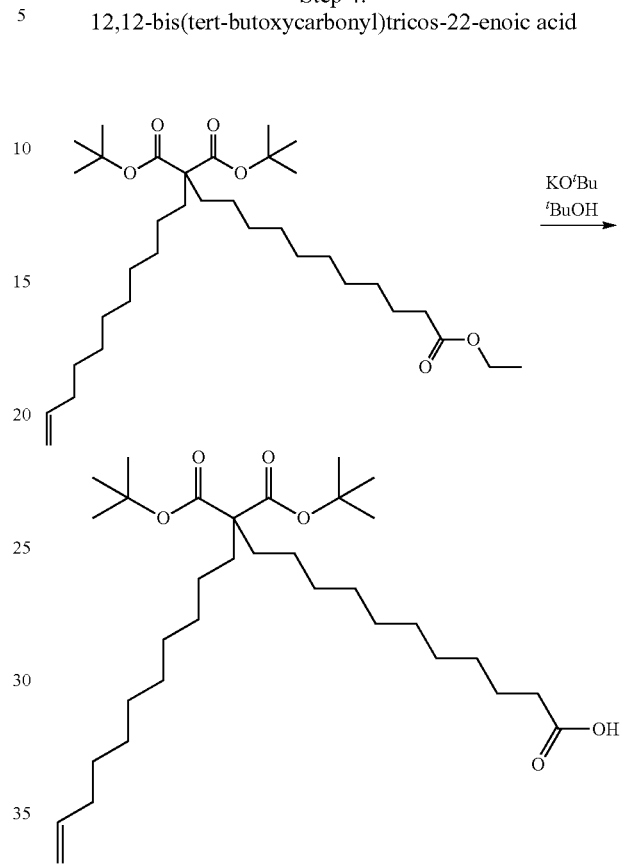

To a solution of compound from step 3 (0.037 mmol) in ᵗBuOH (1 mL) is added a solution of KOtBu (114 mg, 1.012 mmol) in ᵗBuOH (2 mL) at 30° C. under N₂. The mixture is stirred at r.t. and monitored by TLC (1:1 EtOAc/hexanes, KMnO₄, reflux). After the reaction is completed, the reaction mixture is quenched with 1 M HCl (20 mL) and extracted twice with EtOAc (25 mL). The organic layers are combined, dried over Na₂SO₄, filtered and concentrated. The material was carried on to the next step without further purification.

Step 5: Docos-21-ene-1,11,11-tricarboxylic acid

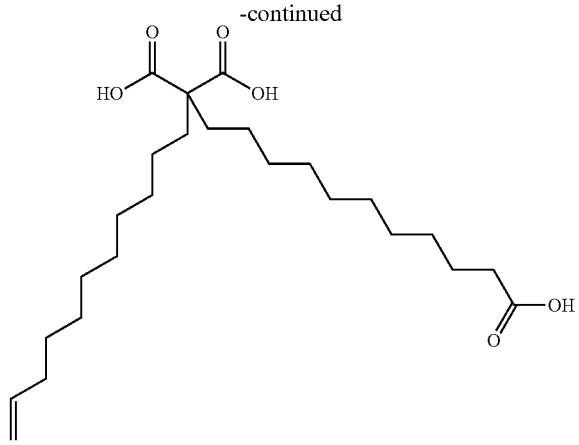

TFA (2 mL) is added to a compound from step 4 (0.022 mmol) and the reaction is stirred at r.t. for 1 hour. The mixture is diluted with DCM (10 mL) and concentrated. The material is taken up in EtOAc (10 mL) and washed with $H_2O$ (20 mL). The organic layer is dried over $Na_2SO_4$, filtered and concentrated. The crude material is dissolved in 1 mL MeOH and purified via MS-triggered HPLC (Sunfire 30×50 mm 5 um column ACN/$H_2O$ w/ 0.1% TFA 75 ml/min, 1.5 ml injection, 45-70% ACN over 3.5 min).

Step 6: 2-(((2,5-Dioxopyrrolidin-1-yl)oxy)carbonyl)-2-(undec-10-en-1-yl)tridecanedioic acid

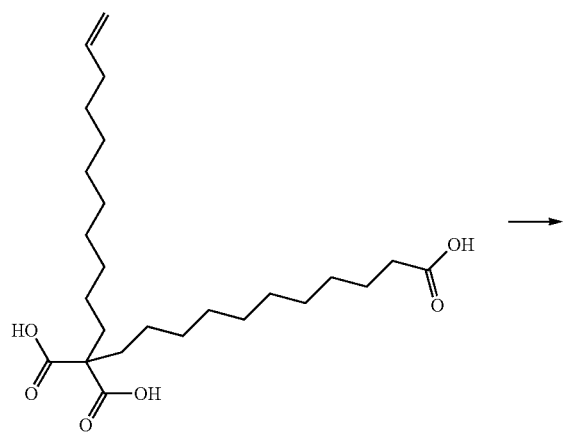

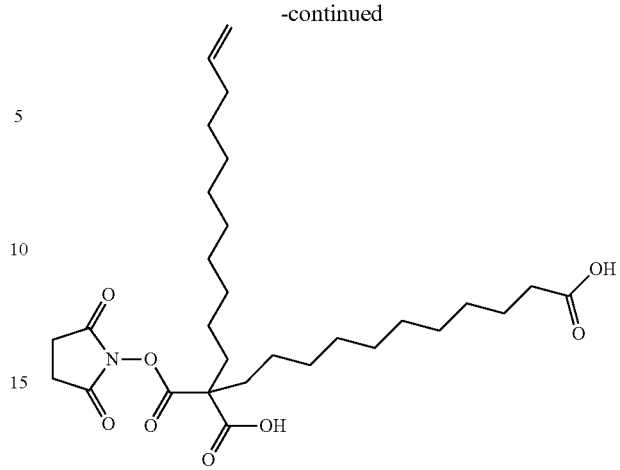

DCC (187 mg, 0.908 mmol) in DCM (2 mL) was added to a solution of N-hydroxysuccinimide (99 mg, 0.862 mmol) and docos-21-ene-1,11,11-tricarboxylic acid (Intermediate 45: 400 mg, 0.908 mmol) in DCM (7 mL) and THF (0.7 mL). The reaction was stirred overnight before the solvent was evaporated. The residue was purified by HPLC (Sunfire C18 30×50 mm; 55-80% ACN/water+0.1% TFA) to yield the title compound (155 mg, 0.288 mmol, 32%): by LCMS Method E Rt=1.51 min, M+H 538.3; $^1$H NMR (400 MHz, CHLOROFORM-d) δ ppm 1.16-1.46 (m, 28H) 1.60-1.87 (m, 3H) 1.91-2.17 (m, 5H) 2.38 (t, J=7.03 Hz, 2H) 2.86 (br. s., 4H) 3.68 (dd, J=11.25, 7.34 Hz, 1H) 3.78 (dd, J=11.31, 5.20 Hz, 1H) 3.99-4.10 (m, 1H).

Step 7: Fatty Acid-PEG Linker

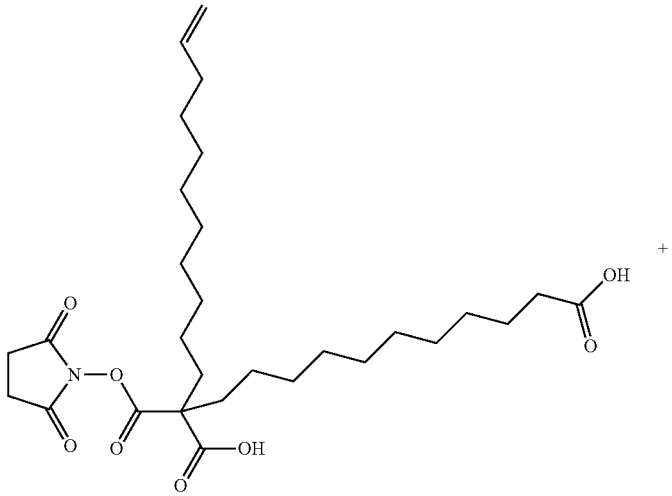

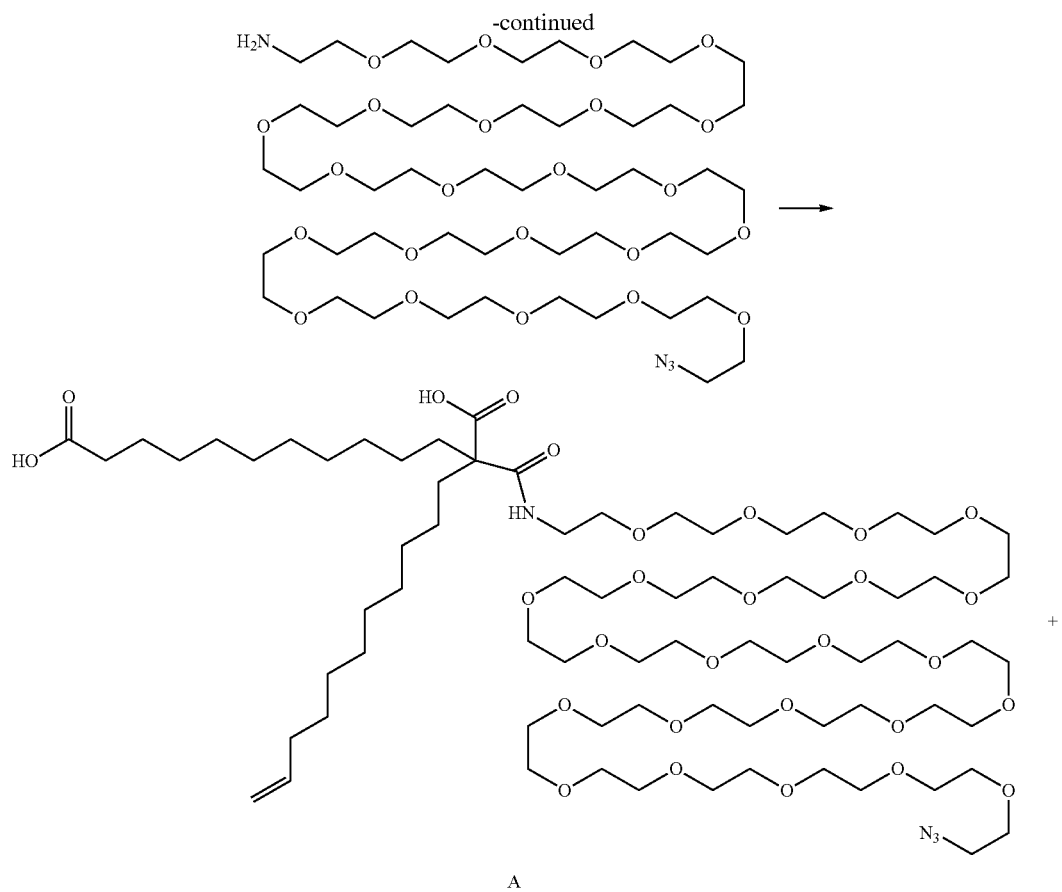

A

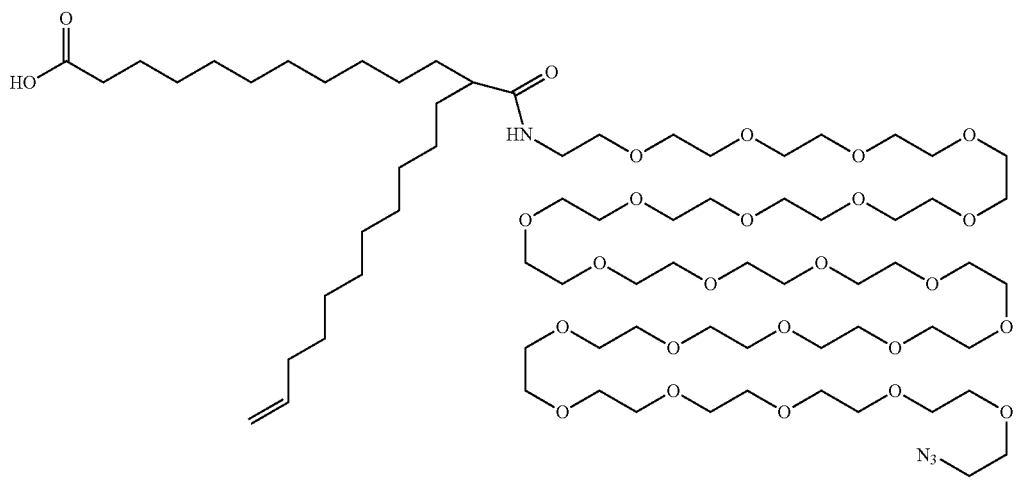

B

Azido-dPEG23-amine (Quanta Biodesign: 164 mg, 0.149 mmol) and compound from step 6 (80 mg, 0.149 mmol) were dissolved in THF (2.5 mL). DIPEA (394, 0.233 mmol) was added and the reaction agitated overnight. The solvent was evaporated and the residue purified by HPLC (Sunfire C18 30×50 mm; 45-70% ACN/water+0.1% TFA) to yield compounds A (97 mg, 0.061 mmol, 41%) and B (32 mg, 0.021 mmol, 14%): LCMS ZQ1 Method E Rt=1.35 min, [M+2H]$^{+2}$ 761.9; $^1$H NMR (400 MHz, ACETONITRILE-d3) δ ppm 1.05-1.18 (m, 3H) 1.19-1.32 (m, 20H) 1.36 (t, J=7.15 Hz, 1H) 1.48-1.59 (m, 2H) 1.65-1.75 (m, 2H) 2.01-2.06 (m, 2H) 2.25 (t, J=7.46 Hz, 2H) 3.33-3.39 (m, 2H) 3.39-3.44 (m, 2H) 3.50-3.67 (m, 98H) 4.84-4.95 (m, 1H) 4.95-5.06 (m, 1H) 5.83 (ddt, J=17.07, 10.29, 6.68, 6.68 Hz, 1H) 7.31 (t, J=5.44 Hz, 1H); LCMS method E Rt=1.50 min, [M+2H]$^{+2}$ 739.9; $^1$H NMR (400 MHz, ACETONITRILE-d3) ppm 1.16-1.42 (m, 30H) 1.42-1.63 (m, 5H) 2.00-2.07 (m, 2H) 2.22-2.28 (m, 2H) 2.40-2.52 (m, 2H) 3.25-3.33 (m, 2H) 3.33-3.42 (m, 2H) 3.42-3.50 (m, 2H) 3.50-3.68 (m, 88H) 4.86-5.06 (m, 2H) 5.83 (ddt, J=17.04, 10.26, 6.71, 6.71 Hz, 1H) 6.40-6.74 (m, 1H).

Step 8: Preparation of Example 40
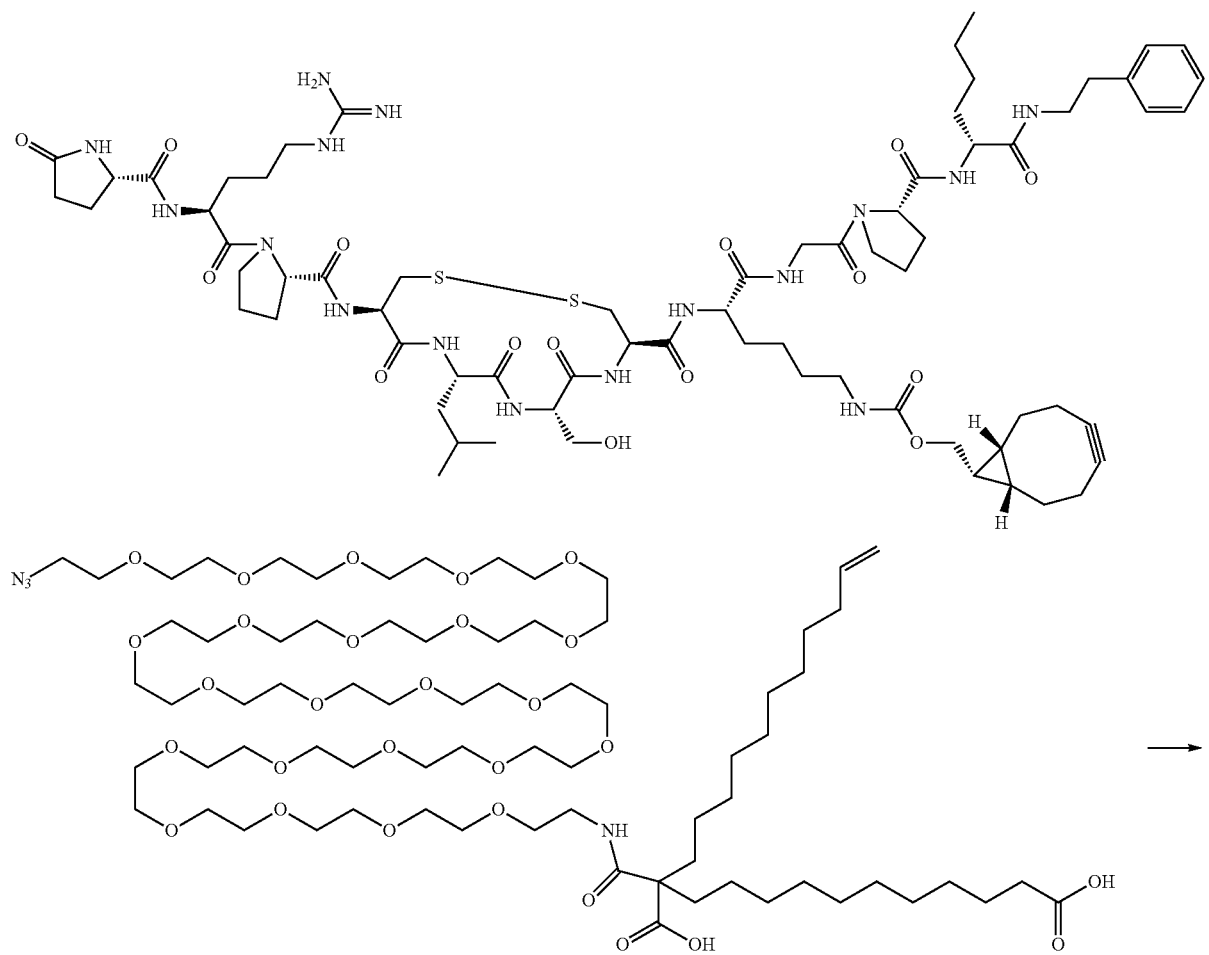 [SMILES: CCCC[C@@H](NC(=O)[C@@H]1CCCN1C(=O)CNC(=O)[C@H](CCCCNC(=O)OC[C@@H]1[C@@H]2CCC#CCC[C@@H]21)NC(=O)[C@@H]1CSSC[C@H](NC(=O)[C@@H]2CCCN2C(=O)[C@H](CCCNC(=N)N)NC(=O)[C@@H]2CCC(=O)N2)C(=O)N[C@@H](CC(C)C)C(=O)N[C@@H](CO)C(=O)N1)C(=O)NCCc1ccccc1 ; C=CCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCN=[N+]=[N-]]
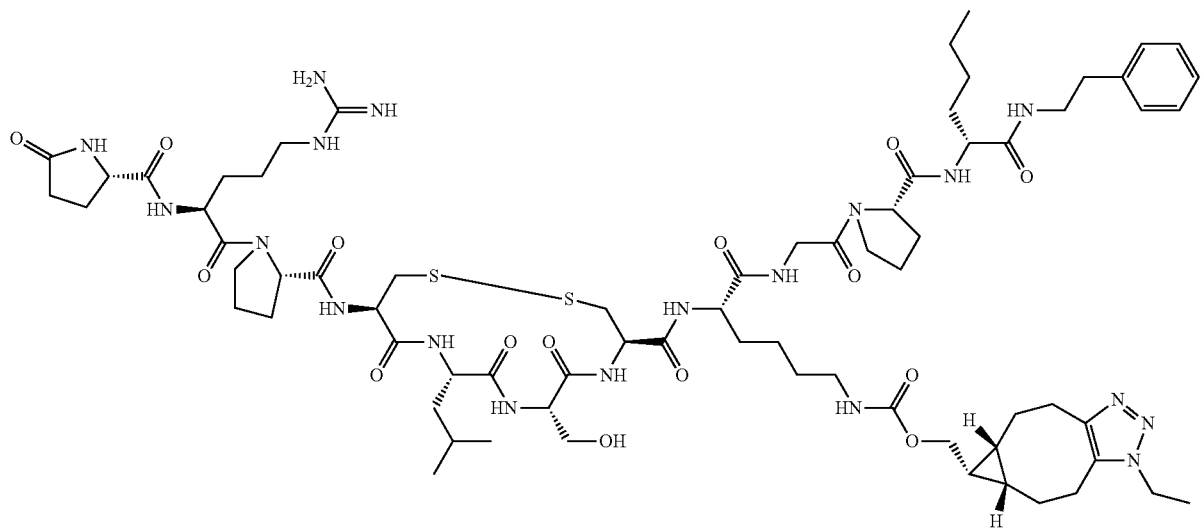
Example 40

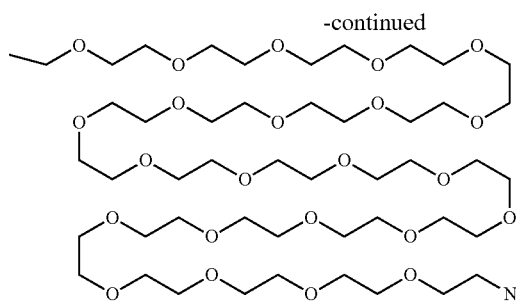
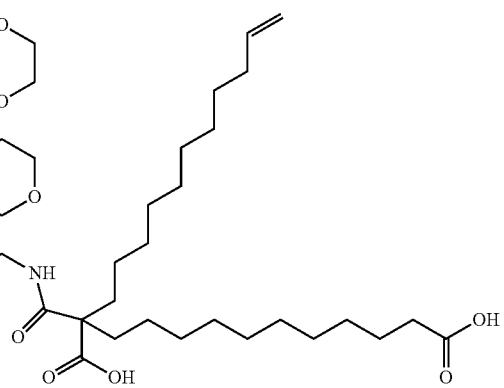

A mixture of pE-R-P-C*-L-S-C*-N⁶-[[(1α,8α,9α)-bicyclo[6.1.0]non-4-yn-9-ylmethoxy]carbonyl]-K-G-P-(D-Nle)-NH(Phenethyl) [disulfide C4-C7] (SEQ ID NO: 64) (50 mg of the product from step 1 in 1 mL of water, 0.034 mmol) and compound A from step 7 (52 mg, in 268 uL of water) was stirred at RT for about 3 hrs. The reaction mixture was then purified by preparative HPLC (Sunfire 30×50 mm 5 um column ACN/H2O w/ 0.1% TFA 75 ml/min, 15-40% ACN 5 min gradient). The product fraction was lyophilized to give the titled product as TFA salt (24 mg, 21%). LCMS (Waters Acquity UPLC BEH C18 1.7 um 2.1×50 mm, 50° C., Eluent A: Water+0.1% Formic Acid, Eluent B: Acetonitrile+0.1% Formic Acid, gradient 2% to 98% B/A over 5.15 mins): Retention time: 2.77 mins; MS [M+2]$^2$: observed: 1491.8808, calculated: 1491.8560.

Example 41

Apelin Cyclic Peptide Conjugate to a Fatty Acid at the N-Terminus

Step 1: Synthesis of A-H-Q-R-P-C-L-S-C-K-G-P-DNle-Phenethyl Amine (SEQ ID NO: 65) Intermediate 41a Phenethylamine-AMEBA resin (Sigma Aldrich, 0.1 mmol, 1.0 mmol/g) was subjected to solid phase peptide synthesis on an automatic peptide synthesizer (CEM Liberty Blue Microwave) with standard double Arg for the Arg residues and DNle coupled double time. Amino acids were prepared as 0.2 M solutions in DMF. A standard coupling cycle was defined as follows:

Amino acid coupling: AA (5 eq.), HATU (5 eq.), DIEA (25 eq.)
Washing: DMF (3×7 mL)
Fmoc Deprotection: 20% Piperidine/0.1 M HOBt (2×7 mL)
Washing: DMF (4×7 mL then 1×5 mL)

| Coupling | AA | Number of couplings × Reaction time (Temp) | Coupling Method |
|---|---|---|---|
| 1 | Fmoc-D-Nle-OH | 1 × 10 min (70° C.) | DIEA/HATU |
| 2 | Fmoc-L-Pro-OH | 1 × 5 min (70° C.) | DIEA/HATU |
| 3 | Fmoc-L-Gly-OH | 1 × 5 min (70° C.) | DIEA/HATU |
| 4 | Fmoc-L-Lys-OH | 1 × 5 min (70° C.) | DIEA/HATU |
| 5 | Fmoc-L-Cys-OH | 1 × 5 min (70° C.) | DIEA/HATU |
| 6 | Fmoc-L-Ser-OH | 1 × 5 min (70° C.) | DIEA/HATU |
| 7 | Fmoc-L-Leu-OH | 1 × 5 min (70° C.) | DIEA/HATU |
| 8 | Fmoc-L-Cys-OH | 1 × 5 min (70° C.) | DIEA/HATU |

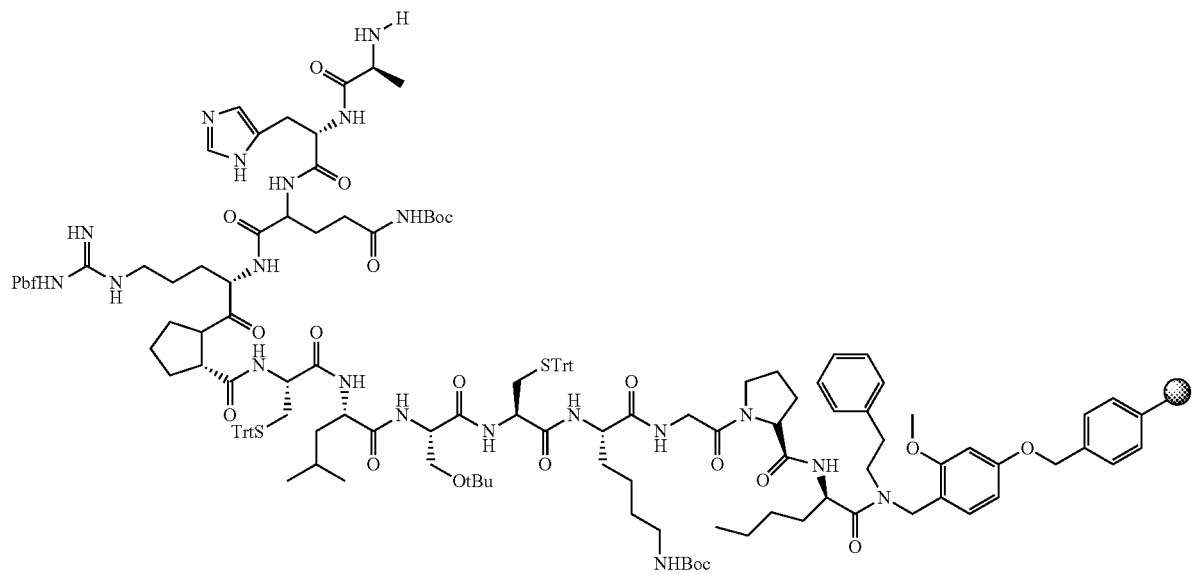

-continued

| Coupling | AA | Number of couplings × Reaction time (Temp) | Coupling Method |
|---|---|---|---|
| 9 | Fmoc-L-Pro-OH | 1 × 5 min (70° C.) | DIEA/HATU |
| 10 | Fmoc-L-Arg-OH | 2 × 25 min (25° C.) | DIEA/HATU |
| 11 | Fmoc-L-Gln-OH | 1 × 5 min (70° C.) | DIEA/HATU |
| 12 | Fmoc-L-His-OH | 1 × 5 min (70° C.) | DIEA/HATU |
| 13 | Fmoc-L-Ala-OH | 1 × 5 min (70° C.) | DIEA/HATU |

After the assembly of the peptide, the resin was washed with DMF (2×50 mL) and DCM (2×50 mL) then dried under vacuum to give Intermediate 41a (276 mg, 0.1 mmol).

Step 2: Preparation of Intermediate 41b (Cleavage of Peptide from Resin)

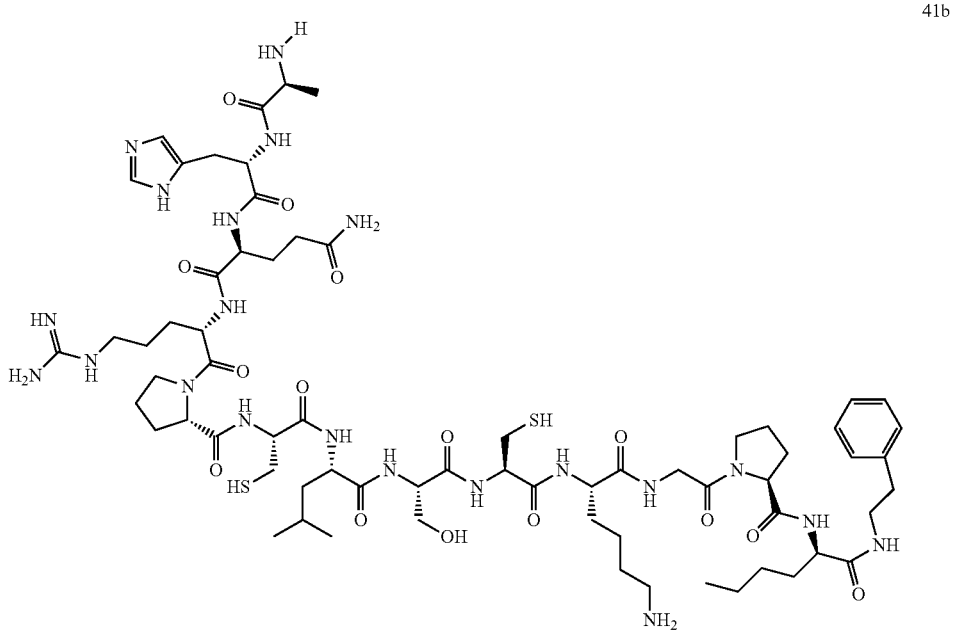 [SMILES: CCCC[C@@H](NC(=O)[C@@H]1CCCN1C(=O)CNC(=O)[C@H](CCCCN)NC(=O)[C@H](CS)NC(=O)[C@H](CO)NC(=O)[C@H](CC(C)C)NC(=O)[C@H](CS)NC(=O)[C@@H]1CCCN1C(=O)[C@H](CCCNC(=N)N)NC(=O)[C@H](CCC(N)=O)NC(=O)[C@H](Cc1cnc[nH]1)NC(=O)[C@H](C)N)C(=O)NCCc1ccccc1]

41b

Intermediate 41a (276 mg, 0.1 mmol) was combined with 4 mL TFA solution (37 mL TFA, 1 mL $H_2O$, 1 mL TIPS, 3.06 g DTT) and shaken at r.t. for 3 hours. The solution was removed from the resin and precipitated into 40 mL cold $Et_2O$. The solution was vortexed and let stand over ice for 10 minutes before centrifuging at 4000 rpm for 5 minutes. The solvent was removed and the white solid was washed twice more with cold $Et_2O$ (40 mL each time), centrifuged (5 minutes each time) and decanted. The solid was dried under vacuum overnight yielding Intermediate 41b-batch 1 (17.4 mg, 0.012 mmol). LCMS (SQ2 ProductAnalysis-Acidic-Peptide-Polar, Acquity UPLC BEH C18 column, 130 Å, 1.7 μm, 2.1 mm×50 mm, 50° C.): $R_t$=1.83 minutes, MS [M+H] 1513.5.

Step 3: Preparation of Intermediate 41c (Cyclization of Cysteine Residues)

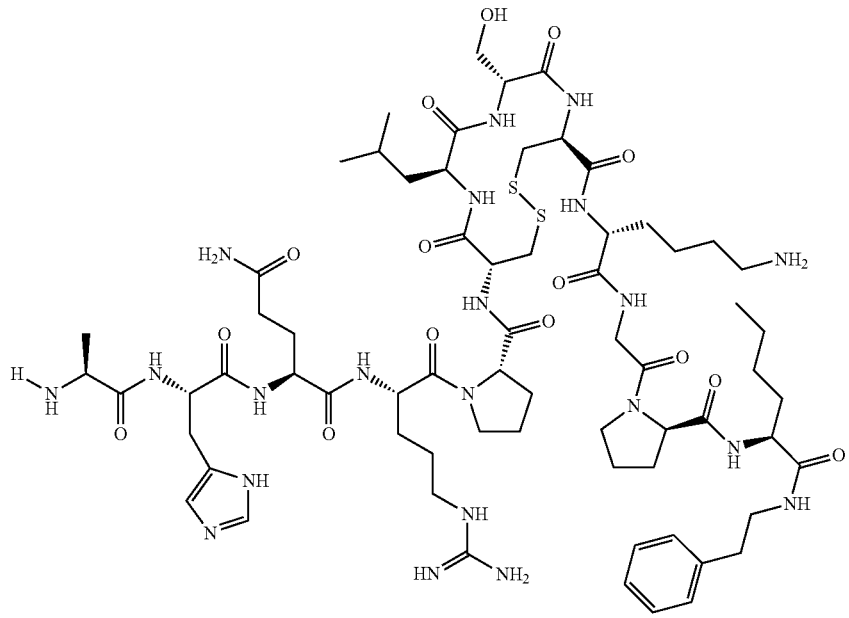

Intermediate 41b-batch1 and 2 (29.6 mg, 0.020 mmol) was dissolved in water (3 mL) and 10 drops of DMSO to give a slightly cloudy solution. Iodine (50 mM in HOAc, 0.783 mL, 0.039 mmol) was added slowly dropwise and the reaction was mixed at r.t. overnight. LCMS analysis of the crude reaction showed complete conversion of starting material. 0.5 M ascorbic acid was added dropwise until color dissipated. The material was purified via MS-triggered HPLC. Lyophilization of the pooled fractions gave 7 mg of the desired product as a white powder (4.63 µmol, 24%). LCMS (SQ2 ProductAnalysis-Acidic-Peptide, Acquity UPLC BEH C18 column, 130 Å, 1.7 µm, 2.1 mm×50 mm, 50° C.): $R_t$=0.90 minutes, MS [M+H] 1511.8.

Step 4: 1-Benzyl 3-tert-butyl 2-undecylmalonate

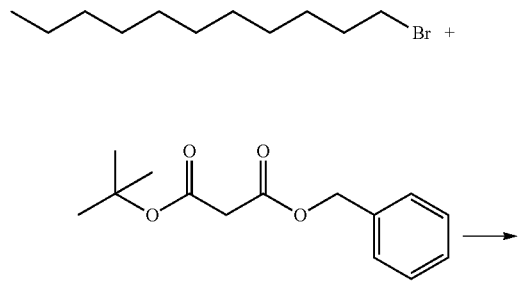

-continued

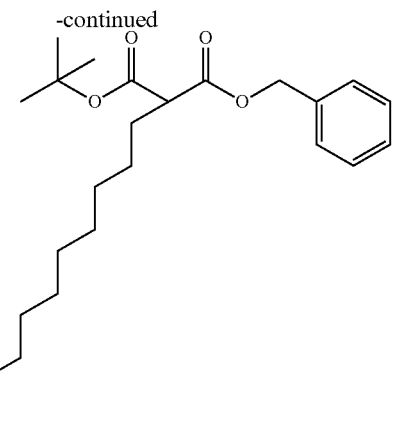

To a suspension of NaH (160 mg, 4.0 mmol) in DMF (8 mL) at 0° C. under $N_2$, was added benzyl tert-butyl malonate (1.0 g, 4.0 mmol) in DMF (2 mL). The mixture was stirred for 50 min after which 1-bromoundecane in DMF (2 mL) was added. After an additional hour of stirring the reaction was allowed to warm to room temperature. The reaction was maintained overnight. $Et_2O$ (100 mL) and water (20 mL) were added to partition the reaction. The aqueous phase was extracted with $Et_2O$ (100 mL), and the combined organics dried over $Na_2SO_4$. The solvent was evaporated and the residue purified by flash column (C18 12 g, 40-100% ACN/water+0.1% TFA) to yield the title compound as a colorless oil (1.14 g, 2.82 mmol, 71%): LCMS Method F Rt=1.58 min, M+Na 427.4; $^1$H NMR (400 MHz, CHLOROFORM-d) δ ppm 0.84-0.96 (m, 3H) 1.28 (br. s, 12H) 1.31 (m, J=3.90 Hz, 6H) 1.41 (s, 9H) 1.88 (q, J=7.38 Hz, 2H) 3.29 (t, J=7.58 Hz, 1H) 5.19 (q, J=12.27 Hz, 2H) 7.30-7.42 (m, 5H).

Step 5: 1,11-Dibenzyl 11-tert-butyl docosane-1,11,11-tricarboxylate

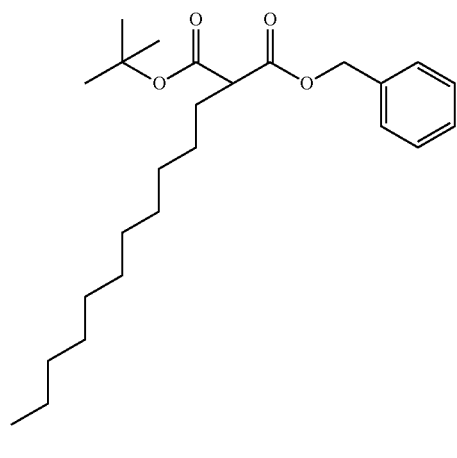

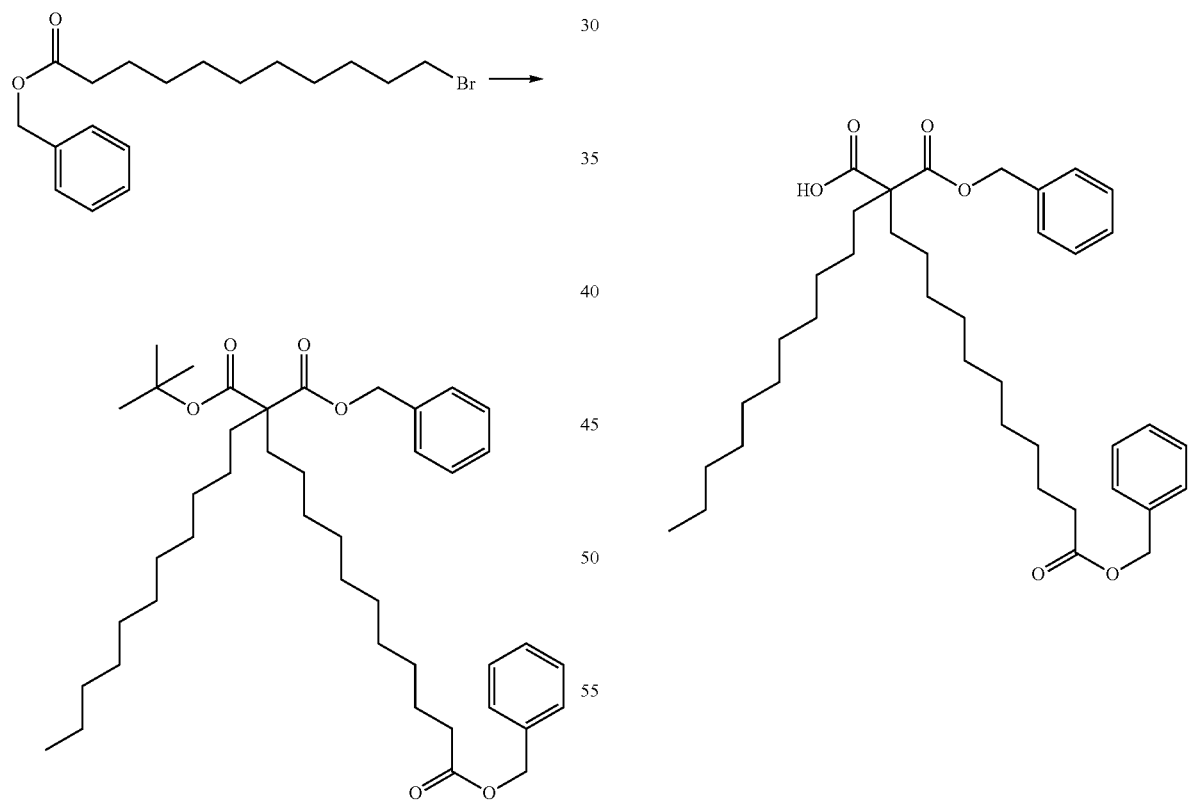

The title compound was synthesized in a fashion similar to step 3 of Example 40 using compound from step 4 (177 mg, 0.284 mmol) as a starting material to yield a colorless oil (153 mg, 0.213 mmol, 75%): $^1$H NMR (400 MHz, CHLOROFORM-d) δ ppm 0.86-0.93 (m, 3H) 1.12-1.21 (m, 2H) 1.21-

1.37 (m, 30H) 1.66 (quin, J=7.40 Hz, 2H) 1.89-2.07 (m, 4H) 2.37 (t, J=7.58 Hz, 2H) 2.84 (br. s., 4H) 5.13 (s, 2H) 5.25 (s, 2H) 7.30-7.47 (m, 10H).

Step 6: 13-(Benzyloxy)-2-((benzyloxy)carbonyl)-13-oxo-2-undecyltridecanoic acid

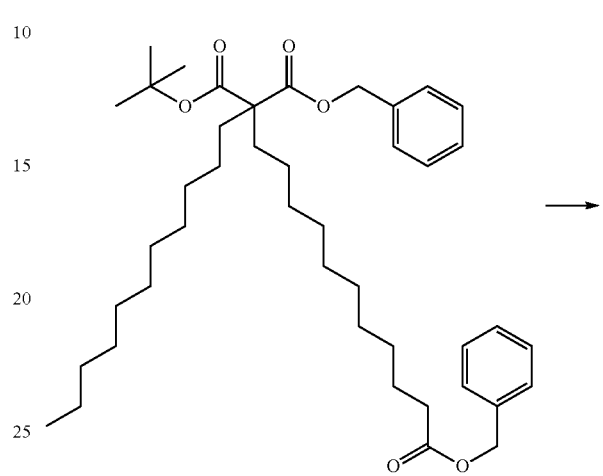

To a solution of a compound from step 5 (200 mg, 0.295 mmol) in DCM (3 mL) was added TFA (0.6 mL), and the reaction stirred at room temperature for 3 hrs. The solvent was evaporated and the residue purified by flash column (silica 12 g, 0-15% EtOAc/HEP) to yield the title compound (177 mg, 0.284 mmol, 96%): $^1$H NMR (400 MHz, CHLOROFORM-d) δ ppm 0.87-0.94 (m, 3H) 0.94-1.05 (m, 2H) 1.19 (br. s., 14H) 1.23-1.37 (m, 16H) 1.65 (quin, J=7.40 Hz, 2H) 1.78-1.91 (m, 2H) 1.93-2.05 (m, 2H) 2.37 (t, J=7.52 Hz, 2H) 5.14 (s, 2H) 5.27 (s, 2H) 7.31-7.44 (m, 10H).
Step 7: 1,11-Dibenzyl 11-(2,5-dioxocyclopentyl) docosane-1,11,11-tricarboxylate
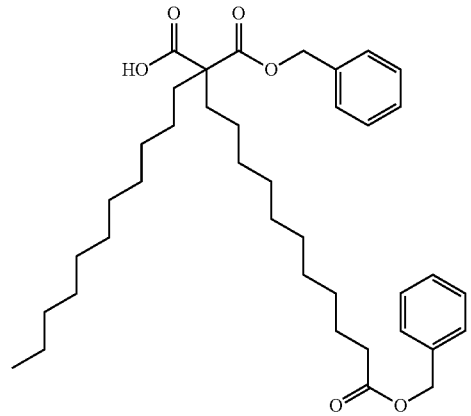
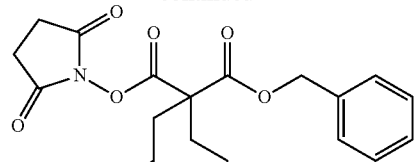
The title compound was synthesized in a fashion similar to step 6 of Example 40 using compound from step 6 (177 mg, 0.284 mmol) as a starting material to yield a colorless oil (153 mg, 0.213 mmol, 75%): $^1$H NMR (400 MHz, CHLOROFORM-d) δ ppm 0.86-0.93 (m, 3H) 1.12-1.21 (m, 2H) 1.21-1.37 (m, 30H) 1.66 (quin, J=7.40 Hz, 2H) 1.89-2.07 (m, 4H) 2.37 (t, J=7.58 Hz, 2H) 2.84 (br. s., 4H) 5.13 (s, 2H) 5.25 (s, 2H) 7.30-7.47 (m, 10H).
Step 8
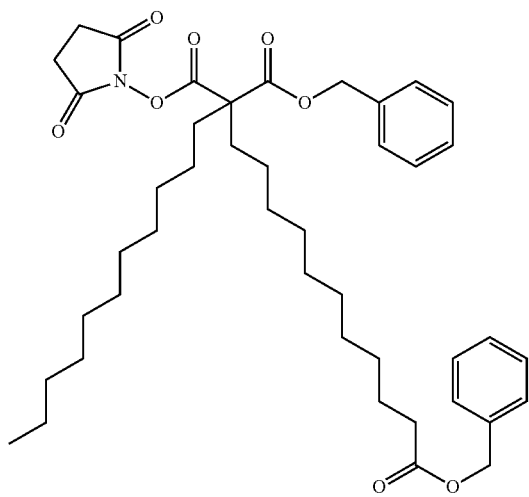
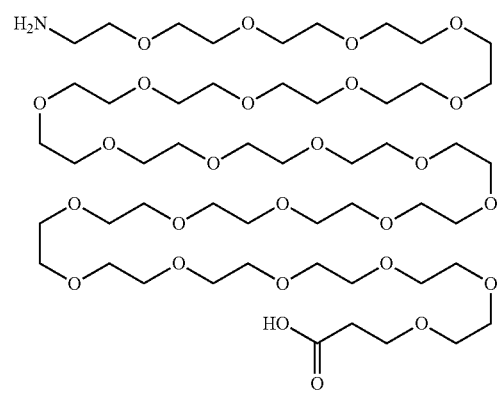

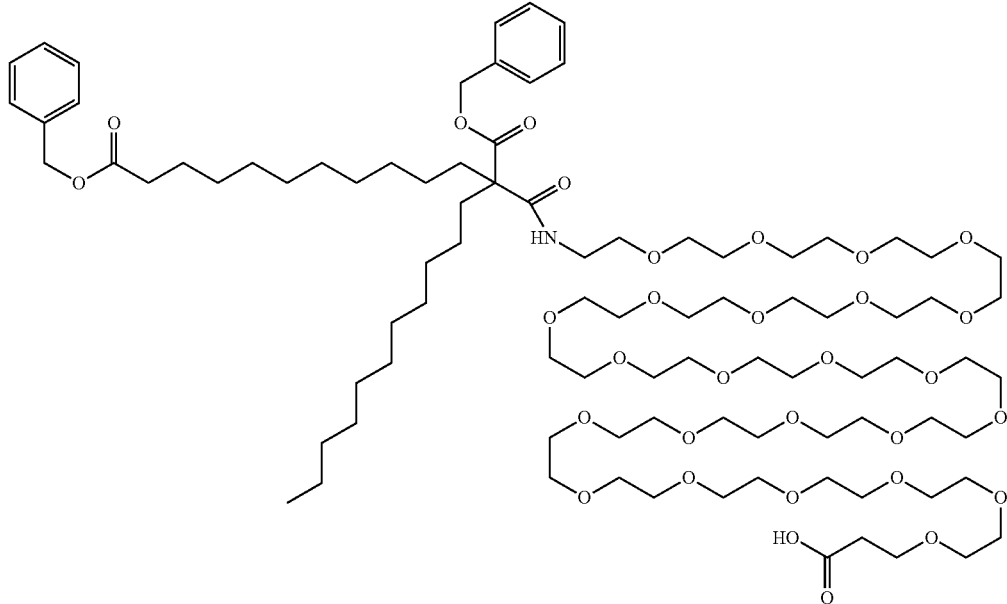

A solution of intermediate 34 (145 mg, 0.201 mmol) in THF (1.5 mL) and DCM (1.5 mL) was added to a vial charged with amino-PEG24-acid. DIPEA (884, 0.504 mmol) was added and the reaction agitated on a shaker plate for 15 hrs. The solvent was evaporated and the residue purified by supercritical fluid chromatography (Waters HILIC 20×150 mm; 15-25% MeOH/$CO_2$) to yield intermediate 35 (151 mg, 0.086 mmol, 43%): LCMS Method E Rt=1.30 min, [M+2H]+2 876.4; $^1$H NMR (400 MHz, CHLOROFORM-d) δ ppm 0.86-0.93 (m, 3H) 0.93-1.04 (m, 2H) 1.19 (br. s., 15H) 1.23-1.37 (m, 15H) 1.61-1.68 (m, 2H) 1.78 (td, J=12.44, 4.34 Hz, 2H) 1.92-2.05 (m, 2H) 2.37 (t, J=7.58 Hz, 2H) 2.62 (t, J=6.05 Hz, 2H) 3.49 (dd, J=6.72, 2.32 Hz, 2H) 3.52-3.59 (m, 2H) 3.59-3.73 (m, 92H) 3.80 (t, J=6.05 Hz, 2H) 5.13 (s, 2H) 5.18 (s, 2H) 7.31-7.42 (m, 10H) 8.09 (t, J=5.26 Hz, 1H).

Step 9

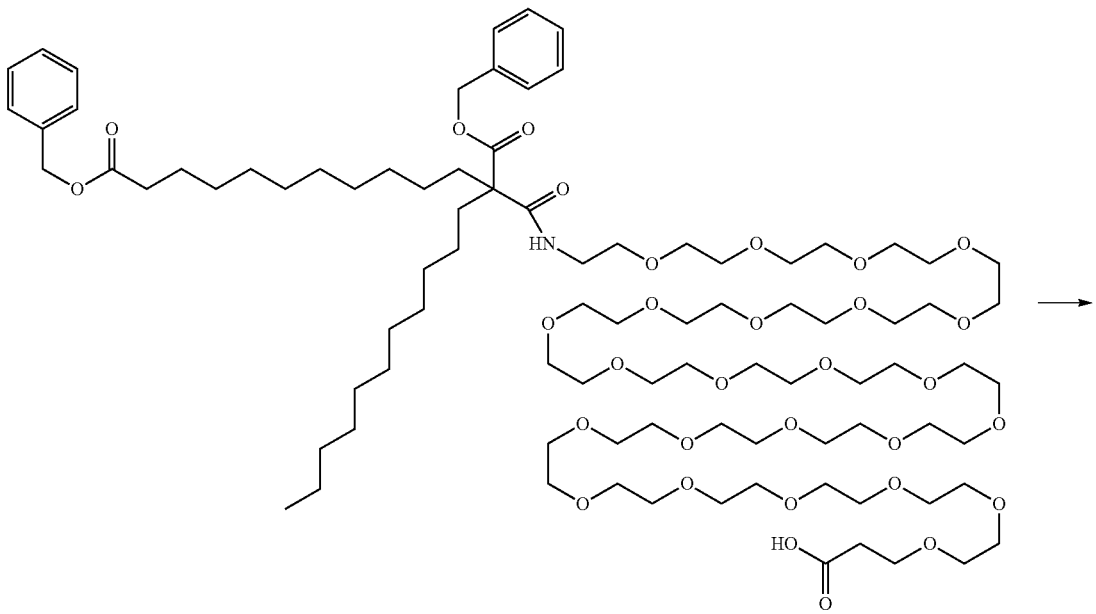

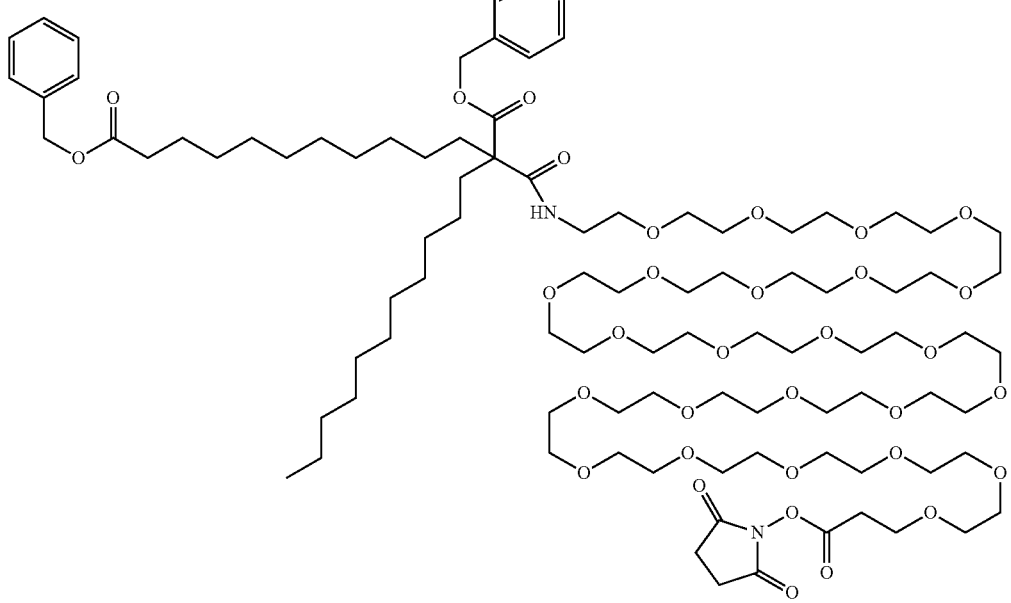

DCC (22 mg, 0.103 mmol) in DCM (0.265 mL) was added to a solution of intermediate 35 (150 mg, 0.086 mmol) and N-hydroxysuccinimide in DCM (1.5 mL). The reaction was stirred for 1.5 hrs. Additional N-hydroxysuccinimide (10 mg) in THF (0.5 mL) and DCC (22 mg) in DCM (0.265 mL) was added and the reaction stirred overnight. The solvent was evaporated and the residue purified by flash column (silica 12, 0-5% MeOH/DCM) to yield intermediate 36 (159 mg, quantitative) as a white solid: LCMS Method G Rt=1.55 min, $[M+H_3O+H]^{+2}$ 933.9.

Step 10

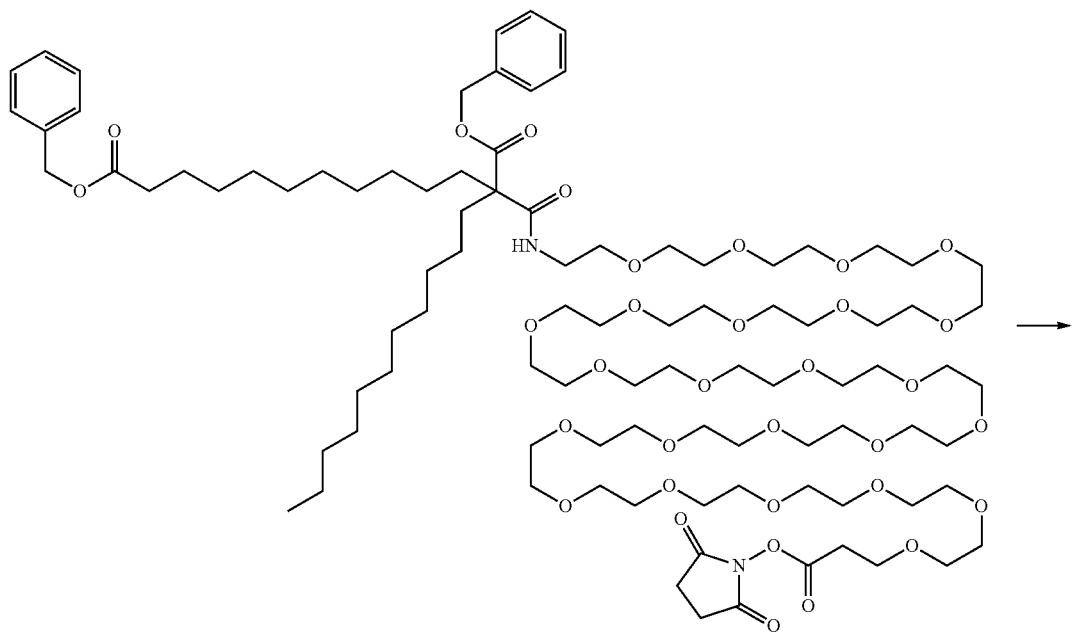

-continued

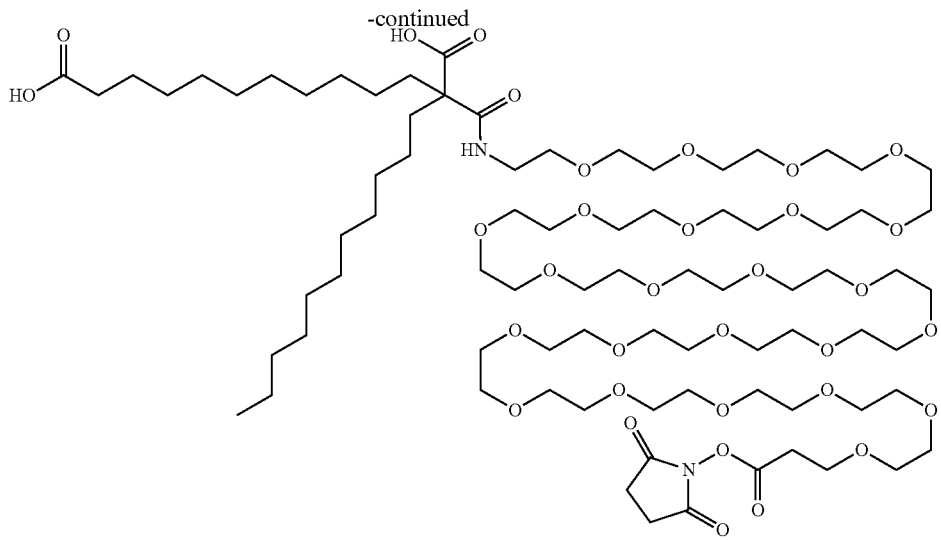

To a solution of compound from step 9 (159 mg, 0.086 mmol) in THF (5 mL) was added a suspension of 10% Pd on carbon (4.6 mg, 4.3 mol) in THF (1 mL). The reaction was placed under hydrogen and stirred for 40 min. More Pd on carbon (7 mg, 6.5 µmol) was added and the stirred another 1 hr under hydrogen. The reaction was passed through a membrane filter and the filtrate evaporated. The residue was purified by HPLC (Sunfire C18 30×50 mm, 45-70% ACN/water+ 0.1% TFA) to yield the title compound (83 mg, 0.047 mmol, 54%): LCMS Method G Rt=1.03 min, [M+2H]+2 835.2; $^1$H NMR (400 MHz, CHLOROFORM-d) ppm 0.84-0.94 (m, 3H) 1.17 (br. s., 2H) 1.21-1.39 (m, 30H) 1.57-1.68 (m, 2H) 1.69-1.80 (m, 2H) 1.97-2.10 (m, 2H) 2.34 (t, J=7.21 Hz, 2H) 2.86 (s, 4H) 2.92 (t, J=6.48 Hz, 2H) 3.51-3.73 (m, 96H) 3.87 (t, J=6.48 Hz, 2H) 7.45 (t, J=4.46 Hz, 1H)

Step 4: Preparation of Conjugate Comprising Apelin Construct A-H-Q-R-P-C-L-S-C-K-G-P-DNle-Phenethyl Amine (SEQ ID NO: 65) and Fatty Acid-PEG Construct (N-Terminus Conjugation)—Example 41

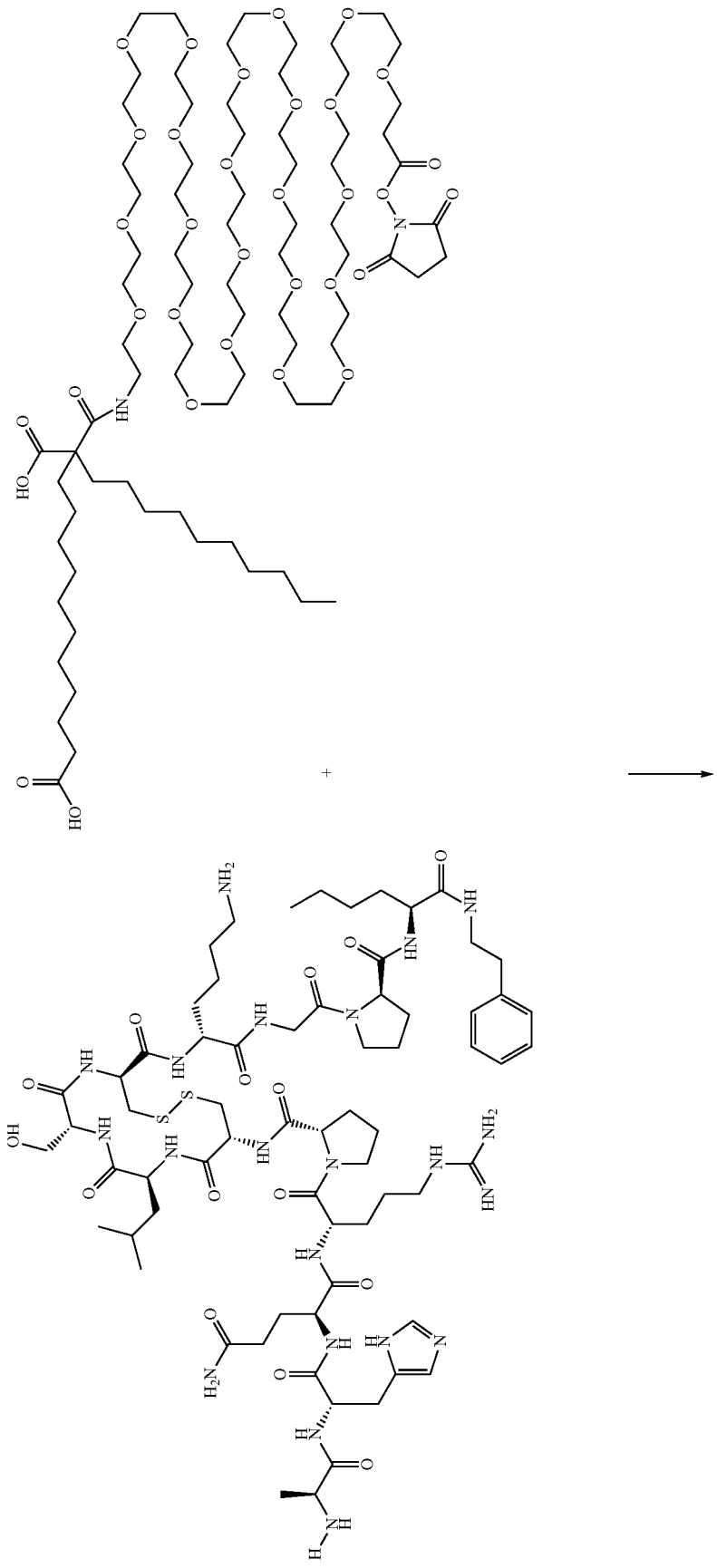

-continued
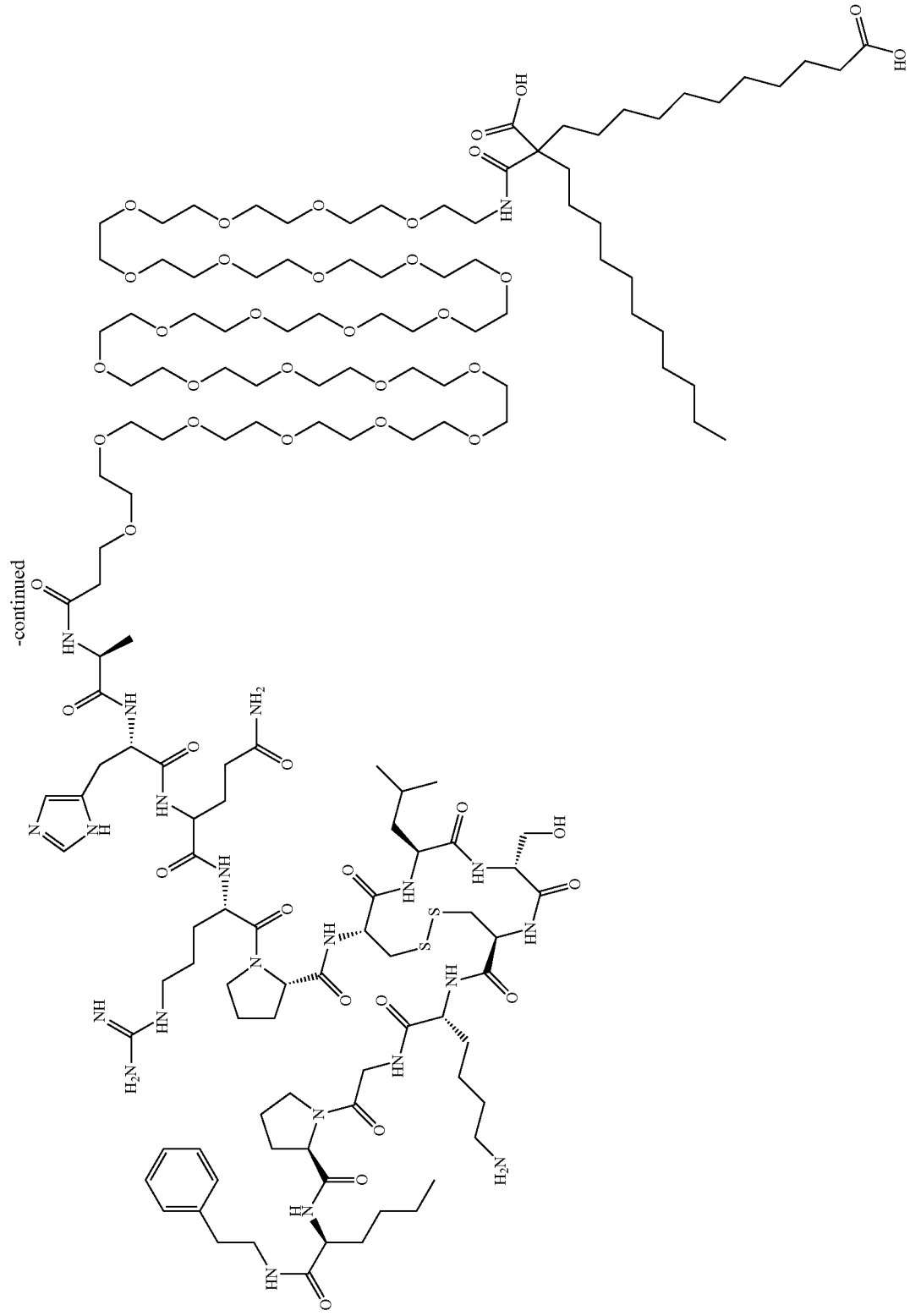

A 10 mg/mL solution of NHS-fatty acid (product A from step 7 of Example 40) was prepared in H₂O. Intermediate 41c (1.5 mg, 0.993 μmol) was dissolved in 30 mM pH4 NaOAc buffer (672 μL) and NHS-fatty acid (0.850 mL, 5.10 μmol) was added. The reaction was mixed at r.t. for 16 hours at which point an additional 1.5 mg of NHS-fatty acid (10 mg/mL in H₂O) was added and the reaction mixed at r.t. for 16 hours. 8 mg of NHS-fatty acid (10 mg/mL in H₂O) was added and the reaction mixed at r.t. for 3 days and 1.7 mg of NHS-fatty acid (10 mg/mL in H₂O) was added. The mixture was shaken at r.t. for 16 hours and purified via M-triggered HPLC to give 1.7 mg of the title compound as a white powder (0.510 μmol, 51%). LCMS (SQ2 ProductAnalysis-Acidic-Peptide-Polar, Acquity UPLC BEH C18 column, 130 Å, 1.7 μm, 2.1 mm×50 mm, 50° C.): $R_t$=3.87 minutes, MS [M+H+2/2] 1533.1; [M+H+3/3] 1022.9.

Example 42

Conjugation of AH-Fc with Apelin Cyclic Peptide

General Scheme

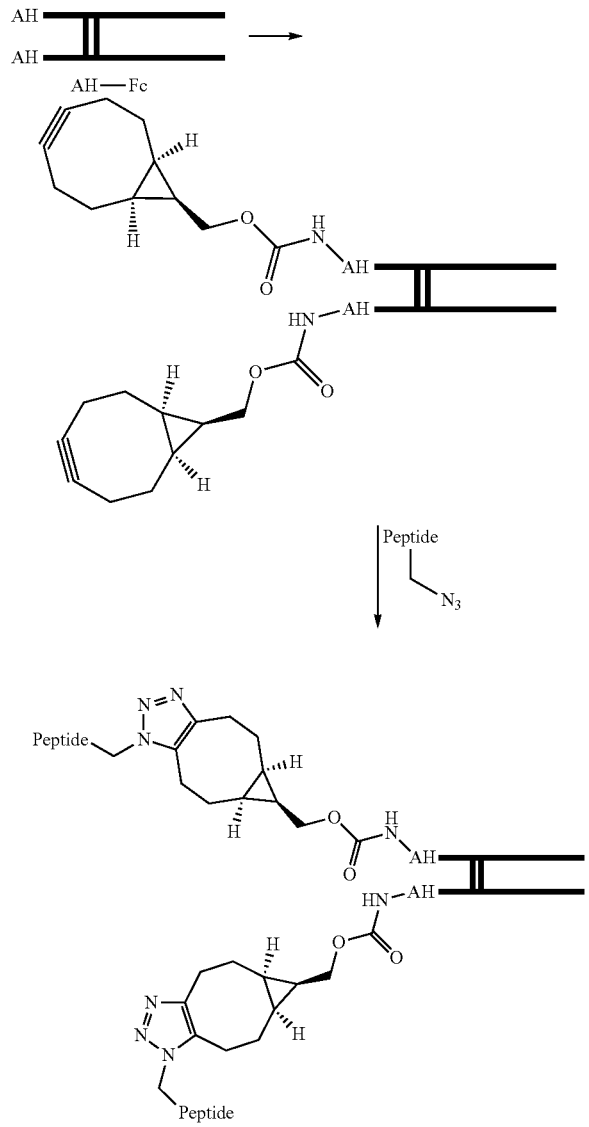

Step 1: Preparation of AH-Fc Construct

Construct Cloning:

A DNA fragment containing the mouse Ig kappa chain signal peptide followed by a human Fc and a short bis-amino acid sequence (AH) was codon optimized by gene synthesis (GeneArt) with 5'-NheI and 3'-EcoRI restriction sites. The resulting sequence was restriction digested with both NheI and EcoRI and ligated into NheI and EcoRI sites of vector pPL1146, downstream of a CMV promoter. The ligation was transformed into *E. coli* DH5α cells and colonies containing the correct insert were identified by DNA sequencing. Sequence shown is for the sense strand and runs in the 5' and 3' direction.

AH-Fc (SEQ ID NO: 66)
GCTAGCCACCATGGAAACTGACACCCTGCTGCTGTGGGTCCTGCTGCTGTG

GGTGCCTGGCAGCACTGGCGCTCATGATAAGACACACACATGCCCCCCTTG

TCCAGCACCAGAGGCAGCTGGAGGACCAAGCGTGTTCCTGTTTCCACCCAA

GCCTAAAGACACACTGATGATCTCAAGGACCCCAGAAGTCACATGCGTGGT

CGTGGACGTGTCTCACGAGGACCCCGAAGTCAAGTTCAACTGGTACGTGGA

TGGCGTCGAGGTGCATAATGCTAAGACCAAACCCCGAGAGGAACAGTACAA

CAGCACCTATCGGGTCGTGTCCGTCCTGACAGTGCTGCACCAGGATTGGCT

GAACGGCAAAGAGTATAAGTGCAAAGTGAGTAATAAGGCTCTGCCTGCACC

AATCGAGAAAACAATTTCTAAGGCTAAAGGGCAGCCAAGAGAACCCCAGGT

GTACACTCTGCCTCCATCTAGGGAGGAAATGACAAAGAACCAGGTCAGTCT

GACTTGTCTGGTGAAAGGCTTCTACCCCTCCGACATCGCAGTGGAGTGGGA

ATCTAATGGCCAGCCTGAAAACAATTACAAGACCACACCCCCTGTGCTGGA

CTCCGATGGGTCTTTCTTTCTGTATTCTAAGCTGACCGTGGATAAAAGTCG

GTGGCAGCAGGGAAACGTCTTCTCATGCAGCGTGATGCACGAGGCCCTGCA

CAATCATTACACACAGAAGTCCCTGTCTCTGAGTCCAGGCAAATGAGAATT

C

Sequence of the AH-Fc Construct:

```
                                                     (SEQ ID NO: 67)
  1   METDTLLLWV LLLWVPGSTG AHDKTHTCPP CPAPEAAGGP SVFLFPPKPK

51   DTLMISRTPE VTCVVVDVSH EDPEVKFNWY VDGVEVHNAK TKPREEQYNS

101   TYRVVSVLTV LHQDWLNGKE YKCKVSNKAL PAPIEKTISK AKGQPREPQV

151   YTLPPSREEM TKNQVSLTCL VKGFYPSDIA VEWESNGQPE NNYKTTPPVL

201   DSDGSFFLYS KLTVDKSRWQ QGNVFSCSVM HEALHNHYTQ KSLSLSPGK_
```

AH-Fc Protein Expression and Purification:

AH-Fc expression plasmid DNA was transfected into HEK293T cells at a density of 1×10⁶ cells per ml using standard polyethylenimine methods. 500 ml cultures were then grown in FreeStyle 293 Medium (Life Technologies) in 3 L flasks for 4 days at 37° C. AH-Fc protein was purified from clarified conditioned media. Briefly 500 ml of conditioned media was flowed over a 5 ml HiTrap MabSelect SuRe column (GE Life Sciences) at 4 ml/min. The column was washed with 20 column volumes of PBS containing 0.1% Triton X-114 and then the AH-Fc protein was eluted with 0.1 M glycine, pH 2.7, neutralized with 1 M Tris-HCl, pH 9 and dialyzed against PBS. Protein yields were 10 to 20 mg per 500 ml conditioned media and endotoxin levels were <1 EU/mg as measured by the Charles River ENDOSAFE PTS test.

Quality Control of AH-Fc Proteins:
LC/MS of AH-Fc Proteins:
Peaks were heterogeneous and about 3 kDa larger than expected for dimers. This is characteristic of N-linked glycosylation expected for Fc which has a consensus N-linked glycosylation site.
LC/MS of Reduced, N-Deglycosylated AH-Fc Proteins:
gave sharp peaks. The molecular weight for AH-Fc was as expected. The cysteines at the C-terminus appear to protect the protein from cleavage.
Analytical Size Exclusion on Superdex 200:
Fc-Apelin proteins have between 89 and 100% dimer, 0 to 10% tetramer, and 0 to 1% aggregate.
Reducing SDS/PAGE:
All proteins migrated as predominately monomers of the expected size.
Step 2: Synthesis of NH₂-AzidoLys-GGGGS-Q-R-P-C-L-S-C-K-G-P-Dnle-Phenethylamine (SEQ ID NO: 68)

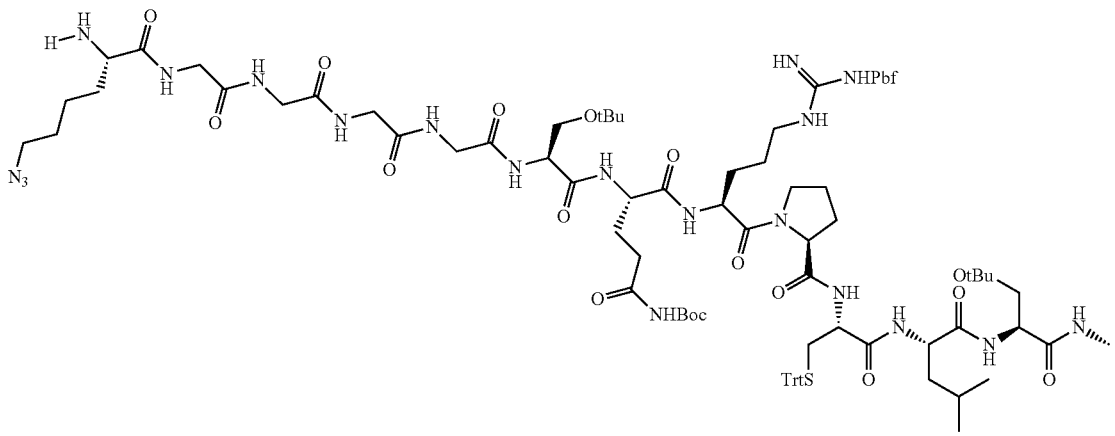

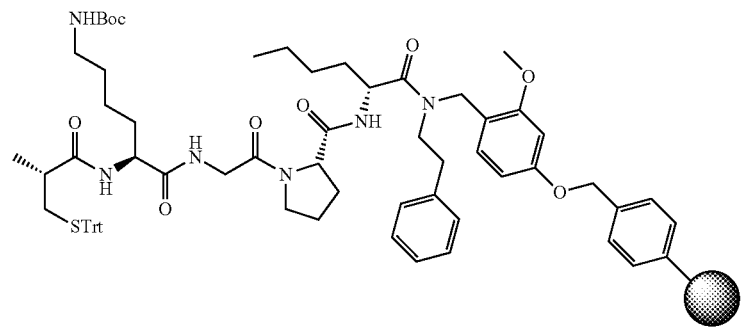

Phenethylamine-AMEBA resin (Sigma Aldrich, 0.25 mmol, 1.0 mmol/g) was subjected to solid phase peptide synthesis on an automatic peptide synthesizer (CEM Liberty Blue Microwave) with standard double Arg for the Arg residues and D-Nle and Azidolysine coupled double time. Amino acids were prepared as 0.2 M solution in DMF. A standard coupling cycle was defined as follows:

Amino acid coupling: AA (5 eq.), HATU (5 eq.), DIEA (25 eq.)
Washing: DMF (3×7 mL)
Fmoc Deprotection: 20% Piperidine/0.1 M HOBt (2×7 mL)
Washing: DMF (4×7 mL then 1×5 mL)

| Coupling | AA | Number of couplings × Reaction time (Temp) | Coupling Method |
|---|---|---|---|
| 1 | Fmoc-D-Nle-OH | 1 × 10 min (70° C.) | DIEA/HATU |
| 2 | Fmoc-L-Pro-OH | 1 × 5 min (70° C.) | DIEA/HATU |
| 3 | Fmoc-L-Gly-OH | 1 × 5 min (70° C.) | DIEA/HATU |
| 4 | Fmoc-L-Lys-OH | 1 × 5 min (70° C.) | DIEA/HATU |
| 5 | Fmoc-L-Cys-OH | 1 × 5 min (70° C.) | DIEA/HATU |
| 6 | Fmoc-L-Ser-OH | 1 × 5 min (70° C.) | DIEA/HATU |
| 7 | Fmoc-L-Leu-OH | 1 × 5 min (70° C.) | DIEA/HATU |
| 8 | Fmoc-L-Cys-OH | 1 × 5 min (70° C.) | DIEA/HATU |
| 9 | Fmoc-L-Pro-OH | 1 × 5 min (70° C.) | DIEA/HATU |
| 10 | Fmoc-L-Arg-OH | 2 × 25 min (25° C.) | DIEA/HATU |
| 11 | Fmoc-L-Gln-OH | 1 × 5 min (70° C.) | DIEA/HATU |
| 12 | Fmoc-L-Ser-OH | 1 × 5 min (70° C.) | DIEA/HATU |
| 13 | Fmoc-L-Gly-OH | 1 × 5 min (70° C.) | DIEA/HATU |
| 14 | Fmoc-L-Gly-Gly-Gly-OH | 1 × 10 min (70° C.) | DIEA/HATU |
| 15 | Fmoc-L-AzidoLys-OH | 1 × 10 min (70° C.) | DIEA/HATU |

After the assembly of the peptide, the resin was washed with DMF (2×50 mL) and DCM (2×50 mL) then dried under vacuum to give Intermediate 42a (770 mg, 0.250 mmol).

Step 3: Preparation of Intermediate 42b (Cleavage of Peptide from Resin)

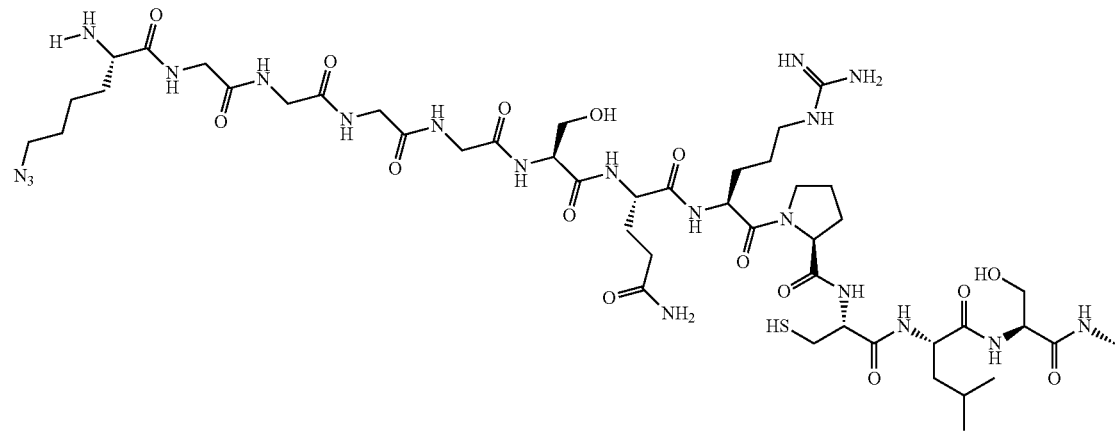

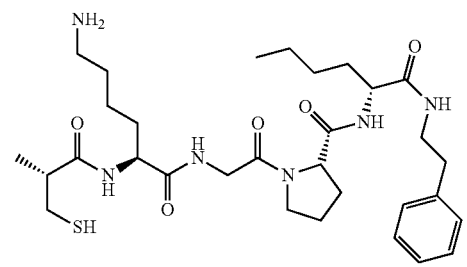

Intermediate 42a (770 mg, 0.250 mmol) was divided in half and each sample was combined with 6 mL TFA solution (37 mL TFA, 1 mL H$_2$O, 1 mL TIPS, 2.569 g (20 eq.) DTT) and shaken at r.t. for 3 hours. The solution was removed from the resin and precipitated into 40 mL cold Et$_2$O. The solution was vortexed and let stand over ice for 10 minutes before centrifuging at 4000 rpm for 5 minutes. The solvent was removed and the white solid was washed twice more with cold Et$_2$O (40 mL each time), centrifuged (5 minutes each time) and decanted. The solid was dried under vacuum overnight and purified via M-triggered HPLC yielding Intermediate 43b as a white powder (80 mg, 0.045 mmol, 80%). LCMS (SQ2 ProductAnalysis-Acidic-Peptide-Polar, Acquity UPLC BEH C18 column, 130 Å, 1.7 µm, 2.1 mm×50 mm, 50° C.): R$_t$=2.32 minutes, MS [M+H+2/2] 888.0.

Step 4: Preparation of Intermediate 42c (Cyclization of Cysteine Residues)

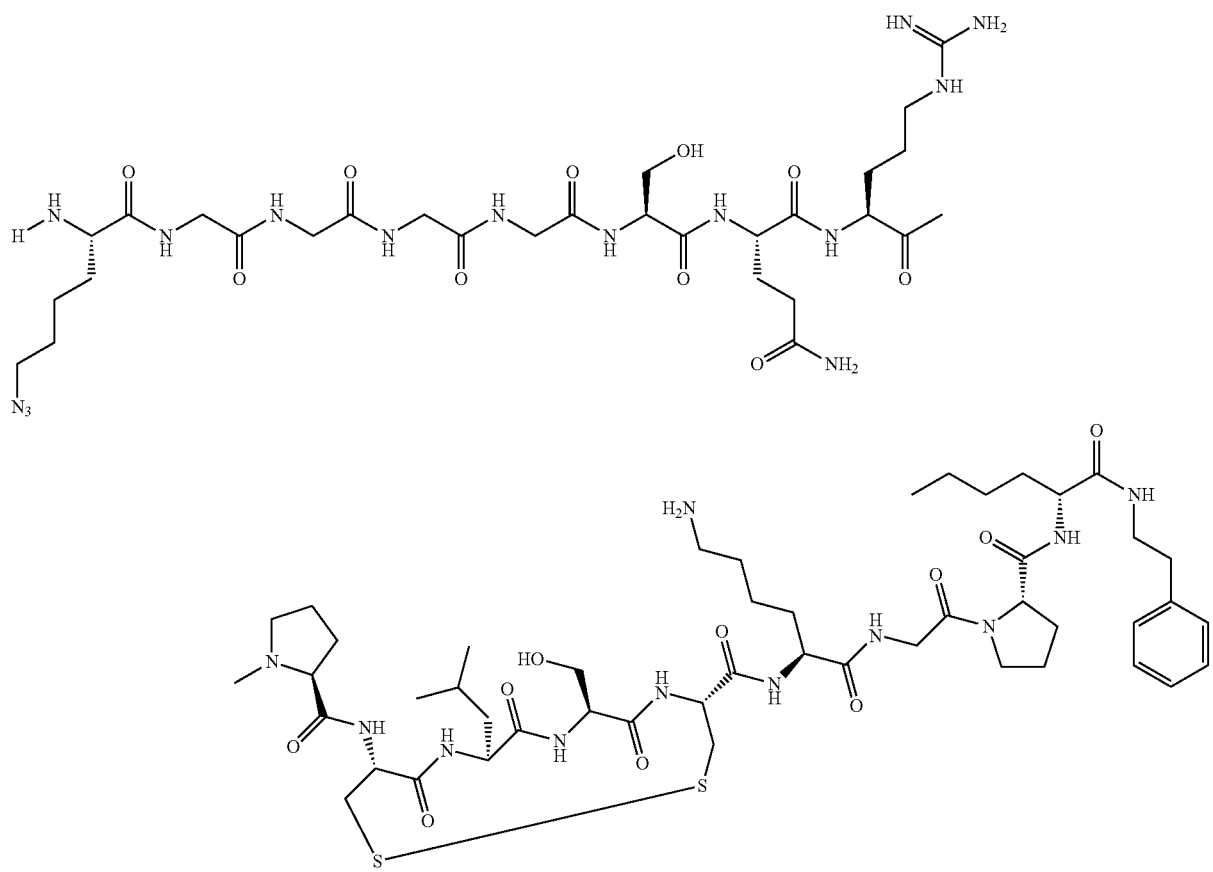

Intermediate 42b (80 mg, 0.045 mmol) was dissolved in water (1.25 mL) and iodine (50 mM in HOAc, 1.804 mL, 0.090 mmol) was added slowly dropwise and the reaction was mixed at r.t. for 3 hours. LCMS analysis of the crude reaction showed complete conversion of starting material. 0.5 M ascorbic acid was added dropwise until color dissipated. The material was purified via MS-triggered HPLC. Lyophilization of the pooled fractions gave 20.1 mg of the desired product as a white powder (0.045 mmol, 25%). LCMS (SQ2 ProductAnalysis-Acidic-Peptide-Polar, Acquity UPLC BEH C18 column, 130 Å, 1.7 µm, 2.1 mm×50 mm, 50° C.): R=2.17 minutes, MS [M+H+2/2] 886.8.

Step 5: Preparation of Fc-AH BCN (Installation of Click Handle on AH-Fc N-Terminus)

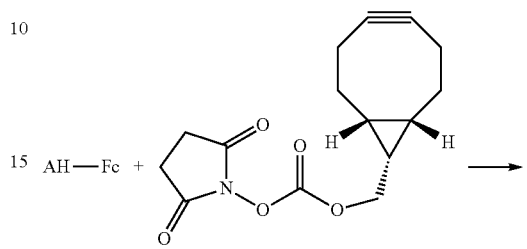

-continued

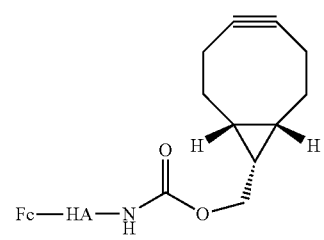

Fc-AH (from step 1: 1 mL, 3 mg/mL, 0.117 μmol) was dissolved in 30 mM NaOAc pH 4.0 (4.3 mL) and a 10 mg/mL stock solution of (1R,8S,9s)-bicyclo[6.1.0]non-4-yn-9-ylmethyl(2,5-dioxopyrrolidin-1-yl) carbonate (BCN) in DMSO (0.70 mL) was slowly added and the reaction placed on a shaker plate at r.t. for 3 days. BCN (0.25 mL) was added and the reaction was mixed at r.t. for 3 days. BCN (0.70 mL) was added and the reaction was mixed at r.t. for 16 hours. The solution was exchanged into 30 mM NaOAc pH 4.0 using 10 kDa MWCO Amicon centrifugal filter by diluting and concentrating the reaction 5 times to a volume of 900 μL. The solution was centrifuged and supernatant removed. The concentration was measured by A280 to be 1.73 mg/mL (1.56 mg, 26%). LCMS (QT2, Protein_20-70 kDa_3 min, Proswift Monolith 4.6×50 mm, 50° C., Eluent A: Water+0.1% Formic Acid, Eluent B: CAN+0.1% Formic Acid, 2-98% over 2 min) $R_t$=1.58 min.

| Degree of Labelling | Calculated | Observed | % TIC (MS+) Intensity |
|---|---|---|---|
| AH-Fc | 51141 | 51141.5 | 18 |
| AH-Fc + 1BCN | 51318 | 51317 | 31 |
| AH-Fc + 2BCN | 51495 | 51496 | 31 |
| AH-Fc + 3BCN | 51672 | 51671 | 20 |

Step 6: Preparation of Example 42: Fc-HA-BCN Conjugated to Intermediate 43c

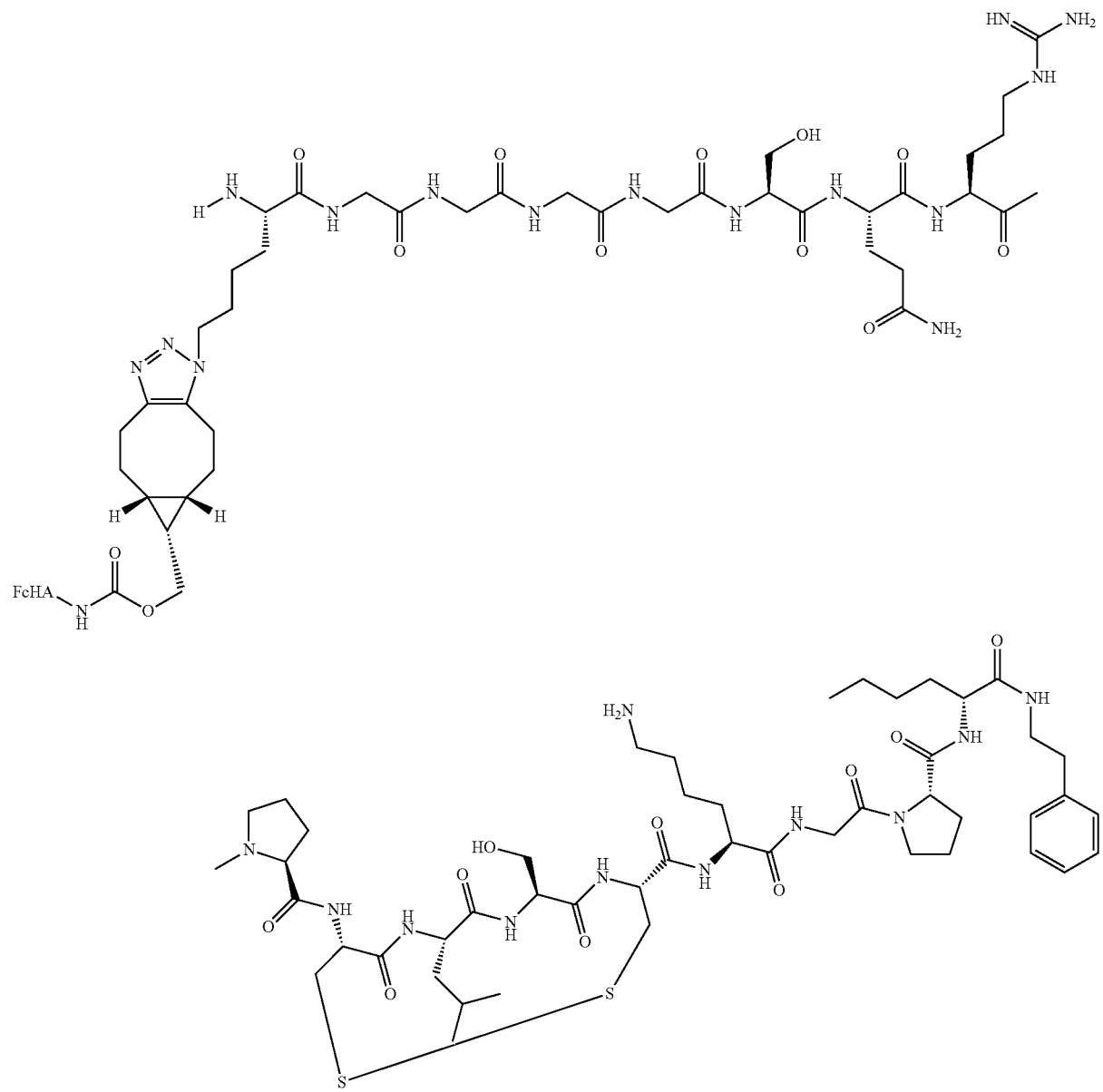

A 50 mg/mL stock solution of intermediate 42c in $H_2O$ was prepared. Intermediate 43c (53.7 μL, 1.515 μmol) was added to a stock solution of Fc-HA-BCN (from step 5) in 30 mM NaOAc pH 4.0 (1.73 mg/mL, 1.56 mg, 0.030 μmol) and the reaction was mixed at r.t. for 16 hours. The solution was exchanged into 30 mM NaOAc pH 4.0 using 50 kDa MWCO Amicon centrifugal filter by diluting and concentrating the reaction 5 times to a volume of 250 μL. The concentration was measured by A280 to be 3.32 mg/mL (830 μg, 50%). LCMS (QT2, Protein_35-70 kDa_3 min, Proswift Monolith 4.6×50 mm, 50° C., Eluent A: Water+0.1% Formic Acid, Eluent B: CAN+0.1% Formic Acid, 10-80% B over 2 min) $R_f$=1.43 min, MS [M(glycosylated)+H] 54524.5.

Example 43

Fc-Apelin Conjugate Using Sortase (SEQ ID NOS 69, 69, 70, 71, and 71, Respectively, in Order of Appearance)

Step 1: Preparation of Fc-Sortase Construct

Construct Cloning:

A DNA fragment containing the mouse Ig kappa chain signal peptide followed by a human Fc and a sortase recognition sequence (LPXTG) (SEQ ID NO: 72) was codon optimized by gene synthesis (GeneArt) with 5'-NheI and 3'-EcoRI restriction sites. The resulting sequence was restriction digested with both NheI and EcoRI and ligated into NheI and EcoRI sites of vector pPL1146, downstream of a CMV promoter. The ligation was transformed into E coli DH5☐ cells and colonies containing the correct insert were identified by DNA sequencing. Sequence shown is for the sense strand and runs in the 5' and 3' direction.

```
Fc-sortase
                                                           (SEQ ID NO: 73)
GCTAGCCACCATGGAAACCGACACCCTGCTGCTGTGGGTGCTGCTGCTGTGGGTGCCAGGCAG

CACCGGCGATAAGACCCACACCTGTCCTCCCTGTCCTGCCCCTGAAGCTGCTGGCGGCCCTAG

CGTGTTCCTGTTCCCCCCAAAGCCCAAGGACACCCTGATGATCAGCCGGACCCCCGAAGTGAC

CTGCGTGGTGGTGGATGTGTCCCACGAGGACCCTGAAGTGAAGTTCAATTGGTACGTGGACGG

CGTGGAAGTGCACAACGCCAAGACCAAGCCCAGAGAGGAACAGTACAACAGCACCTACCGGGT

GGTGTCCGTGCTGACCGTGCTGCACCAGGACTGGCTGAACGGCAAAGAGTACAAGTGCAAGGT

GTCCAACAAGGCCCTGCCAGCCCCCATCGAGAAAACCATCAGCAAGGCCAAGGGCCAGCCCCG

CGAACCCCAGGTGTACACACTGCCCCCTAGCCGGGAAGAGATGACCAAGAACCAGGTGTCCCT

GACCTGTCTCGTGAAGGGCTTCTACCCCTCCGATATCGCCGTGGAATGGGAGAGCAACGGCCA

GCCCGAGAACAACTACAAGACCACCCCCCCTGTGCTGGACAGCGACGGCTCATTCTTCCTGTA

CAGCAAGCTGACAGTGGACAAGAGCCGGTGGCAGCAGGGCAACGTGTTCAGCTGCAGCGTGAT

GCACGAGGCCCTGCACAACCACTACACCCAGAAGTCCCTGAGCCTGAGCCCTGGAAAAGGCGG

CGGAGGCTCTCTGCCTGAAACAGGCGGACTGGAAGTGCTGTTCCAGGGCCCCTAAGAATTC
```

```
                                                           (SEQ ID NO: 74)
  1  METDTLLLWV LLLWVPGSTG DKTHTCPPCP APEAAGGPSV FLFPPKPKDT

51  LMISRTPEVT CVVVDVSHED PEVKFNWYVD GVEVHNAKTK PREEQYNSTY

101  RVVSVLTVLH QDWLNGKEYK CKVSNKALPA PIEKTISKAK GQPREPQVYT
```

```
151  LPPSREEMTK NQVSLTCLVK GFYPSDIAVE WESNGQPENN YKTTPPVLDS

201  DGSFFLYSKL TVDKSRWQQG NVFSCSVMHE ALHNHYTQKS LSLSPGKGGG

251  GSLPETGGLEVLFQGP
```

Protein Expression and Purification:

Fc-sortase expression plasmid DNA was transfected into HEK293T cells at a density of 1×10⁶ cells per ml using standard polyethylenimine methods. 500 ml cultures were then grown in FreeStyle 293 Medium (Life Technologies) in 3 L flasks for 4 days at 37° C.

Fc-sortase protein was purified from clarified conditioned media. Briefly, 500 ml of conditioned media was flowed over a 5 ml HiTrap MabSelect SuRe column (GE Life Sciences) at 4 ml/min. The column was washed with 20 column volumes of PBS containing 0.1% Triton X-114 and then the Fc-sortase protein was eluted with 0.1M glycine, pH 2.7, neutralized with 1 M Tris-HCl, pH 9 and dialyzed against PBS. Protein yields were 10 to 20 mg per 500 ml conditioned media and endotoxin levels were <1 EU/mg as measured by the Charles River ENDOSAFE PTS test.

Quality Control of Fc-Sortase Protein
LC/MS of Native Fc-Sortase Protein:

Peak was heterogeneous and about 3 kDa larger than expected for dimers. This is characteristic of N-linked glycosylation expected for Fc which has a consensus N-linked glycosylation site.

LC/MS of Reduced, N-Deglycosylated Fc-Sortase Protein:

Peak was sharp. The molecular weight was 2 daltons less than theoretical, likely due to Cysteine ×2 reduction.

Analytical Size Exclusion on Superdex 200:

Fc-sortase protein had between 89 and 100% dimer, 0 to 10% tetramer, and 0 to 1% aggregate.

Reducing SDS/PAGE:

The protein migrated predominately as a monomer of the expected size.

Step 2: Preparation of Apelin Peptide (H₂N-GGGGGQRPC*LSC*KGP(D-Nle)Phenethylamine) (SEQ ID NO: 70) for Sortase Conjugation (SEQ ID NOS 75, 70, and 70, respectively, in order of appearance)

Step 2a: Preparation of Intermediate 43a

Phenethylamine-AMEBA resin (Sigma Aldrih, 0.25 g, 0.25 mmol, 1.0 mmol/g) was subjected to solid phase peptide synthesis on an automatic peptide synthesizer (CEM LIBERTY) with standard double Arg for the Arg residues. Amino acids were prepared as 0.2 M solutions in DMF.

A coupling cycle was defined as follows:

Amino acid coupling: AA (4.0 eq.), HATU (4.0 eq.), DIEA (25 eq.)

Washing: DMF (3×10 mL, 1 min each time).

Fmoc deprotection: Piperidine/DMF (1:4) (10 mL, 75° C. for 1 min, then 10 mL, 75° C. for 3 min).

Washing: DMF (4×10 mL, 1 min each time).

| Coupling | AA | Number of couplings × Reaction time | Reaction Temperature |
|---|---|---|---|
| 1 | Fmoc-D-Nle-OH | 1 × 5 min | 75° C. |
| 2 | Fmoc-L-Pro-OH | 1 × 5 min | 75° C. |
| 3 | Fmoc-Gly-OH | 1 × 5 min | 75° C. |
| 4 | Fmoc-L-Lys(Boc)-OH | 1 × 5 min | 75° C. |
| 5 | Fmoc-L-Cys(Trt)-OH | 1 × 6 min | 2 min at 25° C. 4 min at 50° C. |
| 6 | Fmoc-L-Ser(tBu)-OH | 1 × 5 min | 75° C. |
| 7 | Fmoc-L-Leu-OH | 1 × 5 min | 75° C. |
| 8 | Fmoc-L-Cys(Trt)-OH | 1 × 6 min | 2 min at 25° C. 4 min at 50° C. |
| 9 | Fmoc-L-Pro-OH | 1 × 5 min | 75 |
| 10 | Fmoc-L-Arg(Pbf)-OH | 2 × 30 min | 25 min at 25° C. 5 min at 75° C. |

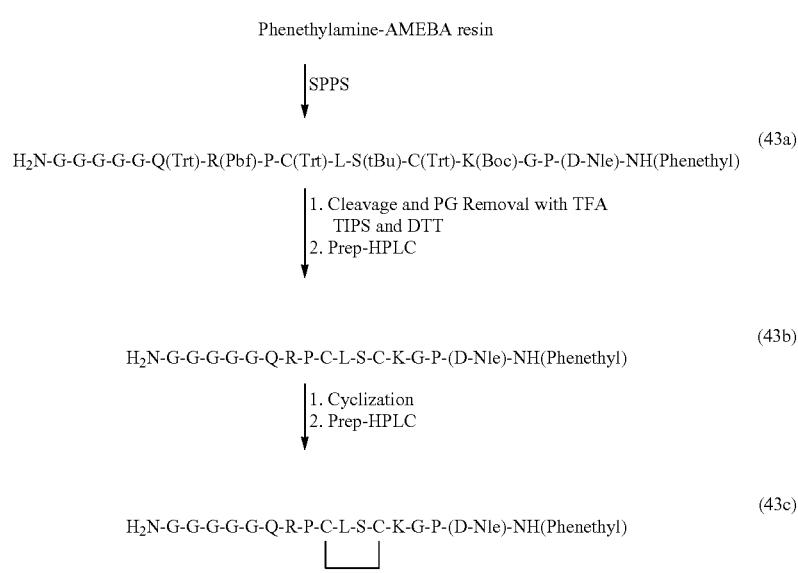

-continued

| Coupling | AA | Number of couplings × Reaction time | Reaction Temperature |
|---|---|---|---|
| 11 | Fmoc-L-Gln(Trt)-OH | 1 × 5 min | 75° C. |
| 12 | Fmoc-Gly-Gly-Gly-OH | 1 × 5 min | 75° C. |
| 13 | Fmoc-Gly-OH | 1 × 5 min | 75° C. |
| 14 | Fmoc-Gly-OH | 1 × 5 min | 75° C. |

After the assembly of the peptide, the resin was washed with DMF (3×10 mL), DCM (3×10 mL). The peptide resin was dried under vacuum at room temperature to give Intermediate 43a (0.622 g, 0.25 mmol).

Step 2b: Preparation of Intermediate 42b, H₂N-G-G-G-G-G-Q-R-P-C-L-S-C-K-G-P-D-Nle)-NH(Phenethyl) (SEQ ID NO: 70)

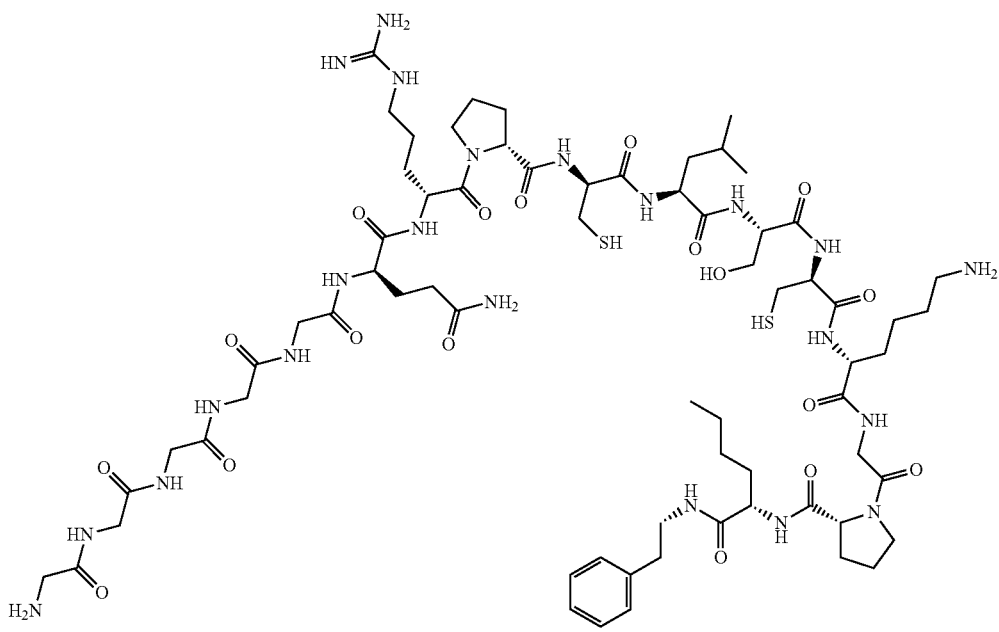

1) Cleavage and Protecting Group Removal

To intermediate 43a (0.622 g, 0.25 mmol) was added 3 mL solution of 95% TFA/2.5% H₂O/2.5% TIPS and DTT (771 mg, 5.00 mmol), the resulting mixture was shaked at room temperature for 3 hours, then filtered. The filtrate was dropped into 40 mL of cold ether, then centrifuged at 4000 rpm for 5 minutes. The solvent was removed and the white solid was washed with ether (3×40 mL), vortexed and centrifuged. The solid was dried under high vacuum at 25° C. for 1 hour.

2) Purification

The above white solid was then purified by preparative HPLC (Sunfire™ Prep C18 OBD™ 30×50 mm 5 um column ACN/H₂O w/ 0.1% TFA 75 ml/min, 10-30% ACN 8 min gradient). The product fraction was lyophilized to give intermediate 43b as TFA salt (44 mg, 11%).

Step 3: Preparation of H₂N-G-G-G-G-G-Q-R-P-C*-L-S-C*-K-G-P-(D-Nle)-NH(Phenethyl) (Disulfide $C^9$-$C^{12}$) (SEQ ID NO: 70), Intermediate 43c

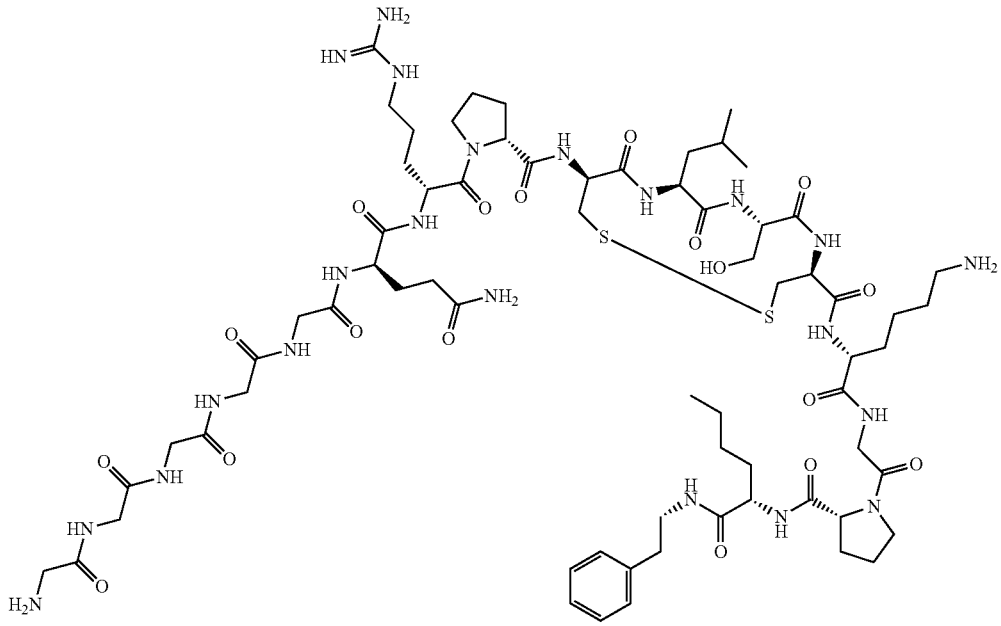

To intermediate 43b (44 mg, 0.028 mmol) in 0.9 mL of H₂O was added I₂ (50 mM in AcOH, 1.1 mL 0.055 mmol) dropwise. The mixture was shaked at room temperature overnight. LC/MS showed the reaction completed. To the reaction mixture was added several drops of 0.5 M of ascorbic acid solution (MeOH/H₂O=1/1) until the color of the solution disappeared. The mixture was diluted with MeOH for HPLC purification. The purification was carried out by preparative HPLC (Sunfire™ Prep C18 OBD™ 30×50 mm 5 um column ACN/H2O w/ 0.1% TFA 75 ml/min, 10-30% ACN 8 min gradient). The product fraction was lyophilized to give H₂N-G-G-G-G-G-Q-R-P-C*-L-S-C*-K-G-P-(D-Nle)-NH(Phenethyl) (disulfide $C^9$-$C^{12}$) (SEQ ID NO: 70), intermediate 43c as TFA salt (13 mg, 30%). LC/MS (QT2, ProductAnalysis-HRMS-Acidic, Waters Acquity UPLC BEH C18 1.7 um 2.1× 50 mm, 50° C., Eluent A: Water+0.1% Formic Acid, Eluent B: Acetonitrile+0.1% Formic Acid, gradient 2% to 98% B/A over 5.15 mins): Retention time: 0.98 mins; MS [M+2]²⁺: observed: 1587.7993, calculated: 1587.868.

Step 3: Sortase Conjugation of Fc-Sortase and Intermediate 43c

1) Chemoenzymatic Sortase Conjugation
On ice bath, to the Fc-Sortase (698 µl, 0.040 µmol, 3.15 mg/mL) in PBS (pH7.4) buffer solution was added the solution of H₂N-G-G-G-G-G-Q-R-P-C*-L-S-C*-K-G-P-(D-Nle)-NH(Phenethyl) (disulfide $C^9$-$C^{12}$) (SEQ ID NO: 70) (64.1 µL, 2.018 µmoL, 50 mg/mL) in Tris-8.0 buffer, followed by 520 µM of sortase A (78 µL, 0.040 µmoL) in 50 mM Tris-Cl pH7.4, 150 mM NaCl. The mixture was shaked at room temperature overnight. LC/MS showed the reaction completed.

2) Purification and Desalting
The above solution was flowed over a 5 mL HiTrap Mab Select SuRe column (GE Lifesciences #11-0034-95) at 4 mL/min on ATTA XPRESS. Example 43 was washed on the column with 20 column volumes (CV) PBS+0.1% Triton 114 and eluted with 0.1M glycine, pH 2.7, neutralized with 1 M tris-HCl, pH 9 and dialyzed versus PBS. The purified solution was desalted by using Zeba Sping Desalting Column, 5 mL (89891) to give 1.5 mL target solution, the average concentration was 0.598 mg/mL, and the recoverage was 90%. LCMS (QT2, Protein_20-70 kDa_3 min, AcQuity ProSwift RP-3U 4.6×50 mm, 1.0 mL/min, Eluent A: Water+0.1% Formic Acid, Eluent B: Acetonitrile+0.1% Formic Acid, gradient 2% to 98% B/A over 3 mins): $R_f$=1.55 minutes, MS [M+H] 58845.0000.

Sequence of the Example 43:

(SEQ ID NO: 76)

```
  1  METDTLLLWV LLLWVPGSTG DKTHTCPPCP APEAAGGPSV FLFPPKPKDT

51  LMISRTPEVT CVVVDVSHED PEVKFNWYVD GVEVHNAKTK PREEQYNSTY

101  RVVSVLTVLH QDWLNGKEYK CKVSNKALPA PIEKTISKAK GQPREPQVYT
```

```
151 LPPSREEMTK NQVSLTCLVK GFYPSDIAVE WESNGQPENN YKTTPPVLDS

201 DGSFFLYSKL TVDKSRWQQG NVFSCSVMHE ALHNHYTQKS LSLSPGKGGG

251 GSLPETGGGGGQRPC*LSC*KGP(D-Nle)Phenethylamine
wherein LSLSPGKGGG GSLPETGGGGG (SEQ ID NO: 77) represents the
linker and QRPC*LSC*KGP(D-Nle)Phenethylamine (SEQ ID NO: 78)
the polypeptide.
```

The polypeptides in the examples below have been found to have $EC_{50}$ values in the range of about 0.01 nM to about 1100 nM for APJ receptor potency. The polypeptides in the examples below have been found to have a plasma stability higher than 2 minutes, higher than 5 minutes, higher than 10 minutes, higher than 20 minutes, higher than 50 minutes and higher than 60 minutes.

It can be seen that the polypeptides of the invention are useful as agonist of the APJ receptor and therefore useful in the treatment of diseases and conditions responsive to the activation of the APJ receptor, such as the diseases disclosed herein.

Furthermore, half-life of these peptides can be further extended by forming a bioconjugate comprising a peptide or polypeptide according to any one of Formula I to IV with a half-life extending moiety, such as Human serum Albumin or a Fc domain.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illustrated therein.

What is claimed is:

1. A cyclic polypeptide having the following formula I (SEQ ID NO: 1):

$$X1\text{-}R\text{-}X3\text{-}X4\text{-}L\text{-}S\text{-}X7\text{-}X8\text{-}X9\text{-}X10\text{-}X11\text{-}X12\text{-}X13 \quad\quad I$$

wherein:
X1 is the N-terminus of the polypeptide and is either absent, Q, A or pE;
X3 is P;
X4 is selected from C, c, hC and D-hC; wherein the side chain of C, c, hC or D-hC forms a disulfide bond with the side chain of X7;
X7 is C, c, hC or D-hC; and the side chain of X7 forms a disulfide bond with the side chain;
X8 is K or F;
X9 is G, A, a or absent;
X10 is P or absent;
X11 is D-Nle, Nle, M or f; and
X12 is absent or P, f, a, D-Nva or D-Abu;
X13 is the C-terminus and is absent or is selected from N-Methyl-L-phenylalanine F, f, a, y and Nal; wherein:
Nle is L-norleucine;
D-Nle is D-norleucine;
D-hC is D-homocysteine
hC is L-homocysteine;
Nal is L-naphathaline;
D-Nva is D-norvaline;
D-Abu is D-2-aminobutyric acid;
pE is L-pyroglutamic acid;
or an amide, an ester or a salt of the polypeptide.

2. The polypeptide according to claim 1 wherein X1 is pE; or an amide, an ester or a salt of the polypeptide.

3. The polypeptide according to claim 1 wherein X13 is F or f; or an amide, an ester or a salt of the polypeptide.

4. The polypeptide according to claim 1 wherein X13 is absent; or an amide, an ester or a salt of the polypeptide.

5. The polypeptide according to claim 4 wherein X12 is absent; or an amide, an ester or a salt of the polypeptide.

6. The polypeptide according to claim 5 wherein the C-terminus is an amide; or a salt of the polypeptide.

7. The polypeptide according to claim 6 wherein the C-terminus is an amide of Formula —C(O)—R2 and R2 is —NH$_2$, —NH-Me, —NH—NHBn, or —NH—(CH$_2$)$_2$-Ph; or a salt of the polypeptide.

8. The polypeptide according to claim 1 wherein X8 is K; or an amide, an ester or a salt of the polypeptide.

9. The polypeptide according to claim 1 wherein X9 is G; or an amide, an ester or a salt of the polypeptide.

10. The polypeptide according to claim 1 wherein X10 is P; or an amide, an ester or a salt of the polypeptide.

11. The polypeptide according to claim 1 wherein X11 is Nle or D-Nle; or an amide, an ester or a salt of the polypeptide.

12. The polypeptide according to claim 1 selected from (SEQ ID NOS 46-57, respectively, in order of appearance):

pE-R-P-C*-L-S-C*-K-G-P-Nle-P-F-OH pE-R-P-C*-L-S-C*-K-G-P-Nle-P-(N-Me)F-OH pE-R-P-C*-L-S-C*-K-G-P-Nle-P-NH(Phenethyl)

pE-R-P-C*-L-S-C*-K-G-P-Nle-NH(Phenethyl)

pE-R-P-C*-L-S-C*-K-G-P-(D-Nle)-NH(Phenethyl)

pE-R-P-C*-L-S-C*-K-G-P-(D-Nle)-a-f-OH pE-R-P-C*-L-S-C*-K-G-P-(D-Nle)-f-OH pE-R-P-C*-L-S-C*-F-G-P-(D-Nle)-a-f-OH

H-R-P-C*-L-S-C*-K-(D-Nle)-a-f-OH pE-R-P-hC*-L-S-C*-K-G-P-f-a-f-OH pE-R-P-c*-L-S-(D-hC)*-K-G-P-(D-Nle)-a-y-OH pE-R-P-(D-hC)*-L-S-hC*-K-G-P-(D-Nle)-(D-Nva)-f-OH wherein the two amino acids labeled with "*" represent the amino acids forming a disulfide; or an amide, an ester or a salt of the polypeptide.

13. A bioconjugate or multimer thereof comprising:
a) a peptide or polypeptide according to claim 1, or an amide, an ester or a salt thereof, and
b) a half-life extending moiety;
wherein said peptide or polypeptide and half-life extending moiety are covalently linked or fused, optionally via a linker.

14. The bioconjugate or a multimer thereof, according to claim 13, wherein the half-life extending moiety is an IgG constant domain or fragment thereof or a human Serum Albumin.

15. The bioconjugate according to claim 13 wherein the half-life extending moiety is a fatty acid.

16. A Combination comprising a therapeutically effective amount of a polypeptide, an amide, an ester or a salt thereof, according to claim 1, and one or more therapeutically active co-agent.

17. A combination according to claim 16 wherein the co-agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

18. A pharmaceutical composition comprising a therapeutically effective amount of a polypeptide, an amide, an ester or a salt thereof, according to claim 1, and one or more pharmaceutically acceptable carriers.

19. A pharmaceutical composition comprising a therapeutically effective amount of a bioconjugate according to claim 13, and one or more pharmaceutically acceptable carriers.

20. The polypeptide according to claim 1 having SEQ ID NO: 50:

pE-R-P-C*-L-S-C*-K-G-P-(D-Nle)-NH(Phenethyl).

21. A pharmaceutical composition comprising a therapeutically effective amount of a polypeptide according to claim 20, and one or more pharmaceutically acceptable carriers.

22. A Combination comprising a therapeutically effective amount of a polypeptide, an amide, an ester of a salt thereof, according to claim 20, and one or more therapeutically active co-agent.

23. A combination according to claim 22 wherein the co-agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

* * * * *

UNITED STATES PATENT AND TRADEMARK OFFICE
CERTIFICATE OF CORRECTION

| | | |
|---|---|---|
| PATENT NO. | : 9,266,925 B2 | Page 1 of 1 |
| APPLICATION NO. | : 14/336262 | |
| DATED | : February 23, 2016 | |
| INVENTOR(S) | : Frederic Zecri et al. | |

It is certified that error appears in the above-identified patent and that said Letters Patent is hereby corrected as shown below:

Claims

In claim 1, please replace:

"X7 is C, c, hC or D-hC; and the side chain of X7 forms a disulfide bond with the side chain;"

with

"X7 is C, c, hC or D-hC; and the side chain of X7 forms a disulfide bond with the side chain of X4;"

Signed and Sealed this
Tenth Day of May, 2016

Michelle K. Lee
*Director of the United States Patent and Trademark Office*